US012662494B2

(12) United States Patent
Kamioka et al.

(10) Patent No.: US 12,662,494 B2
(45) Date of Patent: Jun. 23, 2026

(54) OPTICALLY ACTIVE BRIDGED PIPERIDINE DERIVATIVE

(71) Applicant: Sumitomo Pharma Co., Ltd., Osaka (JP)

(72) Inventors: Seiji Kamioka, Toyonaka (JP); Naoaki Shimada, Takatsuki (JP); Hitoshi Ban, Nishinomiya (JP); Kazuto Yamazaki, Ikoma (JP); Akihiko Arakawa, Odawara (JP); Wataru Hirose, Suita (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 638 days.

(21) Appl. No.: 17/265,920

(22) PCT Filed: Aug. 7, 2019

(86) PCT No.: PCT/JP2019/031132
§ 371 (c)(1),
(2) Date: Feb. 4, 2021

(87) PCT Pub. No.: WO2020/032105
PCT Pub. Date: Feb. 13, 2020

(65) Prior Publication Data

US 2021/0198283 A1 Jul. 1, 2021

(30) Foreign Application Priority Data

Aug. 8, 2018 (JP) ................................ 2018-149547

(51) Int. Cl.

| | |
|---|---|
| ***C07D 519/00*** | (2006.01) |
| ***A61P 35/02*** | (2006.01) |
| ***C07D 453/06*** | (2006.01) |
| ***C07D 513/04*** | (2006.01) |

(52) U.S. Cl.
CPC ............ *C07D 519/00* (2013.01); *A61P 35/02* (2018.01); *C07D 453/06* (2013.01); *C07D 513/04* (2013.01)

(58) Field of Classification Search
CPC .. C07D 453/06; C07D 471/08; C07D 471/10; C07D 519/00
See application file for complete search history.

(56) References Cited

U.S. PATENT DOCUMENTS

| | | | | |
|---|---|---|---|---|
| 11,325,921 | B2 * | 5/2022 | Kamioka ................ | A61P 35/02 |
| 11,369,605 | B2 * | 6/2022 | Kamioka ................ | A61P 43/00 |
| 2014/0275070 | A1 | 9/2014 | Grembecka et al. | |
| 2019/0010167 | A1 | 1/2019 | Claremon et al. | |
| 2021/0024547 | A1 | 1/2021 | Kamioka et al. | |

FOREIGN PATENT DOCUMENTS

| | | | |
|---|---|---|---|
| WO | WO 2014/164543 | A1 | 10/2014 |
| WO | WO 2017/112768 | A1 | 6/2017 |
| WO | WO-2017207387 | A1 * | 12/2017 |
| WO | WO 2018/024602 | A1 | 2/2018 |
| WO | WO 2018/050684 | A1 | 3/2018 |
| WO | WO 2018/050686 | A1 | 3/2018 |
| WO | WO 2019/189732 | A1 | 10/2019 |

OTHER PUBLICATIONS

Tilsed et al., "Cancer chemotherapy: insights into cellular and tumor microenvironmental mechanisms of action" Frontiers in Oncology vol. 12:960317 DOI 10.3389/fonc.2022.960317 (Year: 2022).*

Brzezinka et al., "Characterization of the Menin-MLL Interaction as Therapeutic Cancer Target" Cancers 12:201 doi:10.3390/cancers12010201 (Year: 2020).*

Ozyerli-Goknar et al., "A Box of Chemistry to Inhibit the MEN1 Tumor Suppressor Gene Promoting Leukemia" ChemMedChem vol. 16 pp. 1391-1402 DOI 10.1002/cmdc.202000972 (Year: 2021).*

Malik et al., "Targeting the MLL complex in castration-resistant prostate cancer" Nature Medicine vol. 21 No. 4 pp. 344-354 doi:10.1038/nm.3830 (Year: 2015).*

Svoboda et al., "Tumorigenicity of Ewing Sarcoma is critically dependnet on the trithorax proteins MLL1 and menin" Oncotarget vol. 8 No. 1 pp. 458-471 (Year: 2017).*

Imachi et al., "Menin, a product of the MENI gene, binds to estrogen receptor to enhance its activity in breast cancer cells: possibility of a novel predictive factor for tamoxifen resistance" Breast Cancer Res Treat vol. 122 pp. 395-407, DOI: 10.1007/s10549-009-0581-0 (Year: 2010).*

Dreijerink et al., "Enhancer-Mediated Oncogenic Function of the Menin Tumor Suppressor in Breast Cancer" Cell Reports vol. 18 pp. 2359-2372, DOI:10.1016/j.celrep.2017.02.025 (Year: 2017).*

(Continued)

*Primary Examiner* — Andrea Olson
(74) *Attorney, Agent, or Firm* — Oblon, McClelland, Maier & Neustadt, L.L.P.

(57) ABSTRACT

The present invention relates to the compound of formula (1a) wherein a-d and p are 1 or 2, $R^1$-$R^4$ are hydrogen atom or the like, and $R^{18}$ is —$CF_3$ or the like, or a pharmaceutically acceptable salt thereof, which has an anticancer effect by inhibiting the binding between a MLL fusion protein that is fused with AF4, AF9, or the like, which is a representative fusion partner gene causing MLL leukemia, and menin.

(1a)

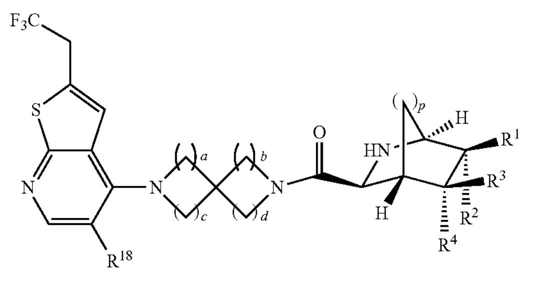

10 Claims, No Drawings

(56) References Cited

OTHER PUBLICATIONS

Cierpicki et al., "Challenges and opportunities in targeting the menin-MLL interaction" Future Med Chem vol. 6 No. 4 pp. 447-462, doi:10/4155/fmc.13.214 (Year: 2014).*
He et al., "High-Affinity Small-Molecule Inhibitors of the Menin-Mixed Lineage Leukemia (MLL) Interaction Closely Mimic a Natural Protein-Protein interaction" Journal of Medicinal Chemistry vol. 57 pp. 1543-1556, DOI:10.1021/jm401868d (Year: 2014).*
Japanese patent application 2018-067187, of record in the application file of U.S. Appl. No. 17/042,479 (Year: 2018).*
Extended European Search Report issued May 6, 2022, in corresponding European Patent Application No. 19846598.1, 5 pages.
International Search Report issued Nov. 12, 2019 in PCT/JP2019/031132 (submitting English translation only), 2 pages.
International Preliminary Report on Patentability and Written Opinion issued Feb. 9, 2021 in PCT/JP2019/031132 (submitting English translation only), 5 pages.
A. Thomas Look, "Oncogenic Transcription Factors in the Human Acute Leukemias", http://science.sciencemag.org/, Science, vol. 278 (5340), Nov. 7, 1997, pp. 1059-1064.
Akihiko Yokoyama, et al., "The Menin Tumor Suppressor Protein Is an Essential Oncogenic Cofactor for MLL-Associated Leukemogenesis", Cell, vol. 123 (2), Oct. 21, 2005, pp. 207-218.
Akihiko Yokoyama, et al., "Menin Critically Links MLL Proteins with LEDGF on Cancer-Associated Target Genes", Cancer Cell, vol. 14 (1), Jul. 2008, pp. 36-46.
Rohit Malik, et al., "Targeting the MLL complex in castration-resistant prostate cancer", Nature Medicine, vol. 21, No. 4, Apr. 2015, pp. 344-352.
Hitomi Imachi, et al., "Menin, a product of the *MENI* gene, binds to estrogen receptor to enhance its activity in breast cancer cells: possibility of a novel predictive factor for tamoxifen resistance", Breast Cancer Res. Treat., vol. 122 (2), (2010), pp. 395-407.
Laurie K. Svoboda, et al., "Tumorigenicity of Ewing sarcoma is critically dependent on the trithorax proteins MLL1 and menin", Oncotarget, www.impactjournals.com/oncotarget/, vol. 8, No. 1, (2017), pp. 458-471.

* cited by examiner

OPTICALLY ACTIVE BRIDGED PIPERIDINE DERIVATIVE

This application claims priority benefit of PCT/JP2019/031132, filed Aug. 7, 2019 which in turn claims benefit of Japanese application 2018-149547, filed Aug. 8, 2018; the contents of each is incorporated herein by reference.

TECHNICAL FIELD

The present invention relates to an optically active bridged piperidine derivative useful as a medicament, or a pharmaceutically acceptable salt thereof, and a pharmaceutical composition comprising it, or a medicament comprising the composition for treating or preventing pathology related to the binding of menin and MLL.

BACKGROUND ART

MLL leukemia is a disease that accounts for about 6 to 7% of acute myeloid leukemia (AML) and acute lymphoblastic leukemia (ALL), and about 1100 people are newly diagnosed with MLL leukemia each year in America. It has been reported that major fusion partner genes that cause MLL leukemia are likely to be AF9, ELL, ENL, AF10, and AF6 in AML, and AF4, ENL, and AF9 in ALL (Non-patent literature 1).

It is inferred that a MLL fusion protein fused with a fusion partner gene can cause unrestrained proliferation of undifferentiated hematopoietic cells to lead to leukemia (Non-patent literature 2). It has been reported that a MLL fusion protein firstly binds to menin to form a complex. Accordingly, it is expected that canceration caused by a MLL fusion protein can be prevented by inhibiting the first binding between a MLL fusion protein and menin (Non-patent literature 3).

It has been reported that MLL acts as an activation cofactor of an androgen signal in prostate cancer. Accordingly, it is expected that a small molecular inhibitor which is targeted to the binding inhibition of menin-MLL is useful as a medicament for treating the cancer (Non-patent literature 4).

It has been reported that menin acts as an activation cofactor of an estrogen signal in breast cancer. Accordingly, it is expected that a small molecular inhibitor which is targeted to the binding inhibition of menin-MLL is useful as a medicament of the cancer (Non-patent literature 5).

It has been reported that menin or MLL is important for tumor progression in Ewing's sarcoma, liver cancer, and p53 gain-of-function mutation cancer, and it is expected that a small molecular inhibitor which is targeted to the binding inhibition of menin-MLL is useful as a medicament of the cancers (Non-patent literature 6).

Patent literatures 1 to 4 disclose small molecular inhibitors which are targeted to the binding inhibition of menin-MLL. The present compound of the following formula (1) which is an optically active bridged piperidine derivative, however, is not disclosed or suggested in these literatures.

PRIOR ART (Patent Reference)
[Patent Literature 1] WO2014/164543
[Patent Literature 2] WO2017/112768
[Patent Literature 3] WO2018/050684
[Patent Literature 4] WO2018/050686

(Non-patent Reference)
[Non-patent Literature 1] Look A. T, Science, 278 (5340): 1059-1064 (1997)
[Non-patent Literature 2] Yokoyama A, et al., Cell 123 (2): 207-218 (2005)
[Non-patent Literature 3] Yokoyama, A et al., Cancer Cell. 14 (1): 34-46 (2008)
[Non-patent Literature 4] Malik, R. et al., Nature Medicine. 21 (4): 344-352 (2015)
[Non-patent Literature 5] Imachi, H et al., Breast Cancer Res Treat. 122 (2): 395-407 (2010)
[Non-patent Literature 6] Svoboda, L. K. et al., Oncotargrt. 8 (1): 458-471 (2017)

SUMMARY OF INVENTION

Technical Problem

The purpose of the present invention may be to provide a compound which has an antitumor effect by inhibiting the binding between a MLL fusion protein that is fused with AF4, AF9, etc., which is a representative fusion partner gene causing MLL leukemia, and menin. More preferably, the purpose of the present invention may be to provide a compound which has an antitumor effect by inhibiting the menin-MLL binding, and also has a good pharmacokinetic character. In other words, the purpose of the present invention is to provide an antitumor medicament with high therapeutic effect.

Solution to Problem

The present inventors have extensively studied to reach the above purpose, and then have found that a compound of the following formula (1) or a pharmaceutically acceptable salt thereof (hereinafter, it may be referred to as "the present compound") has an excellent antitumor effect through a potent inhibitory effect on the menin-MLL binding. Based upon the findings, the present invention has been achieved.

Accordingly, the present invention is described as follows:

(Item 1)

A compound of formula (1):

(1)

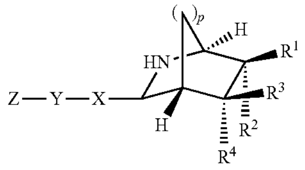

or a pharmaceutically acceptable salt thereof, wherein p is 1 or 2;

$R^1$ and $R^2$ are each independently hydrogen atom or -M-Q; or $R^1$ and $R^2$ may be combined together to form $=CR^{5A}R^{6A}$, $=N-NR^{5B}R^{6B}$, or $=N-OR^{5B}$;

M is, each independently if there are plural, optionally-substituted $C_{1-6}$ alkylene, optionally-substituted $C_{2-6}$ alkenylene, optionally-substituted $C_{2-6}$ alkynylene, optionally-substituted $C_{3-10}$ cycloalkylene, optionally-substituted 3- to 10-membered saturated heterocyclyl, optionally-substituted $C_{6-10}$ arylene, or optionally-substituted 5- to 12-membered heteroarylene;

Q is, each independently if there are plural, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl;

$R^{5A}$ and $R^{6A}$ are each independently hydrogen atom, halogen atom, cyano, nitro, —$COR^7$, carboxyl, —$CO_2R^7$, —$CONR^8R^9$, sulfonic acid, —$SO_2R^7$, —$SO_2NR^8R^9$, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl, and if there are plural $R^{5A}$ or $R^{6A}$, each $R^{5A}$ or $R^{6A}$ may be the same or different, or when RSA and $R^{6A}$ are both optionally-substituted $C_{1-6}$ alkyl, they may be combined with the carbon atom to which they are each attached to form 3- to 8-membered saturated carbocycle;

$R^{5B}$ and $R^{6B}$ are each independently hydrogen atom, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl, and if there are plural $R^{5B}$ or $R^{6B}$, each $R^{5B}$ or $R^{6B}$ may be the same or different, or when $R^{5B}$ and $R^{6B}$ are both optionally-substituted $C_{1-6}$ alkyl, they may be combined with the nitrogen atom to which they are each attached to form 3- to 8-membered nitrogen-containing saturated heterocycle;

$R^7$ is, each independently if there are plural, $C_{1-6}$ alkyl;

$R^8$ and $R^9$ are each independently hydrogen atom or $C_{1-6}$ alkyl, and if there are plural $R^8$ or $R^9$, each $R^8$ or $R^9$ may be the same or different, or when $R^8$ and $R^9$ are both $C_{1-6}$ alkyl, they may be combined with the nitrogen atom to which they are each attached to form 3- to 8-membered nitrogen-containing saturated heterocycle;

$R^3$ and $R^4$ are each independently hydrogen atom, hydroxy, halogen atom, $C_{1-6}$ alkyl, $C_{2-6}$ alkenyl, $C_{2-6}$ alkynyl, $C_{3-10}$ cycloalkyl, —$OR^{10}$, 3- to 10-membered saturated heterocyclyl, $C_{6-10}$ aryl, or 5- to 12-membered heteroaryl, wherein the alkyl may be substituted with 1 to 3 fluorine atoms, the cycloalkyl and the saturated heterocyclyl may be each independently substituted with the same or different 1 to 5 substituents selected from the group consisting of fluorine atom and $C_{1-3}$ alkyl, and the aryl and the heteroaryl may be each independently substituted with the same or different 1 to 5 substituents selected from the group consisting of fluorine atom, chlorine atom, bromine atom, and $C_{1-3}$ alkyl, or $R^3$ and $R^4$ may be combined together to form =O, =$CR^{5A}R^{6A}$, =N—$NR^{5B}R^{6B}$, or =N—$OR^{5B}$;

$R^{10}$ is, each independently if there are plural, hydrogen atom, $C_{1-6}$ alkyl (wherein the $C_{1-6}$ alkyl may be substituted with the same or different 1 to 5 substituents selected from the group consisting of $C_{3-10}$ cycloalkyl optionally-substituted with the same or different 1 to 5 substituents selected from the group consisting of fluorine atom and $C_{1-3}$ alkyl; 3- to 10-membered saturated heterocyclyl optionally-substituted with the same or different 1 to 5 substituents selected from the group consisting of fluorine atom and $C_{1-3}$ alkyl; $C_{6-10}$ aryl optionally-substituted with the same or different 1 to 5 substituents selected from the group consisting of fluorine atom, chlorine atom, bromine atom, and $C_{1-3}$ alkyl; and 5- to 12-membered heteroaryl optionally-substituted with the same or different 1 to 5 substituents selected from the group consisting of fluorine atom, chlorine atom, bromine atom, and $C_{1-3}$ alkyl), $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl (wherein the cycloalkyl and the saturated heterocyclyl may be each independently substituted with the same or different 1 to 5 substituents selected from the group consisting of fluorine atom and $C_{1-3}$ alkyl; and the aryl and the heteroaryl may be each independently substituted with the same or different 1 to 5 substituents selected from the group consisting of fluorine atom, chlorine atom, bromine atom, and $C_{1-3}$ alkyl);

X is —C(O)— or $C_{1-6}$ alkylene;

Y is the following formula (Y-1), (Y-2), (Y-3), (Y-4), or (Y-5):

(Y-1)

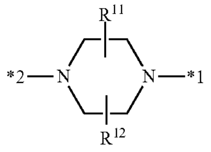

(Y-2)

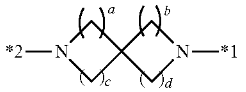

(Y-3)

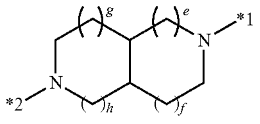

(Y-4)

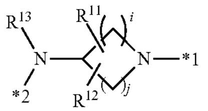

(Y-5)

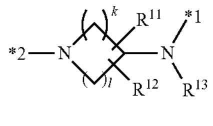

wherein *1 is a bonding site to X, and *2 is a bonding site to Z;

$R^{11}$, $R^{12}$, and $R^{13}$ are each independently hydrogen atom or $C_{1-3}$ alkyl, or when $R^{11}$ and $R^{12}$ are both $C_{1-3}$ alkyl, they may be combined with the carbon atom to which they are each attached to form 3- to 8-membered saturated carbocycle or 5-10 to 8-membered nitrogen-containing saturated heterocycle;

a, b, c, and d are each independently 1 or 2;

e, f, g, and h are each independently 0 or 1;

i, j, k, and 1 are each independently 1, 2, or 3;

Z is the following formula (Z-1):

(Z-1)

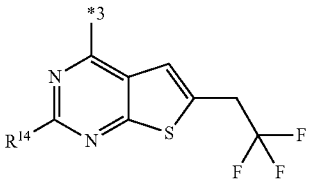

wherein *3 is a bonding site to Y;

$R^{14}$ is hydrogen atom, halogen atom, $—OR^{15}$, $—NR^{16}R^{17}$, cyano, $C_{1-3}$ alkyl, $C_{2-4}$ alkenyl, or $C_{2-4}$ alkynyl;

$R^{15}$ is $C_{1-6}$ alkyl;

$R^{16}$ and $R^{17}$ are each independently hydrogen atom or $C_{1-6}$ alkyl, or when $R^{16}$ and $R^{17}$ are both $C_{1-6}$ alkyl, they may be combined with the nitrogen atom to which they are each attached to form 3- to 8-membered nitrogen-containing saturated heterocycle;

U is $CR^{18}$ or nitrogen atom;

$R^{18}$ is hydrogen atom, halogen atom, $C_{1-3}$ alkyl (wherein the alkyl may be substituted with the same or different 1 to 5 substituents selected from the group consisting of fluorine atom, $—OR^{19}$, and $—NR^{19}R^{20}$), $—CO_2R^{19}$, $—CONR^{19}R^{20}$, or cyano;

$R^{19}$ and $R^{20}$ are each independently hydrogen atom or $C_{1-3}$ alkyl, and if there are plural $R^{19}$ or $R^{20}$, each $R^{19}$ or $R^{20}$ may be the same or different, or when $R^{19}$ and $R^{20}$ are both $C_{1-3}$ alkyl, they may be combined with the nitrogen atom to which they are each attached to form 3- to 8-membered nitrogen-containing saturated heterocycle;

provided that when both of R and $R^2$ are hydrogen atom, then $R^3$ and $R^4$ are $=CR^{5A}R^{6A}$, $=N—NR^{5B}R^{6B}$, or $=N—OR^5$.

(Item 2)

The compound of Item 1 or a pharmaceutically acceptable salt thereof, wherein

M is $C_{1-6}$ alkylene, $C_{2-6}$ alkenylene, $C_{2-6}$ alkynylene, $C_{3-10}$ cycloalkylene, 3- to 10-membered saturated heterocyclyl, $C_{6-10}$ arylene, or 5- to 12-membered heteroarylene, wherein the alkylene, the alkenylene, the alkynylene, the cycloalkylene, the saturated heterocyclyl, the arylene, and the heteroarylene may be independently substituted with the same or different 1 to 5 substituents selected from the group consisting of (1) halogen atom,
(2) hydroxy,
(3) $C_{6-10}$ aryl,
(4) 5- to 12-membered heteroaryl,
(5) $C_{1-6}$ alkyl,
(6) $C_{2-6}$ alkenyl,
(7) $C_{2-6}$ alkynyl,
(8) $C_{1-6}$ alkoxy,
(9) $C_{3-10}$ cycloalkyl,
(10) 3- to 10-membered saturated heterocyclyl,
(11) carboxyl,
(12) $—COR^{21A}$,
(13) $—CO_2R^{21A}$,
(14) $—CONR^{22A}R^{23A}$,
(15) $—NR^{22A}R^{23A}$,
(16) $—NR^{22A}COR^{21A}$,
(17) $—NR^{22A}SO_2R^{21A}$,
(18) $—SO_2R^{21A}$,
(19) $—SO_2NR^{22A}R^{23A}$,
(20) sulfonic acid,
(21) phosphoric acid,
(22) cyano, and
(23) nitro wherein the said (3) $C_{6-10}$ aryl, (4) 5- to 12-membered heteroaryl, (5) $C_{1-6}$ alkyl, (6) $C_{2-6}$ alkenyl, (7) $C_{2-6}$ alkynyl, (8) $C_{1-6}$ alkoxy, (9) $C_{3-10}$ cycloalkyl, and (10) 3- to 10-membered saturated heterocyclyl may be independently substituted with the same or different 1 to 5 substituents selected from the group consisting of (a) halogen atom,
(b) hydroxy,
(c) $C_{6-10}$ aryl,
(d) 5- to 10-membered heteroaryl,
(e) $C_{1-6}$ alkyl,
(f) $C_{2-6}$ alkenyl,
(g) $C_{2-6}$ alkynyl,
(h) $C_{1-6}$ alkoxy,
(i) $C_{3-10}$ cycloalkyl,
(j) 3- to 10-membered saturated heterocyclyl,
(k) carboxyl,
(l) $—COR^{21B}$,
(m) $—CO_2R^{21B}$,
(n) $—CONR^{22B}R^{23B}$,
(o) $—NR^{22B}R^{23B}$,
(p) $—NR^{22B}COR^{21B}$,
(q) $—NR^{22B}SO_2R^{21B}$,
(r) $—SO_2R^{21B}$,
(s) $—SO_2NR^{22B}R^{23B}$,
(t) sulfonic acid,
(u) phosphoric acid,
(v) cyano, and
(w) nitro;

$R^{21A}$ is, each independently if there are plural, $C_{1-6}$ alkyl;

$R^{22A}$ and $R^{23A}$ are each independently hydrogen atom or $C_{1-6}$ alkyl, and if there are plural $R^{22A}$ or $R^{23A}$, each $R^{22A}$ or $R^{23A}$ may be the same or different, or when $R^{22A}$ and $R^{23A}$ are both $C_{1-6}$ alkyl, they may be combined with the nitrogen atom to which they are attached to form 3- to 8-membered nitrogen-containing saturated heterocycle;

$R^{21B}$ is, each independently if there are plural, $C_{1-6}$ alkyl; and $R^{22B}$ and $R^{23B}$ are each independently hydrogen atom or $C_{1-6}$ alkyl, and if there are plural $R^{22B}$ or $R^{23B}$, each $R^{22B}$ or $R^{23B}$ may be the same or different, or when $R^{22B}$ and $R^{23B}$ are both $C_{1-6}$ alkyl, they may be combined with the nitrogen atom to which they are attached to form 3- to 8-membered nitrogen-containing saturated heterocycle.

(Item 3)

The compound of Item 1 or 2 or a pharmaceutically acceptable salt thereof, wherein M is $C_{1-6}$ alkylene, $C_{2-6}$ alkenylene, $C_{2-6}$ alkynylene, $C_{3-10}$ cycloalkylene, 3- to 10-membered saturated heterocyclyl, $C_{6-10}$ arylene, or 5- to 12-membered heteroarylene, wherein the alkynylene, the alkylene, the alkenylene, the cycloalkylene, the saturated heterocyclyl, the arylene, and the heteroarylene may be independently substituted with the same or different 1 to 5 substituents selected from the group consisting of (1') halogen atom,
(2') hydroxy,
(3') $C_{1-6}$ alkyl,
(4') $C_{2-6}$ alkynyl,
(5') $C_{1-6}$ alkoxy, (6') $C_{3-7}$ cycloalkyl,
(7') 3- to 7-membered saturated heterocyclyl,
(8') —$COR^{21A}$,
(9') —$CO_2R^{21A}$,
(10') —$CONR^{22A}R^{23A}$,
(11') —$NR^{22A}R^{23A}$,
(12') —$NR^{22A}COR^{21A}$,
(13') —$NR^{22A}SO_2R^{21A}$,
(14') —$SO_2R^{21A}$,
(15') —$SO_2NR^{22A}R^{23A}$,
(16') cyano, and
(17') nitro;

$R^{21A}$ is, each independently if there are plural, $C_{1-6}$ alkyl; and $R^{22A}$ and $R^{23A}$ are each independently hydrogen atom or $C_{1-6}$ alkyl, and if there are plural $R^{22A}$ or $R^{23A}$, each $R^{22A}$ or $R^{23A}$ may be the same or different, or when $R^{22A}$ and $R^{23A}$ are both $C_{1-6}$ alkyl, they may be combined with the nitrogen atom to which they are attached to form 3- to 6-membered nitrogen-containing saturated heterocycle.

(Item 4)

The compound of any one of Items 1 to 3 or a pharmaceutically acceptable salt thereof, wherein Q is $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be independently substituted with the same or different 1 to 5 substituents selected from the group consisting of (1) halogen atom,
(2) hydroxy,
(3) $C_{6-10}$ aryl,
(4) 5- to 12-membered heteroaryl,
(5) $C_{1-6}$ alkyl,
(6) $C_{2-6}$ alkenyl,
(7) $C_{2-6}$ alkynyl,
(8) $C_{1-6}$ alkoxy,
(9) $C_{3-10}$ cycloalkyl,
(10) 3- to 10-membered saturated heterocyclyl,
(11) carboxyl,
(12) —$COR^{21C}$,
(13) —$CO_2R^{21C}$,
(14) —$CONR^{22C}R^{23C}$,
(15) —$NR^{22C}R^{23C}$,
(16) —$NR^{22C}COR^{21C}$,
(17) —$NR^{22C}SO_2R^{21C}$,
(18) —$SO_2R^{21C}$,
(19) —$SO_2NR^{22C}R^{23C}$,
(20) sulfonic acid,
(21) phosphoric acid,
(22) cyano, and
(23) nitro wherein the said (3) $C_{6-10}$ aryl, (4) 5- to 12-membered heteroaryl, (5) $C_{1-6}$ alkyl, (6) $C_{2-6}$ alkenyl, (7) $C_{2-6}$ alkynyl, (8) $C_{1-6}$ alkoxy, (9) $C_{3-10}$ cycloalkyl, and (10) 3- to 10-saturated heterocyclyl may be independently membered substituted with the same or different 1 to 5 substituents selected from the group consisting of (a) halogen atom,
(b) hydroxy,
(c) $C_{6-10}$ aryl,
(d) 5- to 10-membered heteroaryl,
(e) $C_{1-6}$ alkyl,
(f) $C_{2-6}$ alkenyl,
(g) $C_{2-6}$ alkynyl,
(h) $C_{1-6}$ alkoxy,
(i) $C_{3-10}$ cycloalkyl,
(j) 3- to 10-membered saturated heterocyclyl,
(k) carboxyl,
(l) —$COR^{21D}$,
(m) —$CO_2R^{21D}$,
(n) —$CONR^{22D}R^{23D}$,
(o) —$NR^{22D}R^{23D}$,
(p) —$NR^{22D}COR^{21D}$,
(q) —$NR^{22D}SO_2R^{21D}$,
(r) —$SO_2R^{21D}$,
(s) —$SO_2NR^{22D}R^{23D}$,
(t) sulfonic acid,
(u) phosphoric acid,
(v) cyano, and
(w) nitro;

$R^{21C}$ is, each independently if there are plural, $C_{1-6}$ alkyl;

$R^{22C}$ and $R^{23C}$ are each independently hydrogen atom or $C_{1-6}$ alkyl, and if there are plural $R^{22C}$ or $R^{23C}$, each $R^{22C}$ or $R^{23C}$ may be the same or different, or when $R^{22C}$ and $R^{23C}$ are both $C_{1-6}$ alkyl, they may be combined with the nitrogen atom to which they are attached to form 3- to 8-membered nitrogen-containing saturated heterocycle;

$R^{21D}$ is, each independently if there are plural, $C_{1-6}$ alkyl; and $R^{22D}$ and $R^{23D}$ are each independently hydrogen atom or $C_{1-6}$ alkyl, and if there are plural $R^{22D}$ or $R^{23D}$, each $R^{22D}$ or $R^{23D}$ may be the same or different, or when $R^{22D}$ and $R^{23D}$ are both $C_{1-6}$ alkyl, they may be combined with the nitrogen atom to which they are attached to form 3- to 8-membered nitrogen-containing saturated heterocycle.

(Item 5)

The compound of any one of Items 1 to 4 or a pharmaceutically acceptable salt thereof, wherein Q is $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be independently substituted with the same or different 1 to 5 substituents selected from the group consisting of (1') halogen atom,
(2') hydroxy,
(3') $C_{1-6}$ alkyl,
(4 ') $C_{2-6}$ alkynyl,
(5') $C_{1-6}$ alkoxy,
(6') $C_{3-7}$ cycloalkyl,
(7') 3- to 7-membered saturated heterocyclyl,
(8') —$COR^{21C}$,
(9') —$CO_2R^{21C}$,
(10') —$CONR^{22C}R^{23C}$,
(11') —$NR^{22C}R^{23C}$,
(12') —$NR^{22C}COR^{23C}$,
(13') —$NR^{22C}SO_2R^{21C}$,
(14') —$SO_2R^{21C}$,
(15') —$SO_2NR^{22C}R^{23C}$,
(16') cyano, and
(17') nitro;

$R^{21C}$ is, each independently if there are plural, $C_{1-6}$ alkyl; and $R^{22C}$ and $R^{23C}$ are each independently hydrogen atom or $C_{1-6}$ alkyl, and if there are plural $R^{22C}$ or $R^{23C}$, each $R^{22C}$ or $R^{23C}$ may be the same or different, or when $R^{22C}$ and $R^{23C}$ are both $C_{1-6}$ alkyl, they may be combined with the nitrogen atom to which they are attached to form 3- to 6-membered nitrogen-containing saturated heterocycle.

(Item 6)

The compound of any one of Items 1 to 5 or a pharmaceutically acceptable salt thereof, wherein $R^1$ and $R^2$ are combined together to form $=CR^{5A}R^{6A}$;

$R^{5A}$ and $R^{6A}$ are each independently hydrogen atom, $C_{1-6}$ alkyl, $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkyl, the alkenyl, and the alkynyl may be each independently substituted with the same or different 1 to 3 substituents selected from the group consisting of fluorine atom, chlorine atom, bromine atom, hydroxy, $C_{2-4}$ alkynyl, $C_{1-3}$ alkoxy, $-CONR^{22E}R^{23E}$, $-NR^{22E}R^{23E}$, $-NR^{22E}COR^{21E}$, $-NR^{22E}SO_2R^{21E}$, $-SO_2R^{21E}$, $-SO_2NR^{22E}R^{23E}$, and cyano; and the cycloalkyl, the saturated heterocyclyl, the aryl, and the heteroaryl may be each independently substituted with the same or different 1 to 5 substituents selected from the group consisting of fluorine atom, chlorine atom, bromine atom, hydroxy, $C_{1-3}$ alkyl, $C_{2-4}$ alkynyl, $C_{1-3}$ alkoxy, $-CONR^{22E}R^{23E}$, $-NR^{22E}R^{23E}$, $-NR^{22E}COR^{21E}$, $-NR^{22E}SO_2R^{21E}$, $-SO_2R^{21E}$, $-SO_2NR^{22E}R^{23E}$, and cyano;

$R^{21E}$ is, each independently if there are plural, $C_{1-6}$ alkyl; and $R^{22E}$ and $R^{23E}$ are each independently hydrogen atom or $C_{1-6}$ alkyl, and if there are plural $R^{22E}$ or $R^{23E}$, each $R^{22E}$ or $R^{23E}$ may be the same or different, or when $R^{22E}$ and $R^{23E}$ are both $C_{1-6}$ alkyl, they may be combined with the nitrogen atom to which they are each attached to form 3- to 6-membered nitrogen-containing saturated heterocycle.

(Item 7)

The compound of any one of Items 1 to 5 or a pharmaceutically acceptable salt thereof, wherein $R^1$ and $R^2$ are combined together to form $=N-NR^{5B}R^{6B}$ or $=N-OR^{5B}$;

$R^{5B}$ and $R^{6B}$ are each independently hydrogen atom, $C_{1-6}$ alkyl, $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkyl, the alkenyl, and the alkynyl may be each independently substituted with the same or different 1 to 3 substituents selected from the group consisting of fluorine atom, chlorine atom, bromine atom, hydroxy, $C_{2-4}$ alkynyl, $C_{1-3}$ alkoxy, $-CONR^{22E}R^{23E}$, $-NR^{22E}R^{23E}$, $-NR^{22E}COR^{21E}$, $-NR^{22E}SO_2R^{21E}$, $-SO_2R^{21E}$, $-SO_2NR^{22E}R^{23E}$, and cyano; and the cycloalkyl, the saturated heterocyclyl, the aryl, and the heteroaryl may be each independently substituted with the same or different 1 to 5 substituents selected from the group consisting of fluorine atom, chlorine atom, bromine atom, hydroxy, $C_{1-3}$ alkyl, $C_{2-4}$ alkynyl, $C_{1-3}$ alkoxy, $-CONR^{22E}R^{23E}$, $-NR^{22E}R^{23E}$, $-NR^{22E}COR^{21E}$, $-NR^{22E}SO_2R^{21E}$, $-SO_2R^{21E}$, $-SO_2NR^{22E}R^{23E}$, and cyano;

$R^{21E}$ is, each independently if there are plural, $C_{1-6}$ alkyl; and $R^{22E}$ and $R^{23E}$ are each independently hydrogen atom or $C_{1-6}$ alkyl, and if there are plural $R^{22E}$ or $R^{23E}$, each $R^{22E}$ or $R^{23E}$ may be the same or different, or when $R^{22E}$ and $R^{23E}$ are both $C_{1-6}$ alkyl, they may be combined with the nitrogen atom to which they are each attached to form 3- to 6-membered nitrogen-containing saturated heterocycle.

(Item 8)

The compound of any one of Items 1 to 7 or pharmaceutically acceptable salt thereof, wherein X is $-C(O)-$.

(Item 9)

The compound of any one of Items 1 to 8 or a pharmaceutically acceptable salt thereof, wherein Y is (Y-2).

(Item 10)

The compound of any one of Items 1 to 9 or a pharmaceutically acceptable salt thereof, wherein $R^{14}$ is hydrogen atom, $-OR^{15}$, $-NR^{16}R^{17}$, or $C_{1-3}$ alkyl, $R^{15}$ is $C_{1-3}$ alkyl, and $R^{16}$ and $R^{17}$ are each independently hydrogen atom or $C_{1-3}$ alkyl, or when $R^{16}$ and $R^{17}$ are both $C_{1-3}$ alkyl, they may be combined with the nitrogen atom to which they are each attached to form 3- to 6-membered nitrogen-containing saturated heterocycle.

(Item 11)

The compound of any one of Items 1 to 10 or a pharmaceutically acceptable salt thereof, wherein $R^{14}$ is hydrogen atom.

(Item 12)

The compound of any one of Items 1 to 11 or a pharmaceutically acceptable salt thereof, wherein U is $CR^{18}$, and $R^{18}$ is $-CF_3$ or cyano.

(Item 13)

The compound of Item 1 or a pharmaceutically acceptable salt thereof, wherein formula (1) is the following formula (1a):

(1a)

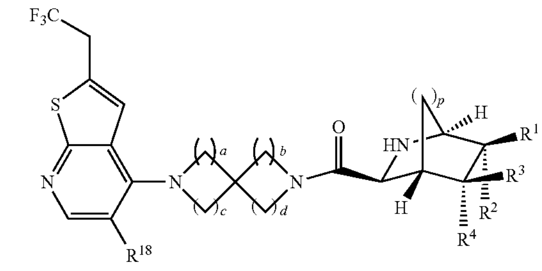

wherein p is 1 or 2;

a, b, c, and d are each independently 1 or 2;

$R^1$ and $R^2$ are each independently hydrogen atom or -M-Q; or $R^1$ and $R^2$ may be combined together to form $=CR^{5A}R^{6A}$;

M is, each independently if there are plural, $C_{1-6}$ alkylene which may be independently substituted with the same or different 1 to 3 substituents selected from the group consisting of fluorine atom, chlorine atom, bromine atom, hydroxy, $C_{2-4}$ alkynyl, $C_{1-3}$ alkoxy, $-CONR^{22A}R^{23A}$, $-NR^{22A}R^{23A}$, $NR^{22A}COR^{21}A$, $-NR^{22A}SO_2R^{21A}$, $-SO_2R^{21A}$, $-SO_2NR^{22A}R^{23A}$, and cyano;

Q is, each independently if there are plural, $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be independently substituted with the same or different 1 to 5 substituents selected from the group consisting of fluorine atom, chlorine atom, bromine atom, hydroxy, $C_{1-3}$ alkyl, $C_{2-4}$ alkynyl, $C_{1-3}$ alkoxy, $—CONR^{22C}R^{230}$, $—NR^{22C}R^{230}$, $—NR^{22C}COR^{21C}$, $—NR^{22C}SO_2R^{210}$, $—SO_2R^{210}$, $—SO_2NR^{22C}R^{23C}$, and cyano;

$R^{5A}$ and $R^{6A}$ are each independently hydrogen atom, $C_{1-6}$ alkyl, $C_3$-10 cycloalkyl, 3- to 10-membered saturated heterocyclyl, $C_{6-10}$ aryl, or 5- to 12-membered heteroaryl, wherein the alkyl may be each independently substituted with the same or different 1 to 3 substituents selected from the group consisting of fluorine atom, chlorine atom, bromine atom, hydroxy, $C_{2-4}$ alkynyl, $C_{1-3}$ alkoxy, $—CONR^{22E}R^{23E}$, $—NR^{22E}R^{23E}$, $—NR^{22E}COR^{21E}$, $—NR^{22E}SO_2R^{21E}$, $—SO_2R^{21E}$, $—SO_2NR^{22E}R^{23E}$, and cyano; the cycloalkyl, the saturated heterocyclyl, the aryl, and the heteroaryl may be each independently substituted with the same or different 1 to 5 substituents selected from the group consisting of fluorine atom, chlorine atom, bromine atom, hydroxy, $C_{1-3}$ alkyl, $C_{2-4}$ alkynyl, $C_{1-3}$ alkoxy, $—CONR^{22E}R^{23E}$, $—NR^{22E}R^{23E}$, $—NR^{22E}COR^{21E}$, $—NR^{22E}SO_2R^{21E}$, $—SO_2R^{21E}$, $—SO_2NR^{22E}R^{23E}$, and cyano, and if there are plural $R^{5A}$ or $R^{6A}$, each $R^{5A}$ or $R^{6A}$ may be the same or different, or when $R^{5A}$ and $R^{6A}$ are both $C_{1-6}$ alkyl, they may be combined with the carbon atom to which they are each attached to form 3- to 8-membered saturated carbocycle;

$R^{21A}$ is, each independently if there are plural, $C_{1-6}$ alkyl;

$R^{22A}$ and $R^{23A}$ are each independently hydrogen atom or $C_{1-6}$ alkyl, and if there are plural $R^{22A}$ or $R^{23A}$, each $R^{22A}$ or $R^{23A}$ may be the same or different, or when $R^{22A}$ and $R^{23A}$ are both $C_{1-6}$ alkyl, they may be combined with the nitrogen atom to which they are attached to form 3- to 6-membered nitrogen-containing saturated heterocycle;

$R^{21C}$ is, each independently if there are plural, $C_{1-6}$ alkyl;

$R^{22C}$ and $R^{23C}$ are each independently hydrogen atom or $C_{1-6}$ alkyl, and if there are plural $R^{22C}$ or $R^{23C}$, each $R^{22C}$ or $R^{23C}$ may be the same or different, or when $R^{22C}$ and $R^{23C}$ are both $C_{1-6}$ alkyl, they may be combined with the nitrogen atom to which they are attached to form 3- to 6-membered nitrogen-containing saturated heterocycle;

$R^{21E}$ is, each independently if there are plural, $C_{1-6}$ alkyl;

$R^{22E}$ and $R^{23E}$ are each independently hydrogen atom or $C_{1-6}$ alkyl, and if there are plural $R^{22E}$ or $R^{23E}$, each $R^{22E}$ or $R^{23E}$ may be the same or different, or when $R^{22E}$ and $R^{23E}$ are both $C_{1-6}$ alkyl, they may be combined with the nitrogen atom to which they are each attached to form 3- to 6-membered nitrogen-containing saturated heterocycle;

$R^3$ and $R^4$ are each independently hydrogen atom, hydroxy, or fluorine atom, or $R^3$ and $R^4$ may be combined together to form $═O$ or $═CR^{5A}R^{6A}$;

$R^{18}$ is $—CF_3$ or cyano;

provided that when both of $R^1$ and $R^2$ are hydrogen atom, then $R^3$ and $R^4$ are $═CR^{5A}R^{6A}$.

(Item 14)

The compound of any one of Items 1 to 13 or a pharmaceutically acceptable salt thereof, wherein a and c are 1, and b and d are 1 or 2.

(Item 15)

The compound of any one of Items 1 to 14 or a pharmaceutically acceptable salt thereof, wherein a, b, c, and d are 1.

(Item 16)

The compound of any one of Items 1 to 14 or a pharmaceutically acceptable salt thereof, wherein a and c are 1, and b and d are 2.

(Item 17)

The compound of any one of Items 1 to 16 or a pharmaceutically acceptable salt thereof, wherein M is, each independently if there are plural, $C_{1-3}$ alkylene which may be independently substituted with the same or different 1 to 3 substituents selected from the group consisting of fluorine atom, $C_{2-4}$ alkynyl, $C_{1-3}$ alkoxy, $—NR^{22A}R^{23A}$, and cyano.

(Item 18)

The compound of any one of Items 1 to 17 or a pharmaceutically acceptable salt thereof, wherein M is, each independently if there are plural, $C_{1-3}$ alkylene.

(Item 19)

The compound of any one of Items 1 to 18 or a pharmaceutically acceptable salt thereof, wherein Q is, each independently if there are plural, $C_{3-6}$ cycloalkyl, 3- to 6-membered saturated heterocyclyl, phenyl, or 5- to 6-membered heteroaryl, wherein the cycloalkyl, the saturated heterocyclyl, the phenyl, and the heteroaryl may be independently substituted with the same or different 1 to 5 substituents selected from the group consisting of fluorine atom, chlorine atom, bromine atom, $C_{1-3}$ alkyl, $C_{2-4}$ alkynyl, $C_{1-3}$ alkoxy, $—CONR^{22C}R^{23C}$, $—NR^{22C}R^{23C}$, $—NR^{22C}COR^{21C}$, $—NR^{22C}SO_2R^{21C}$, $—SO_2R^{21C}$, $—SO_2NR^{22C}R^{23C}$, and cyano.

(Item 20)

The compound of any one of Items 1 to 19 or a pharmaceutically acceptable salt thereof, wherein Q is, each independently if there are plural, $C_{3-6}$ cycloalkyl, 3- to 6-membered saturated heterocyclyl, phenyl, or 5- to 6-membered heteroaryl, wherein the cycloalkyl, the saturated heterocyclyl, the phenyl, and the heteroaryl may be independently substituted with the same or different 1 to 5 substituents selected from the group consisting of fluorine atom, $C_{1-3}$ alkyl, $—NR^{22C}SO_2R^{21C}$, $—SO_2NR^{22C}R^{23C}$, and cyano.

(Item 21)

The compound of any one of Items 1 to 20 or a pharmaceutically acceptable salt thereof, wherein Q is, each independently if there are plural, $C_{3-6}$ cycloalkyl which may be independently substituted with the same or different 1 to 2 substituents selected from the group consisting of fluorine atom, $C_{1-3}$ alkyl, $—NR^{22C}SO_2R^{21C}$, $—SO_2NR^{22C}R^{23C}$, and cyano.

(Item 22)

The compound of any one of Items 1 to 21 or a pharmaceutically acceptable salt thereof, wherein $R^{5A}$ and $R^{6A}$ are each independently hydrogen atom, $C_{1-3}$ alkyl or $C_{3-6}$ cycloalkyl, wherein the alkyl may be each independently substituted with the same or different 1 to 2 substituents selected from the group consisting of fluorine atom, $—NR^{22E}SO_2R^{21E}$, $—SO_2NR^{22E}R^{23E}$, and cyano; and the cycloalkyl may be each independently substituted with the same or different 1 to 2 substituents selected from the group consisting of fluorine atom, $C_{1-3}$ alkyl, $—NR^{22E}SO_2R^{21E}$, $—SO_2NR^{22}R^{23}$, and cyano, and if there are plural $R^{5A}$ or $R^{6A}$, each $R^{5A}$ or $R^{6A}$ may be the same or different, or when $R^{5A}$ and $R^{6A}$ are both $C_{1-3}$ alkyl, they may be combined with the carbon atom to which they are each attached to form 3- to 6-membered saturated carbocycle.

(Item 23)

The compound of any one of Items 1 to 22 or a pharmaceutically acceptable salt thereof, wherein $R^{5A}$ and $R^{6A}$ are each independently hydrogen atom or $C_{3-6}$ cycloalkyl which may be each independently substituted with the same or different 1 to 2 substituents selected from the group consisting of fluorine atom, $C_{1-3}$ alkyl, $—NR^{22E}SO_2R^{21E}$, $—SO_2NR^{22E}R^{23E}$, and cyano, and if there are plural $R^{5A}$ or $R^{6A}$, each $R^{5A}$ or $R^{6A}$ may be the same or different.

(Item 24)

The compound of Item 1 or a pharmaceutically acceptable salt thereof, wherein formula (1) is the following formula (1b):

(1b)

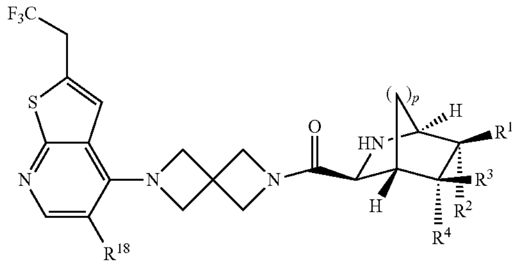

wherein

- p is 1 or 2;
- $R^1$ and $R^2$ are independently hydrogen atom or -M-Q; or $R^1$ and $R^2$ may be combined together to form $=CR^{5A}R^{6A}$;
- M is, each independently if there are plural, $C_{1-3}$ alkylene;
- Q is, each independently if there are plural, $C_{3-6}$ cycloalkyl which may be independently substituted with the same or different 1 to 2 substituents selected from the group consisting of fluorine atom, $C_{1-3}$ alkyl, $—NR^{22C}SO_2R^{21C}$, $—SO_2NR^{22C}R^{23C}$, and cyano;
- $R^{5A}$ and $R^{6A}$ are each independently hydrogen atom or $C_{3-6}$ cycloalkyl which may be independently substituted with the same or different 1 to 2 substituents selected from the group consisting of fluorine atom, $C_{1-3}$ alkyl, $—NR^{22E}SO_2R^{21E}$, $—SO_2NR^{22E}R^{23E}$, and cyano, and if there are plural $R^{5A}$ or $R^{6A}$, each $R^{5A}$ or $R^{6A}$ may be the same or different;
- $R^{21C}$ is, each independently if there are plural, $C_{1-6}$ alkyl;
- $R^{22C}$ and $R^{23C}$ are each independently hydrogen atom or $C_{1-6}$ alkyl, and if there are plural $R^{22C}$ or $R^{23C}$, each $R^{22C}$ or $R^{23C}$ may be the same or different, or when $R^{22C}$ and $R^{230}$ are both $C_{1-6}$ alkyl, they may be combined with the nitrogen atom to which they are attached to form 3- to 8-membered nitrogen-containing saturated heterocycle;
- $R^{21E}$ is, each independently if there are plural, $C_{1-6}$ alkyl;
- $R^{22E}$ and $R^{23E}$ are each independently hydrogen atom or $C_{1-6}$ alkyl, and if there are plural $R^{22E}$ or $R^{23E}$, each $R^{22E}$ or $R^{23E}$ may be the same or different, or when $R^{22E}$ and $R^{23E}$ are both $C_{1-6}$ alkyl, they may be combined with the nitrogen atom to which they are each attached to form 3- to 6-membered nitrogen-containing saturated heterocycle;
- $R^3$ and $R^4$ are each independently hydrogen atom or fluorine atom, or $R^3$ and $R^4$ may be combined together to form $=O$ or $=CR^{5A}R^{6A}$;
- $R^{18}$ is $—CF_3$ or cyano;
- provided that when both of $R^1$ and $R^2$ are hydrogen atom, then $R^3$ and $R^4$ are $=CR^{5A}R^{6A}$.

(Item 25)

The compound of Item 1 or a pharmaceutically acceptable salt thereof, wherein formula (1) is the following formula (1c):

(1c)

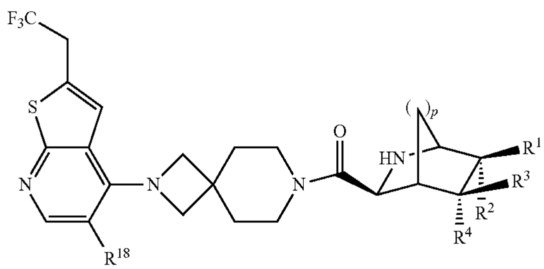

wherein

- p is 1 or 2;
- $R^1$ and $R^2$ are independently hydrogen atom or -M-Q; or $R^1$ and $R^2$ may be combined together to form $=CR^{5A}R^{6A}$;
- M is, each independently if there are plural, $C_{1-3}$ alkylene;
- Q is, each independently if there are plural, $C_{3-6}$ cycloalkyl which may be independently substituted with the same or different 1 to 2 substituents selected from the group consisting of fluorine atom, $C_{1-3}$ alkyl, $—NR^{22C}SO_2R^{21C}$, $—SO_2NR^{22C}R^{23C}$, and cyano;
- $R^{5A}$ and $R^{6A}$ are each independently hydrogen atom or $C_{3-6}$ cycloalkyl which may be independently substituted with the same or different 1 to 2 substituents selected from the group consisting of fluorine atom, $C_{1-3}$ alkyl, $—NR^{22E}SO_2R^{21E}$, $—SO_2NR^{22E}R^{23E}$, and cyano, and if there are plural $R^{5A}$ or $R^{6A}$, each $R^{5A}$ or $R^{6A}$ may be the same or different;
- $R^{21C}$ is, each independently if there are plural, $C_{1-6}$ alkyl;
- $R^{22C}$ and $R^{23C}$ are each independently hydrogen atom or $C_{1-6}$ alkyl, and if there are plural $R^{22C}$ or $R^{23C}$, each $R^{22C}$ or $R^{23C}$ may be the same or different, or when $R^{22C}$ and $R^{23C}$ are both $C_{1-6}$ alkyl, they may be combined with the nitrogen atom to which they are attached to form 3- to 8-membered nitrogen-containing saturated heterocycle;
- $R^{21E}$ is, each independently if there are plural, $C_{1-6}$ alkyl;
- $R^{22E}$ and $R^{23E}$ are each independently hydrogen atom or $C_{1-6}$ alkyl, and if there are plural $R^{22E}$ or $R^{23E}$, each $R^{22E}$ or $R^{23E}$ may be the same or different, or when $R^{22E}$ and $R^{23E}$ are both $C_{1-6}$ alkyl, they may be combined with the nitrogen atom to which they are each attached to form 3- to 6-membered nitrogen-containing saturated heterocycle;
- $R^3$ and $R^4$ are each independently hydrogen atom or fluorine atom, or $R^3$ and $R^4$ may be combined together to form $=O$ or $=CR^{5A}R^{6A}$;
- $R^{18}$ is $—CF_3$ or cyano;
- provided that when both of $R^1$ and $R^2$ are hydrogen atom, then $R^3$ and $R^4$ are $=CR^{5A}R^{6A}$.

(Item 26)

The compound of any one of Items 1 to 25 or a pharmaceutically acceptable salt thereof, wherein $R^1$ and $R^2$ are each independently hydrogen atom or -M-Q.

(Item 27)

The compound of any one of Items 1 to 26 or a pharmaceutically acceptable salt thereof, wherein M is methylene.

(Item 28)

The compound of any one of Items 1 to 27 or a pharmaceutically acceptable salt thereof, wherein Q is, each independently if there are plural, $C_{3-6}$ cycloalkyl.

(Item 29)

The compound of any one of Items 1 to 28 or a pharmaceutically acceptable salt thereof, wherein $R^{5A}$ and $R^{6A}$ are each independently hydrogen atom or $C_{3-6}$ cycloalkyl, and if there are plural $R^{5A}$ or $R^{6A}$, each $R^{5A}$ or $R^{6A}$ may be the same or different.

(Item 30)

The compound of any one of Items 1 to 29 or a pharmaceutically acceptable salt thereof, wherein $R^{5A}$ and $R^{6A}$ are hydrogen atom.

(Item 31)

The compound of any one of Items 1 to 30 or a pharmaceutically acceptable salt thereof, wherein p is 1 or 2;

$R^1$ and $R^2$ are each independently hydrogen atom or -M-Q;

M is methylene;

Q is, each independently if there are plural, $C_{3-6}$ cycloalkyl;

$R^3$ and $R^4$ are each independently hydrogen atom or fluorine atom, or $R^3$ and $R^4$ may be combined together to form $=CH_2$;

$R^{18}$ is $-CF_3$ or cyano;

provided that when both of $R^1$ and $R^2$ are hydrogen atom, then $R^3$ and $R^4$ are $=CH_2$.

(Item 32)

The compound of any one of Items 1 to 28, and 31 or a pharmaceutically acceptable salt thereof, wherein $R^1$ is hydrogen atom, $R^2$ is -M-Q, M is methylene, Q is $C_{3-6}$ cycloalkyl, $R^3$ is hydrogen atom, $R^4$ is hydrogen atom or fluorine atom, and $R^{18}$ is $-CF_3$ or cyano.

(Item 33)

The compound of any one of Items 1 to 28, and 31 or a pharmaceutically acceptable salt thereof, wherein $R^1$ is -M-Q, $R^2$ is hydrogen atom, M is methylene, Q is $C_{3-6}$ cycloalkyl, $R^3$ is hydrogen atom or fluorine atom, $R^4$ is hydrogen atom, and $R^{18}$ is $-CF_3$ or cyano.

(Item 34)

The compound of any one of Items 1 to 26, and 29 to 31 or a pharmaceutically acceptable salt thereof, wherein $R^1$ and $R^2$ are hydrogen atom, $R^3$ and $R^4$ are combined together to form $=CH_2$, and $R^{18}$ is $-CF_3$ or cyano.

(Item 35)

The compound of any one of Items 1 to 34 or a pharmaceutically acceptable salt thereof, wherein p is 1.

(Item 36)

The compound of any one of Items 1 to 34 or a pharmaceutically acceptable salt thereof, wherein p is 2.

(Item 37)

The compound of Item 1 or a pharmaceutically acceptable salt thereof, selected from:

[(1S,3S,4R,6S)-6-(cyclopropylmethyl)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 1), 4-{6-[(1S,3S,4R,6S)-6-(cyclopropylmethyl)-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile (Example 2),

[(1S,3S,4R,6R)-6-(cyclopropylmethyl)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 3), 4-{6-[(1S,3S,4R,6R)-6-(cyclopropylmethyl)-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile (Example 4),

[(1S,3S,4R)-5-methylidene-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 5), 4-{6-[(1S,3S,4R)-5-methylidene-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile (Example 6),

[(1S,3S,4S,5R,6R)-6-(cyclopropylmethyl)-5-fluoro-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 11), 4-{6-[(1S,3S,4S,5R,6R)-6-(cyclopropylmethyl)-5-fluoro-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile (Example 12),

[(1S,3S,4S,5S,6S)-6-(cyclopropylmethyl)-5-fluoro-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 13), 4-{6-[(1S,3S,4S,5S,6S)-6-(cyclopropylmethyl)-5-fluoro-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile (Example 14),

[(1S,3S,4R)-5-($^2H_2$)methylidene-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 17),

[(1S,3S,4R)-5-($^2H_2$)methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 21),

[(1S,3S,4R,6S)-6-(cyclopropylmethyl)-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 22),

[(1S,3S,4R)-5-methylidene-2-azabicyclo[2.2.1]heptan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 23), 4-{7-[(1S,3S,4R)-5-($^2H_2$)methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile (Example 24), 4-{7-[(1S,3S,4R,6S)-6-(cyclopropylmethyl)-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile (Example 25), 4-{7-[(1S,3S,4R)-5-methylidene-2-azabicyclo[2.2.1]heptane-3-carbonyl]-2,7-diazaspiro[3.5]nonan-2-yl}-2-(2,2,2-trifluoroethyl)thieno[2,3-b]pyridine-5-carbonitrile (Example 26),

[(1S,3S,4R)-5-methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 27), and 4-{7-[(1S,3S,4R)-5-methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile (Example 28).

(Item 38)

The compound of Item 1 or a pharmaceutically acceptable salt thereof, selected from:

[(1S,3S,4R,6S)-6-(cyclopropylmethyl)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 1),

[(1S,3S,4S,5R,6R)-6-(cyclopropylmethyl)-5-fluoro-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 11), 4-{6-[(1S,3S,4S,5R,6R)-6-(cyclopropylmethyl)-5-fluoro-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile (Example 12),

[(1S,3S,4R)-5-($^2H_2$)methylidene-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 17),

[(1S,3S,4R)-5-($^2H_2$)methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 21),

[(1S,3S,4R,6S)-6-(cyclopropylmethyl)-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 22),

[(1S,3S,4R)-5-methylidene-2-azabicyclo[2.2.1]heptan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 23), 4-{7-[(1S,3S,4R)-5-($^2H_2$)methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile (Example 24), 4-{7-[(1S,3S,4R,6S)-6-(cyclopropylmethyl)-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile (Example 25), 4-{7-[(1S,3S,4R)-5-methylidene-2-azabicyclo[2.2.1]heptane-3-carbonyl]-2,7-diazaspiro[3.5]nonan-2-yl}-2-(2,2,2-trifluoroethyl)thieno[2,3-b]pyridine-5-carbonitrile (Example 26),

[(1S,3S,4R)-5-methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 27), and 4-{7-[(1S,3S,4R)-5-methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile (Example 28).

(Item 39)

The compound of Item 1 or a pharmaceutically acceptable salt thereof, selected from:

[(1S,3S,4R,6S)-6-(cyclopropylmethyl)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 1),

[(1S,3S,4S,5R,6R)-6-(cyclopropylmethyl)-5-fluoro-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 11), 4-{6-[(1S,3S,4S,5R,6R)-6-(cyclopropylmethyl)-5-fluoro-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile (Example 12),

[(1S,3S,4R,6S)-6-(cyclopropylmethyl)-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 22), and 4-{7-[(1S,3S,4R,6S)-6-(cyclopropylmethyl)-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile (Example 25).

(Item 40)

The compound of Item 1 or a pharmaceutically acceptable salt thereof, selected from:

[(1S,3S,4R)-5-($^2H_2$)methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 21), 4-{7-[(1S,3S,4R)-5-($^2H_2$)methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile (Example 24),

[(1S,3S,4R)-5-methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone (Example 27), and 4-{7-[(1S,3S,4R)-5-methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile (Example 28).

(Item 41)

A medicament comprising the compound of any one of Items 1 to 40 or a pharmaceutically acceptable salt thereof as an active ingredient.

(Item 42)

An antitumor medicament comprising the compound of any one of Items 1 to 40 or a pharmaceutically acceptable salt thereof as an active ingredient.

(Item 43)

The antitumor medicament of Items 42, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic lymphocytic leukemia, chronic myeloid leukemia, myelodysplastic syndrome, polycythemia vera, malignant lymphoma (including B-cell lymphoma), myeloma (including multiple myeloma), brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, or skin cancer.

(Item 44)

The antitumor medicament of Item 42 or 43, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic myeloid leukemia, malignant lymphoma (including B-cell lymphoma), myeloma (including multiple myeloma), brain tumor, prostate cancer, breast cancer, neuroblastoma, Ewing's sarcoma, or liver cancer.

(Item 45)

The antitumor medicament of any one of Items 42 to 44, wherein the tumor is MLL acute leukemia, MLL partial tandem duplicate acute leukemia, NPM mutated acute leukemia, MOZ acute leukemia, NUP98 acute leukemia, CALM acute leukemia, chronic myeloid leukemia, B-cell lymphoma, multiple myeloma, neuroblastoma, or prostate cancer.

(Item 46)

The antitumor medicament of any one of Items 42 to 45, wherein the tumor is MLL acute leukemia, MLL partial tandem duplicate acute leukemia, NPM mutated acute leukemia, MOZ acute leukemia, NUP98 acute leukemia, CALM acute leukemia, chronic myeloid leukemia, B-cell lymphoma, or multiple myeloma.

(Item 47)

The antitumor medicament of any one of Items 42 to 46, wherein the tumor is MLL acute leukemia, or NPM mutated acute leukemia.

(Item 48)

The antitumor medicament of any one of Items 42 to 47, wherein the tumor is accompanied by high expression of HOXa gene cluster, or MEIS gene cluster.

(Item 49)

The antitumor medicament of any one of Items 42 to 48, wherein the tumor is accompanied by p53 gain-of-function mutation.

(Item 50)

A method for treating a tumor comprising administrating the compound of any one of Items 1 to 40 or a pharmaceutically acceptable salt thereof to a patient in need thereof.

(Item 51)

The method of Item 50, wherein the tumor is involved in menin-MLL.

(Item 52)

Use of the compound of any one of Items 1 to 40 or a pharmaceutically acceptable salt thereof in the manufacture of an antitumor medicament.

(Item 53)

The compound of any one of Items 1 to 40 or a pharmaceutically acceptable salt thereof for use in the treatment of a tumor.

(Item 54)

A pharmaceutical composition comprising the compound of any one of Items 1 to 40 or a pharmaceutically acceptable salt thereof in combination with at least one different agent or a pharmaceutically acceptable salt thereof, wherein the different agent is at least one agent selected from the group consisting of an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, an biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

(Item 55)

The compound of any one of Items 1 to 40 or a pharmaceutically acceptable salt thereof for treating a tumor, which is used in combination with at least one different agent or a pharmaceutically acceptable salt thereof, wherein the different agent is at least one agent selected from an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

Effect of the Invention

The present invention provides an inhibitor of the binding between menin and MLL fusion protein, comprising an optically-active bridged piperidine derivative or a pharmaceutically acceptable salt thereof. The compound of the present invention is useful as a medicament for diseases involved in the binding between menin and MLL, and is applicable to a patient suffering from, specifically, MLL acute leukemia, NPM mutated acute leukemia, prostate cancer, breast cancer, Ewing's sarcoma, liver cancer, p53 gain-of-function mutated cancer, and the like.

DESCRIPTION OF EMBODIMENTS

Hereinafter, terms used herein are explained as follows.

The "halogen atom" includes, for example, fluorine atom, chlorine atom, bromine atom, and iodine atom, and the like. It is preferably fluorine atom.

The "$C_{1-6}$ alkyl" means alkyl having 1 to 6 carbon atoms, and "$C_6$ alkyl" means alkyl having 6 carbon atoms. The same is applied to the case of the other carbon numbers.

The "$C_{1-6}$ alkyl" means straight or branched chain saturated hydrocarbon group having 1 to 6 carbon atoms. The $C_{1-6}$ alkyl includes preferably "$C_{1-4}$ alkyl", more preferably "$C_{1-3}$ alkyl". The "$C_{1-3}$ alkyl" includes, for example, methyl, ethyl, propyl, 1-methylethyl, and the like. The "$C_{1-4}$ alkyl" includes, for example, butyl, 1,1-dimethylethyl, 1-methylpropyl, 2-methylpropyl, and the like, besides the examples listed in the said "$C_{1-3}$ alkyl". The "$C_{1-6}$ alkyl" includes, for example, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, hexyl, and the like, besides the examples listed in the said "$C_{1-4}$ alkyl".

The "$C_{2-6}$ alkenyl" means straight or branched chain unsaturated hydrocarbon group having 2 to 6 carbon atoms and 1 to 3 double bonds. The "$C_{2-6}$ alkenyl" includes preferably "$C_{2-4}$ alkenyl". The "$C_{2-4}$ alkenyl" includes, for example, vinyl, propenyl, methylpropenyl, butenyl, and the like. The "$C_{2-6}$ alkenyl" includes, for example, pentenyl, hexenyl, and the like, besides the examples listed in the said "$C_{2-4}$ alkenyl".

The "$C_{2-6}$ alkynyl" means straight or branched chain unsaturated hydrocarbon group having 2 to 6 carbon atoms and a triple bond. The "$C_{2-6}$ alkynyl" includes preferably "$C_{2-4}$ alkynyl". The "$C_{2-4}$ alkynyl" includes, for example, propynyl, methylpropynyl, butynyl, and the like. The "$C_{2-6}$ alkynyl" includes, for example, methylbutynyl, pentynyl, hexynyl, and the like, besides the examples listed in the said "$C_{2-4}$ alkynyl".

The "$C_{1-6}$ alkoxy" means "$C_{1-6}$ alkyloxy", and the part "$C_1$-6 alkyl" is as defined in the said "$C_{1-6}$ alkyl". The "$C_{1-6}$ alkoxy" includes preferably "$C_{1-4}$ alkoxy", more preferably "$C_{1-3}$ alkoxy". The "$C_{1-3}$ alkoxy" includes, for example, methoxy, ethoxy, propoxy, 1-methylethoxy, and the like. The "$C_{1-4}$ alkoxy" includes, for example, butoxy, 1,1-dimethylethoxy, 1-methylpropoxy, 2-methylpropoxy, and the like, besides the examples listed in the said "$C_{1-3}$ alkyl". The "$C_{1-6}$ alkoxy" includes, for example, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, hexyloxy, and the like, besides the examples listed in the said "$C_{1-4}$ alkyl".

The "$C_{1-6}$ alkylene" means divalent straight or branched chain saturated hydrocarbon group having 1 to 6 carbon atoms. The "$C_{1-6}$ alkylene" includes preferably "$C_{1-4}$ alkylene", more preferably "$C_{1-3}$ alkylene". The "$C_{1-3}$ alkylene" includes, for example, methylene, ethylene, propylene, 1-methylethylene, and the like. The "$C_{1-4}$ alkylene" includes, for example, butylene, 1,1-dimethylethylene, 1-methylpropylene, 2-methylpropylene, and the like, besides the examples listed in the said "$C_{1-3}$ alkylene". The "$C_{1-6}$ alkylene" includes, for example, pentylene, 1,1-dimethylpropylene, 1,2-dimethylpropylene, 1-methylbutylene, 2-methylbutylene, 4-methylpentylene, 3-methylpentylene, 2-methylpentylene, 1-methylpentylene, hexylene, and the like, besides the examples listed in the said "$C_{1-4}$ alkylene".

The "$C_{2-6}$ alkenylene" means divalent straight or branched chain unsaturated hydrocarbon group having 2 to 6 carbon atoms and 1 to 3 double bonds. The "$C_{2-6}$ alkenylene" includes preferably "$C_{2-4}$ alkenylene". The "$C_{2-4}$ alkenylene" includes, for example, vinylene, propenylene, methylpropenylene, butenylene, and the like. The "$C_{2-6}$ alkenylene" includes, for example, pentenylene, hexenylene, and the like, besides the examples listed in the said "$C_{2-4}$ alkenyl".

The "$C_{2-6}$ alkynylene" means divalent straight or branched chain unsaturated hydrocarbon group having 2 to 6 carbon atoms and 1 to 3 triple bonds. The "$C_{2-6}$ alkynylene" includes preferably "$C_{2-4}$ alkynylene". The "$C_{2-4}$ alkynylene" includes, for example, ethynylene, 1-butynylene, 2-pentynylene and the like. The "$C_{2-6}$ alkynylene" includes, for example, 2-pentynylene, and the like, besides the examples listed in the said "$C_{2-4}$ alkynylene".

The "$C_{3-10}$ cycloalkyl" means cyclic saturated hydrocarbon group having 3 to 10 carbon atoms, which may have a partially-unsaturated bond or a bridged structure.

The "$C_{3-10}$ cycloalkyl" includes preferably "$C_{3-7}$ cycloalkyl", more preferably "$C_{3-6}$ cycloalkyl". The "$C_{3-6}$ cycloalkyl" includes, for example, cyclopropyl, cyclobutyl, cyclopentyl, cyclohexyl, and the like. The "$C_{3-7}$ cycloalkyl" includes, for example, cycloheptyl, besides the examples listed in the said "$C_{3-6}$ cycloalkyl". The "$C_{3-10}$ cycloalkyl" includes, for example, cyclooctyl, cyclononyl, cyclodecyl, adamantyl, and the like, besides the examples listed in the said "$C_{3-7}$ cycloalkyl".

The "$C_{3-10}$ cycloalkyl" also encompasses a fused ring with an aromatic hydrocarbon ring. The fused ring compounds includes, for example, the following structures:

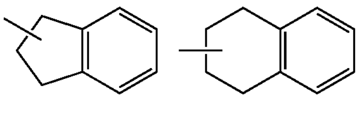

The "$C_{3-10}$ cycloalkylene" means divalent cyclic saturated hydrocarbon group having 3 to 10 carbon atoms, which may have a partially-unsaturated bond or a bridged structure. The "$C_{3-10}$ cycloalkylene" includes preferably "$C_{3-7}$ cycloalkylene". The "$C_{3-7}$ cycloalkylene" includes, for example, cyclopropylene, cyclobutylene, cyclopentylene, cyclohexylene, cycloheptylene, and the like. The "$C_{3-10}$ cycloalkylene" includes, for example, cyclooctylene, cyclononylene, cyclodecylene, adamantylene, and the like, besides the examples listed in the said "$C_{3-7}$ cycloalkylene".

The "3- to 8-membered saturated carbocycle" means cyclic saturated hydrocarbon group having 3 to 8 carbon atoms. The "3- to 8-membered saturated carbocycle" includes preferably "4- to 6-membered saturated carbocycle". The "4- to 6-membered saturated carbocycle" includes, for example, cyclobutane ring, cyclopentane ring, cyclohexane ring, and the like. The "3- to 8-membered saturated carbocycle" includes, for example, cyclopropane ring, cycloheptane ring, cyclooctane ring, and the like, besides the examples listed in the said "4- to 6-membered saturated carbocycle".

The "3- to 10-membered saturated heterocyclyl" means monovalent or divalent saturated heterocycle consisting of 1 to 2 atoms selected independently from the group consisting of nitrogen atom, oxygen atom and sulfur atom, and 2 to 9 carbon atoms, which may have a partially-unsaturated bond and a bridged structure. The atoms of which the ring consists may include oxidized atoms such as —C(O)—, —S(O)—, and —$SO_2$—. The "3- to 10-membered saturated heterocyclyl" is preferably "4- to 7-membered monocyclic saturated heterocyclyl", more preferably "5- or 6-membered monocyclic saturated heterocyclyl". The "5- or 6-membered monocyclic saturated heterocyclyl" includes, for example, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, oxoimidazolidinyl, dioxoimidazolidinyl, oxooxazolidinyl, dioxooxazolidinyl, dioxothiazolidinyl, tetrahydrofuranyl, tetrahydropyranyl, tetrahydrofurylene, pyrrolidinylene, imidazolidinylene, piperidinylene, morpholinylene, thiomorpholinylene, dioxothiomorpholinylene, hexamethyleneiminylene, oxazolidinylene, thiazolidinylene, oxoimidazolidinylene, dioxoimidazolidinylene, dioxooxazolidinylene, oxooxazolidinylene, tetrahydrofuranylene, dioxothiazolidinylene, tetrahydropyranylene, and the like. The "4- to 7-membered monocyclic saturated heterocyclyl" includes, for example, oxetanyl, azetidinyl, oxetanylene, azetidinylene, and the like, besides the examples listed in the said "5- or 6-membered monocyclic saturated heterocyclyl". The "3- to 10-membered saturated heterocyclyl" includes, for example, oxiranyl, aziridinyl, oxiranylene, aziridinylene, and the like, besides the examples listed in the said "4- to 7-membered monocyclic saturated heterocyclyl".

The "3- to 10-membered saturated heterocyclyl" also encompasses bicyclic compounds, i.e., "3- to 10-membered saturated heterocyclyl" fused with a 6-membered aromatic hydrocarbon ring or a 6-membered aromatic heterocycle. The 6-membered aromatic hydrocarbon ring in the fused ring includes benzene ring and the like. The 6-membered aromatic heterocycle in the fused ring includes pyridine, pyrimidine, pyridazine, and the like. The bicyclic "3- to 10-membered saturated heterocyclyl" which is a fused bicyclyl includes dihydroindolyl, dihydroisoindolyl, dihydropurinyl, dihydrothiazolopyrimidinyl, dihydrobenzodioxanyl, isoindolyl, indazolyl, tetrahydroquinolinyl, tetrahydroisoquinolinyl, tetrahydronaphthyridinyl, dihydroindolylene, dihydroisoindolylene, dihydropurinylene, dihydrobenzodioxanylene, dihydrothiazolopyrimidinylene, isoindolylene, indazolylene, tetrahydroquinolinylene, tetrahydroisoquinolinylene, tetrahydronaphthyridinylene, and the like.

The "3- to 8-membered nitrogen-containing saturated heterocycle" means a saturated heterocycle which consists of a nitrogen atom and 2 to 7 carbon atoms. The "3- to 8-membered nitrogen-containing saturated heterocycle" includes preferably "3- to 6-membered nitrogen-containing saturated heterocycle", more preferably "4- to 6-membered nitrogen-containing saturated heterocycle". The "4- to 6-membered nitrogen-containing saturated heterocycle" includes, for example, azetidine ring, pyrrolidine ring, piperidine ring, and the like. The "3- to 6-membered nitrogen-containing saturated heterocycle" includes, for example, aziridine ring, and the like, besides the examples listed in the said "4- to 6-membered nitrogen-containing saturated heterocycle". The "3- to 8-membered nitrogen-containing saturated heterocycle" includes, for example, azepane ring, azocane ring, and the like, besides the examples listed in the said "3- to 6-membered nitrogen-containing saturated heterocycle".

The "$C_{6-10}$ aryl" means aromatic hydrocarbon ring having 6 to 10 carbon atoms. The "$C_{6-10}$ aryl" includes, for example, phenyl, 1-naphthyl, 2-naphthyl, and the like. It includes preferably phenyl.

The "$C_{6-10}$ aryl" also encompasses bicyclic compounds, i.e., $C_{6-10}$ aryl fused with $C_{4-6}$ cycloalkyl or 5- or 6-membered saturated heterocycle. The bicyclic "$C_{6-10}$ aryl" which is a fused bicyclyl includes, for example, the following groups:

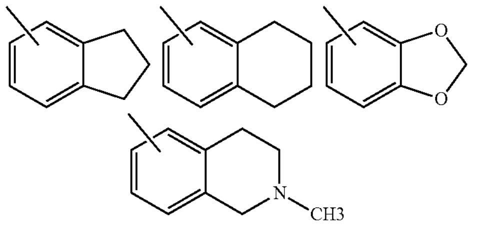

The "$C_{6-10}$ arylene" means divalent aromatic hydrocarbon group having 6 to 10 carbon atoms. The "$C_{6-10}$ arylene" includes, for example, phenylene, 1-naphthylene, 2-naphthylene, and the like. It includes preferably phenylene.

The "aromatic hydrocarbon ring" means a cyclic part of the said "$C_{6-10}$ aryl" and the said "$C_{6-10}$ arylene".

The "5- to 12-membered heteroaryl" means monocyclic 5- to 7-membered aromatic heterocyclyl or bicyclic 8- to 12-membered aromatic heterocyclyl having 1 to 4 atoms selected independently from the group consisting of nitrogen atom, oxygen atom and sulfur atom. It is preferably "5- to 7-membered monocyclic heteroaryl". It is more preferably pyridyl, pyrimidinyl, quinolyl, or isoquinolyl. It is even more preferably pyridyl. The "5- to 7-membered monocyclic heteroaryl" includes, for example, pyridyl, pyridazinyl, isothiazolyl, pyrrolyl, furyl, thienyl, thiazolyl, imidazolyl, pyrimidinyl, thiadiazolyl, pyrazolyl, oxazolyl, isoxazolyl, pyrazinyl, triazinyl, triazolyl, oxadiazolyl, triazolyl, tetrazolyl, and the like. The "5- to 12-membered heteroaryl" includes indolyl, indazolyl, chromenyl, quinolyl, isoquinolyl, benzofuranyl, benzothienyl, benzooxazolyl, benzothiazolyl, benzoisoxazolyl, benzoisothiazolyl, benzotriazolyl, benzoimidazolyl, and the like, besides the examples listed in the said "5- to 7-membered monocyclic heteroaryl".

The "5- to 12-membered heteroarylene" means divalent monocyclic 5- to 7-membered aromatic heterocyclic group or divalent bicyclic 8- to 12-membered aromatic heterocyclic group having 1 to 4 atoms selected independently from the group consisting of nitrogen atom, oxygen atom and sulfur atom. It is preferably "5- to 7-membered monocyclic heteroarylene". It is more preferably pyridylene, pyrimidylene, quinolylene, or isoquinolylene. It is even more preferably pyridylene. The "5- to 7-membered monocyclic heteroarylene" includes, for example, pyridylene, pyridazinylene, isothiazolylene, pyrrolylene, furylene, thienylene, thiazolylene, imidazolylene, pyrimidinylene, thiadiazolylene, pyrazolylene, oxazolylene, isooxazolylene, pyrazinilene, triazinylene, triazolylene, oxadiazolylene, triazolylene, tetrazolylene, and the like. The "5- to 12-membered heteroarylene" includes indolylene, indazolylene, chromenylene, quinolylene, isoquinolylene, benzofuranylene, benzothienylene, benzooxazolylene, benzothiazolylene, benzoisooxazolylene, benzoisothiazolylene, benzotriazolylene, benzoimidazolylene, and the like, besides the examples listed in the said "5- to 7-membered monocyclic heteroarylene".

The "aromatic heterocyclic group" means a cyclic part of the said "5- to 12-membered heteroaryl" and the said "5- to 12-membered heteroarylene".

In the present specification, a bond across a ring group as showed in the following formula (W) means that the bond is attached to a substitutable position of the "group". For example, in the case of the following formula (W):

(W)

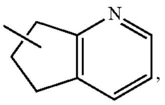

it represents the following formula (W-1), (W-2), or (W-3):

(W-1)

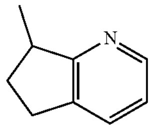

(W-2)

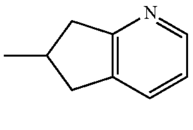

(W-3)

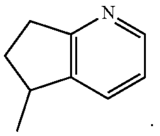

In the present specification, the stereochemistry of substituents in the compound of formula (1) or the example compounds can be illustrated, for example, as follows:

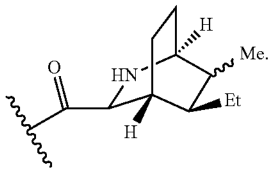 [SMILES: *C(=O)C1N[C@H]2CC[C@@H]1[C@H](CC)C2C]

In the above structure, the bonds shown as wedged line represent substituents in front of the page; the bond shown as dashed line represents a substituent in back of the page; and the bond shown as wavy line represents that the substituent exists in front and back of the page in an certain ratio, and when a bond which extends from the ring outside is shown as linear line, it represents that the bond exists either in front or back of the page.

The "cancer" or "tumor" means malignant neoplasm, which encompasses carcinoma, sarcoma, and hematologic malignancy. The "cancer" and "tumor" include, for example, acute leukemia (including MLL acute leukemia, MLL partial tandem duplicate acute leukemia, NPM mutated acute leukemia, MOZ acute leukemia, NUP98 acute leukemia, and CALM acute leukemia), chronic lymphocytic leukemia, chronic myeloid leukemia, myelodysplastic syndrome, polycythemia vera, malignant lymphoma (including B-cell lymphoma), myeloma (including multiple myeloma), brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, skin cancer, and the like. The above tumors may be accompanied by increased expression or mutation of specific genes. The tumors accompanied by increased expression of genes include, for example, tumors accompanied by high expression of HOXa gene cluster, tumors accompanied by high expression of MEIS gene cluster, and the like. The tumors accompanied by mutation of genes include tumors accompanied by p53 gain-of-function mutation and the like.

In the present compound of formula (1), preferred p, x, Y, Z, M, Q, a, b, c, d, e, f, g, h, i, j, k, l, U, $R^1$, $R^2$, $R^3$, $R^4$, $R^{5A}$, $R^{5B}$, $R^{6A}$, $R^{6B}$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21A}$, $R^{21B}$, $R^{21C}$, $R^{21D}$, $R^{21E}$, $R^{22A}$, $R^{22B}$, $R^{22C}$, $R^{22D}$, $R^{22E}$, $R^{23A}$, $R^{23B}$, $R^{23C}$, $R^{23D}$, and $R^{23E}$ are as follows, but the technical scope of the present invention is not limited to the scope of compounds listed below.

In an embodiment, p includes 1. In another embodiment, p includes 2.

X is preferably —C(O)—.

Y is preferably (Y-2).

Z is preferably (Z-1).

M includes preferably $C_{1-3}$ alkylene optionally substituted with the same or different 1 to 3 substituents selected from the group consisting of fluorine atom, $C_{2-4}$ alkynyl, $C_{1-3}$ alkoxy, —$NR^{22A}R^{23A}$, and cyano. It includes more preferably $C_{1-3}$ alkylene. It includes even more preferably methylene.

Q includes preferably $C_{3-6}$ cycloalkyl optionally-substituted with the same or different 1 to 5 substituents selected from the group consisting of fluorine atom, $C_{1-3}$ alkyl, —$NR^{22C}SO_2R^{21C}$, —$SO_2NR^{22C}R^{23C}$, and cyano; 3- to 6-membered saturated heterocyclyl optionally-substituted with the same or different 1 to 5 substituents selected from the group consisting of fluorine atom, $C_{1-3}$ alkyl, —$NR^{22C}SO_2R^{21C}$, —$SO_2NR^{22C}R^{23C}$, and cyano; phenyl optionally-substituted with the same or different 1 to 5 substituents selected from the group consisting of fluorine atom, $C_{1-3}$ alkyl, —$NR^{22C}SO_2R^{21C}$, —$SO_2NR^{22C}R^{23C}$, and cyano; and 5- to 6-membered heteroaryl optionally-substituted with the same or different 1 to 5 substituents selected from the group consisting of fluorine atom, $C_{1-3}$ alkyl, —$NR^{22C}SO_2R^{21C}$, —$SO_2NR^{22C}R^{23C}$, and cyano. It includes more preferably $C_{3-6}$ cycloalkyl optionally-substituted with the same or different 1 to 2 substituents selected from the group consisting of fluorine atom, $C_{1-3}$ alkyl, —$NR^{22C}SO_2R^{21C}$, —$SO_2NR^{22C}R^{23C}$, and cyano. It includes even more preferably $C_{3-6}$ cycloalkyl.

The symbols a and c include preferably 1.

The symbols b and d include preferably 1 or 2. More preferably, both of b and d are 1, or both are 2.

The symbols e, f, g, and h include preferably 0 or 1.

The symbols i, j, k, and l include preferably 1, 2, or 3.

U is preferably $CR^{18}$.

$R^1$ includes preferably hydrogen atom or -M-Q. It is more preferably -M-Q.

$R^2$ includes preferably hydrogen atom or -M-Q. It is more preferably hydrogen atom.

$R^3$ includes preferably hydrogen atom or fluorine atom. It is more preferably fluorine atom.

$R^4$ includes preferably hydrogen atom or fluorine atom. It is more preferably hydrogen atom.

In another embodiment, $R^3$ and $R^4$ are combined together to form =O or =$CR^{5A}R^{6A}$. It is more preferably =$CH_2$.

In another embodiment of $R^1$, $R^2$, $R^3$, and $R^4$, $R^1$ is hydrogen atom, $R^2$ is -M-Q, $R^3$ is hydrogen atom, and $R^4$ is hydrogen atom or fluorine atom.

In another embodiment of $R^1$, $R^2$, $R^3$, and $R^4$, $R^1$ is -M-Q, $R^2$ is hydrogen atom, $R^3$ is hydrogen atom or fluorine atom, and $R^4$ is hydrogen atom.

In another embodiment of $R^1$, $R^2$, $R^3$, and $R^4$, $R^1$ and $R^2$ are both hydrogen atom, and $R^3$ and $R^4$ are combined together to form =$CH_2$.

$R^{5A}$ and $R^{6A}$ include preferably hydrogen atom, fluorine atom, and $C_{3-6}$ cycloalkyl which may be substituted with the same or different 1 to 2 substituents selected from the group consisting of $C_{1-3}$ alkyl, —$NR^{22E}SO_2R^{21E}$, —$SO_2NR^{22E}R^{23E}$, and cyano. They are more preferably hydrogen atom.

$R^{5B}$ and $R^{6B}$ include preferably hydrogen atom and $C_{3-6}$ cycloalkyl which may be substituted with the same or different 1 to 2 substituents selected from the group consisting of fluorine atom, $C_{1-3}$ alkyl, —$NR^{22E}SO_2R^{21E}$, —$SO_2NR^{22E}R^{23E}$, and cyano. They are more preferably hydrogen atom.

$R^7$, $R^{15}$, $R^{21A}$, $R^{21B}$, $R^{21C}$, $R^{21D}$, and $R^{21E}$ are preferably $C_{1-3}$ alkyl.

$R^8$, $R^9$, $R^{11}$, $R^{12}$, $R^{13}$, $R^{16}$, $R^{17}$, $R^{19}$, $R^{20}$, $R^{22A}$, $R^{22B}$, $R^{22C}$, $R^{22D}$, $R^{22E}$, $R^{23A}$, $R^{23B}$, $R^{23C}$, $R^{23D}$, and $R^{23E}$ include preferably hydrogen atom or $C_{1-3}$ alkyl.

$R^{10}$ is preferably hydrogen atom.

$R^{14}$ includes preferably hydrogen atom, —$OR^{15}$, —$NR^{16}R^{17}$, or $C_{1-3}$ alkyl. It is more preferably hydrogen atom.

$R^{18}$ includes preferably hydrogen atom, halogen atom, $C_{1-3}$ alkyl (wherein the alkyl may be substituted with the same or different 1 to 5 substituents selected from the group consisting of fluorine atom, —$OR^{19}$, and —$NR^{19}R^{20}$), —$CO_2R^{19}$, —$CONR^{19}R^{20}$, and cyano. It is more preferably —$CF_3$ or cyano.

In an embodiment, the present compound of formula (1) includes the following (A).

(A)

A Compound or pharmaceutically acceptable salt thereof, wherein formula (1) is formula (1b) or formula (1c);

p is 1 or 2;

$R^1$ and $R^2$ are each independently or $R^1$ and $R^2$ may be combined together to form =$CR^{5A}R^{6A}$;

M is, each independently if there are plural, $C_{1-3}$ alkylene;

Q is, each independently if there are plural, $C_{3-6}$ cycloalkyl which may be independently substituted with the same or different 1 to 2 substituents selected from the group consisting of fluorine atom, $C_{1-3}$ alkyl, —$NR^{22C}SO_2R^{21C}$, —$SO_2NR^{22C}R^{23C}$, and cyano;

$R^{5A}$ and $R^{6A}$ are each independently hydrogen atom or $C_{3-6}$ cycloalkyl which may be independently substituted with the same or different 1 to 2 substituents selected from the group consisting of fluorine atom, $C_{1-3}$ alkyl, —$NR^{22E}SO_2R^{21E}$, —$SO_2NR^{22E}R^{23E}$, and cyano;

$R^{21C}$ is, each independently if there are plural, $C_{1-6}$ alkyl;

$R^{22C}$ and $R^{23C}$ are each independently hydrogen atom or $C_{1-6}$ alkyl, and if there are plural $R^{22C}$ or $R^{23C}$, each $R^{22C}$ or $R^{23C}$ may be the same or different, or when $R^{22C}$ and $R^{23C}$ are both $C_{1-6}$ alkyl, they may be combined with the nitrogen atom to which they are attached to form 3- to 6-membered nitrogen-containing saturated heterocycle;

$R^{21E}$ is, each independently if there are plural, $C_{1-6}$ alkyl;

$R^{22E}$ and $R^{23E}$ are each independently hydrogen atom or $C_{1-6}$ alkyl, and if there are plural $R^{22E}$ or $R^{23E}$, each $R^{22E}$ or $R^{23E}$ may be the same or different, or when $R^{22E}$ and $R^{23E}$ are both $C_{1-6}$ alkyl, they may be combined with the nitrogen atom to which they are each attached to form 3- to 6-membered nitrogen-containing saturated heterocycle;

$R^3$ and $R^4$ are each independently hydrogen atom or fluorine atom, or $R^3$ and $R^4$ may be combined together to form =O or =$CR^{5A}R^{6A}$;

$R^{18}$ is —$CF_3$ or cyano;

provided that when both of $R^1$ and $R^2$ are hydrogen atom, then $R^3$ and $R^4$ are =$CR^{5A}R^{6A}$.

An embodiment of the present compound of formula (1) includes the following (B):

(B)

A Compound or pharmaceutically acceptable salt thereof, wherein formula (1) is formula (1b) or formula (1c), p is 1 or 2, $R^1$ and $R^2$ are each independently hydrogen atom or -M-Q, M is methylene, Q is, each independently if there are plural, $C_{3-6}$ cycloalkyl, $R^3$ and $R^4$ are each independently hydrogen atom or fluorine atom, or $R^3$ and $R^4$ may be combined together to form =$CH_2$, $R^{18}$ is —$CF_3$ or cyano, provided that when both of $R^1$ and $R^2$ are hydrogen atom, then $R^3$ and $R^4$ are =$CH_2$.

An embodiment of the present compound of formula (1) includes the following (C):

(C)

A Compound or pharmaceutically acceptable salt thereof, wherein formula (1) is formula (1b) or formula (1c), p is 1 or 2, $R^1$ is hydrogen atom, $R^2$ is -M-Q, M is methylene, Q is $C_{3-6}$ cycloalkyl, $R^3$ is hydrogen atom, $R^4$ is hydrogen atom or fluorine atom, and $R^{18}$ is —$CF_3$ or cyano.

An embodiment of the present compound of formula (1) includes the following (D):

(D)

A Compound or pharmaceutically acceptable salt thereof, wherein formula (1) is formula (1b) or formula (1c), p is 1 or 2, $R^1$ and $R^2$ are hydrogen atom, $R^3$ and $R^4$ are combined together to form =$CH_2$, and $R^{18}$ is —$CF_3$ or cyano.

An embodiment of the present compound of formula (1) includes the following (E):

(E)

A Compound or pharmaceutically acceptable salt thereof, wherein formula (1) is formula (1b) or formula (1c), p is 1 or 2, $R^1$ is -M-Q, $R^2$ is hydrogen atom, M is methylene, Q is $C_{3-6}$ cycloalkyl, $R^3$ is hydrogen atom or fluorine atom, $R^4$ is hydrogen atom, and $R^{18}$ is —$CF_3$ or cyano.

Hereinafter, the processes to prepare the compound of the present invention of formula (1) are exemplified along with examples, but the processes to prepare the compound of the present invention should not be limited to the examples. Compounds used in the following process may exist as their salts unless they affect reactions.

The compound of the present invention can be prepared from known compounds as starting materials, for example, by the following methods A, B, C, D, E, F, G, H, I, J, K, L, M, or similar methods thereto, or optionally in combination with synthetic methods well-known to a person skilled in the art. And, $R^1$, $R^2$, $R^3$, and $R^4$ in each step may be optionally transformed to a different substituent by substituent variation.

Preparation Process A

The compound of the present invention of formula (A1) can be prepared, for example, by the following process:

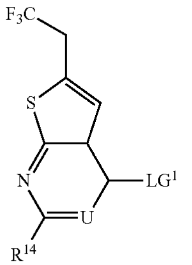

+

(a1)

-continued

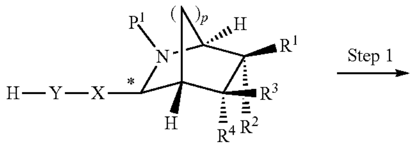

(a2)

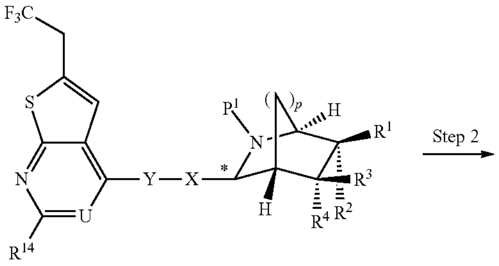

(a3)

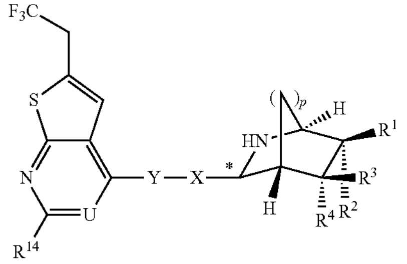

(A1)

wherein p, $R^1$, $R^2$, $R^3$, $R^4$, $R^{14}$, U, X, and Y are as defined in Item 1; $LG^1$ is a leaving group; and $P^1$ is an amino-protecting group, wherein $LG^1$ includes, for example, halogen atom, methanesulfonyloxy, p-toluenesulfonyloxy, trifluoromethanesulfonyloxy, phenoxy, trifluorophenoxy, tetrafluorophenoxy, pentafluorophenoxy, nitrophenoxy, and the like; $P^1$ includes, for example, amino-protecting groups described in Theodora W. Greene, and Peter G. M. Wuts, "*Protective Groups in Organic Synthesis*", John Wiley & Sons, Inc., (1999), and the like; and the stereochemistry of the carbon with * is not inverted during reactions.

(Step 1)

Compound (a3) can be prepared by reacting compound (a1) obtained in the following process with compound (a2) obtained in the following process in the presence or absence of an appropriate base in an appropriate solvent.

Compound (a1) used herein can be obtained by the following preparation process B (as compound (B1)), or by the following preparation process C (compound (C1)). Compound (a2) used herein can be obtained by the following preparation process D (as compound (D1)), or by the following preparation process E (compound (E1)).

The base used herein includes, for example, organic bases such as triethylamine, diisopropylethylamine, tributylamine, 1,5-diazabicyclo[4.3.0]non-5-ene (DBN), 1,8-diazabicyclo[5.4.0]undec-7-ene (DBU), pyridine, 4-(dimethylamino)pyridine, picoline, and N-methylmorpholine (NMM), and inorganic bases such as sodium bicarbonate, potassium bicarbonate, sodium carbonate, potassium carbonate, sodium hydroxide, and potassium hydroxide. The base includes preferably triethylamine, diisopropylethylamine, potassium carbonate, sodium hydroxide, and the like.

The solvent used herein includes, for example, alcohol solvents such as methanol, ethanol, 2-propanol (isopropyl alcohol), and tert-butanol; ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; ester solvents such as ethyl acetate, and methyl acetate; aprotic solvents such as acetonitrile, N, N-dimethylformamide, N, N-dimethylacetamide, N-methyl-2-pyrrolidinone, 1,3-dimethyl-2-imidazolidinone, and dimethylsulfoxide; and mixtures thereof, but should not be specifically limited thereto unless it reacts under the reaction condition of the present step. The solvent includes preferably 2-propanol, tetrahydrofuran, toluene, acetonitrile, N, N-dimethylformamide, and the like.

The reaction temperature is generally-80° C. to reflux temperature, preferably 25° C. to 90° C.

The reaction time is generally 30 minutes to 48 hours, preferably 6 to 12 hours.

Alternatively, compound (a1) may be coupled with compound (a2) in the presence of an appropriate metal catalyst in an appropriate solvent. The reaction condition includes, for example, Ulmann-type condition (for example, heating under reflux with a metal catalyst such as copper (II) acetate in an aprotic solvent such as DMF), and Buchwald-type condition (for example, heating under reflux with alkali metal carbonate such as cesium carbonate; BINAP; a palladium catalyst such as $Pd_2(dba)_3$ and $Pd(OAc)_2$; and a ligand such as dppf and Xantphos, in an inert solvent under the reaction conditions such as toluene).

The solvent used herein includes, for example, alcohol solvents such as methanol, ethanol, 2-propanol (isopropyl alcohol), and tert-butanol; ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate, and methyl acetate; aprotic solvents such as acetonitrile, N, N-dimethylformamide, N, N-dimethylacetamide, N-methyl-2-pyrrolidinone, 1,3-dimethyl-2-imidazolidinone, and dimethylsulfoxide; water; and mixtures thereof, but should not be specifically limited thereto unless it reacts under the reaction condition of the present step. The solvent includes preferably tetrahydrofuran, toluene, acetonitrile, N, N-dimethylformamide, and the like.

The reaction temperature is generally −80° C. to reflux temperature, preferably 25° C. to 90° C.

The reaction time is generally 30 minutes to 48 hours, preferably 6 to 12 hours.

(Step 2)

Compound (A1) can be prepared by removing protecting group $P^1$ from compound (a3). The present step can be carried out according to a method described, for example, in Theodora. W. Greene, Peter. G. M. Wuts, "*Protective Groups in Organic Synthesis*", John Wiley & Sons, Inc., (1999), or a similar method.

Preparation Process B

In the compound of formula (a1), the compound of formula (B1) can be prepared, for example, by the following method:

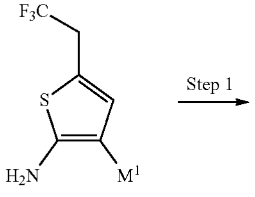

(b1)

-continued

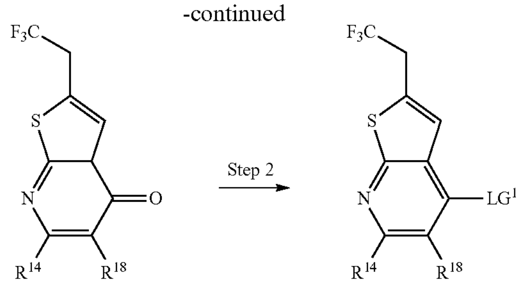

(b2) (B1)

wherein $M^1$ is hydrogen atom, an ester, etc.; $R^{14}$ and $R^{18}$ are as defined in Item 1; and $LG^1$ is as defined in Preparation Process A.

Compound (b1) can be prepared by a method described in WO 2014/164543 or a similar method thereto.

(Step 1)

Compound (b2) can be prepared from Compound (b1) by a method described in Tetrahedron Letters, 49 (48): 6850-6852 (2008), J. Med. Chem., 48 (18): 5794-5804 (2005), Journal of Heterocyclic Chemistry, 28 (8): 1953-1955 (1991), etc. or a similar method thereto.

(Step 2)

Compound (B1) can be prepared from Compound (b2) by a method described in J. Med. Chem., 38 (18): 3536-3546 (1995), J. Med. Chem., 59 (3): 1078-1101 (2016), J. Med. Chem., 58 (14): 5522-5537 (2015), Comprehensive Organic Transformation $2^{nd}$ Edition (edited by Larock R. C., issued by John Wiley & Sons, Inc., in 1989), etc. or a similar method thereto.

Preparation Process C

In the compound of formula (a1), the compound of formula (C1) can be prepared, for example, by the following method:

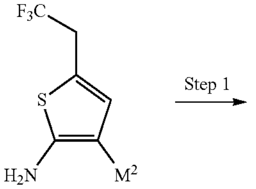

(c1)

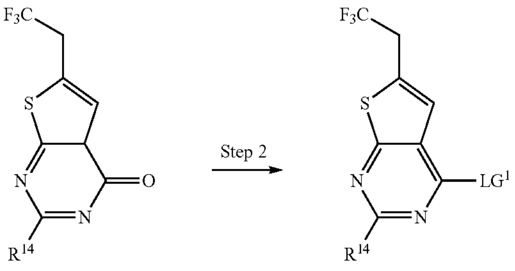

(c2) (C1)

wherein $M^2$ is an ester, an amide, etc.; $R^{14}$ is as defined in Item 1; $LG^1$ is as defined in Preparation Process A.

Compound (c1) can be prepared by a method described in WO 2014/164543, WO 2017/112768, J. Med. Chem., 59 (3): 892-913 (2016), etc. or a similar method thereto.

(Step 1)

Compound (c2) can be prepared from compound (c1) by a method described in WO 2017/112768, J. Med. Chem., 59 (3): 892-913 (2016), etc. or a similar method thereto.

(Step 2)

Compound ($C_1$) can be prepared from compound (c2) by a method described in WO 2017/112768, J. Med. Chem., 59 (3): 892-913 (2016), Comprehensive Organic Transformation $2^{nd}$ Edition (edited by Larock R. C., issued by John Wiley & Sons, Inc., in 1989), etc. or a similar method thereto.

Preparation Process D

In the compound of formula (a2), the compound of formula (D1) can be prepared, for example, by the following method:

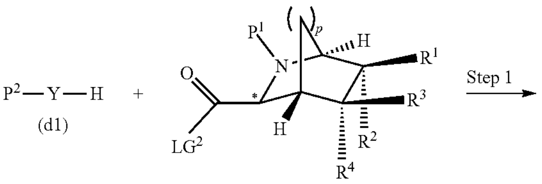

(d2)

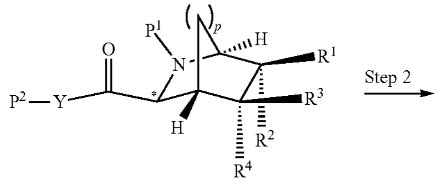

(d3)

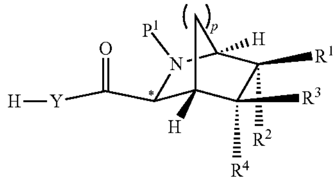

(D1)

wherein p, $R^1$, $R^2$, $R^3$, $R^4$, and Y are as defined in Item 1; $LG^2$ is a leaving group; $P^1$ is as defined in Preparation Process A; and $P^2$ is an amino-protecting group, wherein $LG^2$ includes, for example, halogen atom, hydroxy, and the like; $P^2$ includes, for example, amino-protecting groups described in Theodora W. Greene, and Peter G. M. Wuts, "*Protective Groups in Organic Synthesis*", John Wiley & Sons, Inc., (1999), and the like; and the stereochemistry of the carbon with * is not inverted during reactions.

Compound (d1) is commercially available.

Compound (d2) can be prepared by a method described in JP 2007-510619 A, J. Chem. Soc., Chem. Commun., 1599-1601 (1988), Tetrahedron Letters, 43:5957-5960 (2002), Tetrahedron Asymmetry, 2:1263-1282 (1991), Tetrahedron Asymmetry, 27:1062-1068 (2016), Comprehensive Organic Transformation $2^{nd}$ Edition (edited by Larock R. C., issued by John Wiley & Sons, Inc., in 1989), etc. or a similar method thereto, or can be obtained as a marketed product.

(Step 1)

Compound (d3) can be prepared by reacting compound (d1) with compound (d2) such as a carboxylic acid compound and an acid chloride compound in the presence of an appropriate condensing agent and/or an appropriate base in an appropriate solvent.

The base used herein includes amines such as triethylamine, diisopropylethylamine, and pyridine; carbonates of alkali metal such as potassium carbonate, sodium carbonate, and sodium bicarbonate. The base includes preferably triethylamine, diisopropylethylamine, and pyridine.

The condensing agent used herein is optionally selected from condensing agents commonly-used in organic synthetic chemistry, and includes preferably 1-ethyl-3-(3-dimethylaminopropyl) carbodiimide hydrochloride, 1-hydroxybenzotriazole, and the like.

The solvent used herein includes, for example, ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; ester solvents such as ethyl acetate, and methyl acetate; aprotic solvents such as acetonitrile, N, N-dimethylformamide, N, N-dimethylacetamide, N-methyl-2-pyrrolidinone, 1,3-dimethyl-2-imidazolidinone, and dimethylsulfoxide; halogenated hydrocarbon solvents such as dichloromethane (methylene chloride), chloroform, and 1,2-dichloroethane; and mixtures thereof, but should not be specifically limited thereto unless it reacts under the reaction condition of the present step. The solvent includes preferably tetrahydrofuran, toluene, acetonitrile, N, N-dimethylformamide, dichloromethane, and the like.

The reaction time is generally 5 minutes to 72 hours, preferably 30 minutes to 24 hours.

The reaction temperature is generally −78° C. to 200° C., preferably −78° C. to 80° C.

(Step 2)

Compound (D1) can be prepared by removing protecting group $P^2$ from compound (d3). The present step can be carried out according to a method described, for example, in Theodora. W. Greene, Peter. G. M. Wuts, "*Protective Groups in Organic Synthesis*", John Wiley & Sons, Inc., (1999), or a similar method.

Preparation Process E

In the compound of formula (a2), the compound of formula (E1) can be prepared, for example, by the following method:

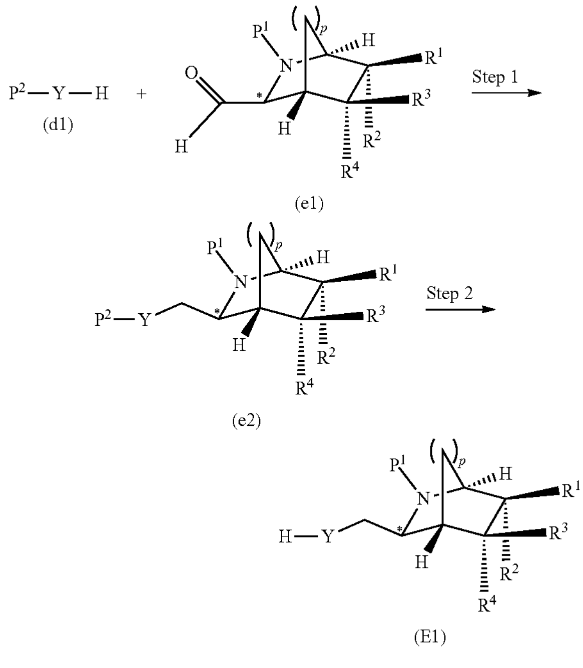

(d1) (e1) (e2) (E1)

wherein p, $R^1$, $R^2$, $R^3$, $R^4$, and Y are as defined in Item 1; $P^1$ is as defined in Preparation Process A; $P^2$ is as defined in Preparation Process D; and the stereochemistry of the carbon with * is not inverted during reactions.

Compound (e1) can be prepared by a method described in JP 2007-510619 A, J. Chem. Soc., Chem. Commun., 1599-1601 (1988), Tetrahedron Letters, 43:5957-5960 (2002), Tetrahedron Asymmetry, 2:1263-1282 (1991), Tetrahedron Asymmetry, 27:1062-1068 (2016), Comprehensive Organic Transformation $2^{nd}$ Edition (edited by Larock R. C., issued by John Wiley & Sons, Inc., in 1989), etc. or a similar method thereto, or can be obtained as a marketed product.

(Step 1)

Compound (e2) can be prepared from compound (d1) and compound (e1) by a method described in J. Am. Chem. Soc., 93 (12): 2897-2904 (1971), J. Org. Chem., 37 (10): 1673-1674 (1972), J. Org. Chem., 61 (11): 3849-3862 (1996), Tetrahedron, 60:7899-7906 (2004), etc. or a similar method thereto.

(Step 2)

Compound (E1) can be prepared by removing protecting group $P^2$ from compound (e2). The present step can be carried out according to a method described, for example, in Theodora. W. Greene, Peter. G. M. Wuts, "*Protective Groups in Organic Synthesis*", John Wiley & Sons, Inc., (1999), or a similar method.

Preparation Process F

The compound of formula (F1) can be prepared, for example, by the following process:

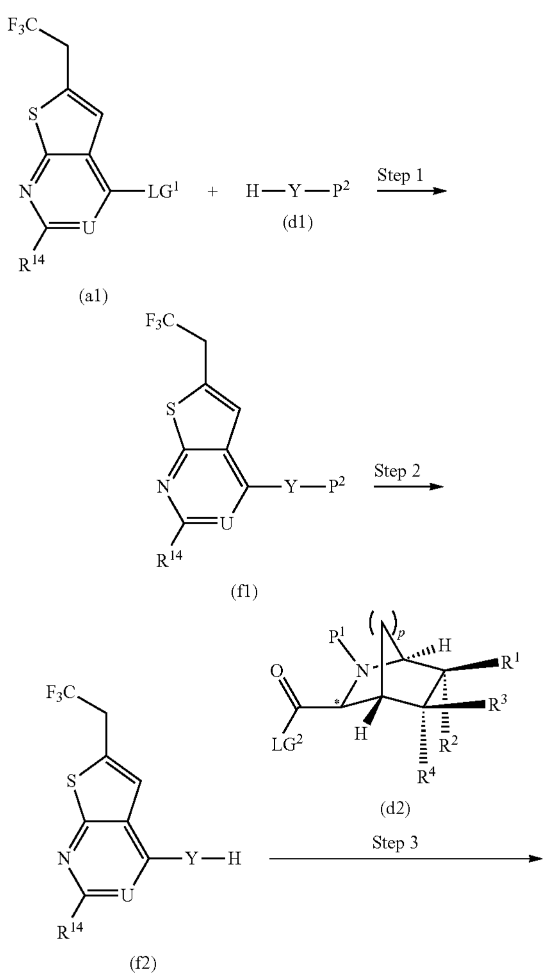

(a1) (d1) (f1) (d2) (f2)

-continued

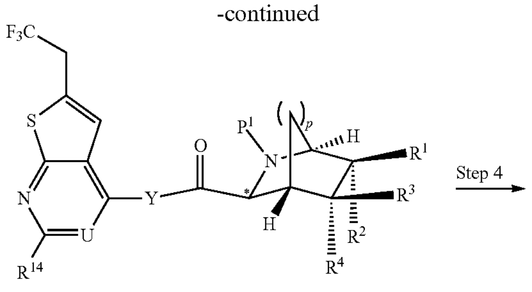

(f3)

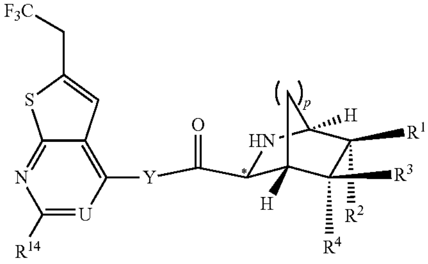

(F1)

wherein p, $R^1$, $R^2$, $R^3$, $R^4$, $R^{14}$, U, and Y are as defined in Item 1; $LG^1$ is as defined in Preparation Process A; $LG^2$ is as defined in Preparation Process D; $P^1$ is as defined in Preparation Process A; $P^2$ is as defined in Preparation Process D; and the stereochemistry of the carbon with * is not inverted during reactions.

(Step 1)

Compound (f1) can be prepared from compound (a1) and compound (d1) by the method described in step 1 of Preparation Process A or a similar method.

(Step 2)

Compound (f2) can be prepared by removing protecting group $P^2$ from compound (f1). The present step can be carried out according to a method described, for example, in Theodora. W. Greene, Peter. G. M. Wuts, "*Protective Groups in Organic Synthesis*", John Wiley & Sons, Inc., (1999), or a similar method.

(Step 3)

Compound (f3) can be prepared from compound (f2) and compound (d2) by the method described in step 1 of Preparation Process D or a similar method.

(Step 4)

Compound (F1) can be prepared by removing protecting group $P^1$ from compound (f3). The present step can be carried out according to a method described, for example, in Theodora. W. Greene, Peter. G. M. Wuts, "*Protective Groups in Organic Synthesis*", John Wiley & Sons, Inc., (1999), or a similar method.

Preparation Process G

The compound of formula (G1) can be prepared, for example, by the following process:

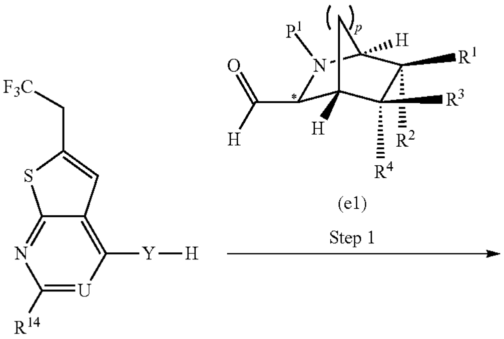

(e1)

(f2)

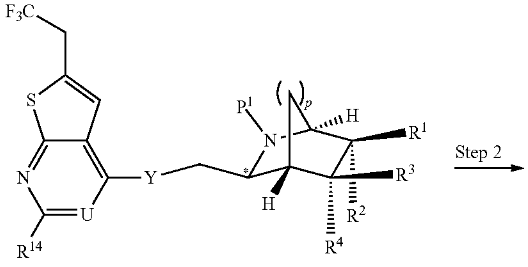

(g1)

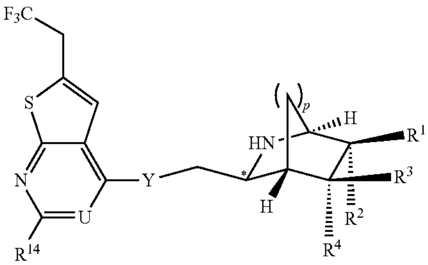

(G1)

wherein p, $R^1$, $R^2$, $R^3$, $R^4$, $R^{14}$, U, and Y are as defined in Item 1; $P^1$ is as defined in Preparation Process A; and the stereochemistry of the carbon with * is not inverted during reactions.

(Step 1)

Compound (g1) can be prepared from compound (f2) and compound (e1) by the method described in step 1 of Preparation Process E or a similar method.

(Step 2)

Compound (G1) can be prepared by removing protecting group $P^1$ from compound (g1). The present step can be carried out according to a method described, for example, in Theodora. W. Greene, Peter. G. M. Wuts, "*Protective Groups in Organic Synthesis*", John Wiley & Sons, Inc., (1999), or a similar method.

Preparation Process H

In the compound of formula (d2), the compound of formula (H1) can be prepared, for example, by the following method:

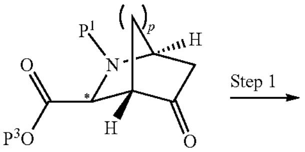

(h1)

-continued

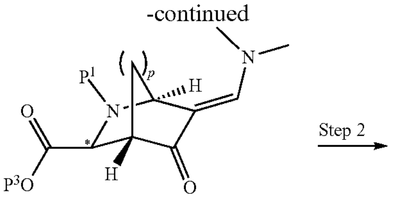

(h2)

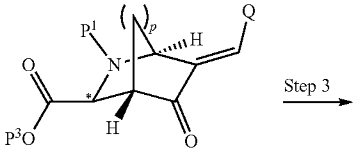

(h3)

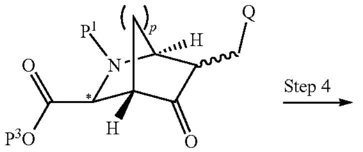

(h4)

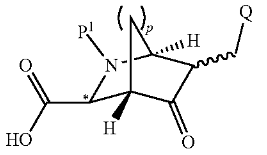

(H1)

wherein p and Q are as defined in Item 1; $P^1$ is as defined in Preparation Process A; $P^3$ is a protecting group of carboxylic acid, wherein $P^3$ includes, for example, carboxylic acid-protecting groups described in Theodora W. Greene, and Peter G. M. Wuts, "*Protective Groups in Organic Synthesis*", John Wiley & Sons, Inc., (1999), and the like; and the stereochemistry of the carbon with * is not inverted during reactions.

Compound (h1) can be prepared by a method described in JP 2007-510619 A, J. Chem. Soc., Chem. Commun., 1599-1601 (1988), Tetrahedron Letters, 43:5957-5960 (2002), Tetrahedron Asymmetry, 2:1263-1282 (1991), Tetrahedron Asymmetry, 27:1062-1068 (2016), Comprehensive Organic Transformation $2^{nd}$ Edition (edited by Larock R. C., issued by John Wiley & Sons, Inc., in 1989), etc. or a similar method thereto, or can be obtained as a marketed product.

(Step 1)

Compound (h2) can be prepared from compound (h1) by a method described in Tetrahedron Letters, 27:2567-2570 (1986), Synthesis, 12:1930-1935 (2011), Bioorganic & Medicinal Chemistry Letters, 23:4493-4500 (2013), European Journal of Organic Chemistry, 10:2485-2490 (1999), etc. or a similar method thereto.

(Step 2)

Compound (h3) can be prepared from compound (h2) by a method described in Synthetic Communications, 28:1743-1753 (1998), Chemistry Letters, 6:875-878 (1983), Journal of Organic Chemistry, 28:6-16 (1963), etc. or a similar method thereto.

(Step 3)

Compound (h4) can be prepared from compound (h3) by a method described in Tetrahedron Letters, 23:477-480 (1982), Synlett, 443-444 (1995), Synlett, 96-98 (1999), Tetrahedron, 56:2779-2788 (2000), etc. or a similar method thereto.

(Step 4)

Compound (H1) can be prepared by removing protecting group $P^3$ from compound (h4). The present step can be carried out according to a method described, for example, in Theodora. W. Greene, Peter. G. M. Wuts, "*Protective Groups in Organic Synthesis*", John Wiley & Sons, Inc., (1999), or a similar method.

Preparation Process I

In the compound of formula (d2), the compound of formula (I1) can be prepared, for example, by the following method:

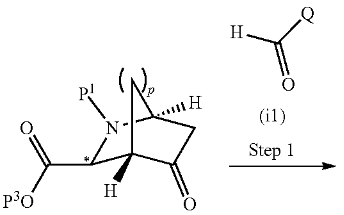

(i1)

(h1)

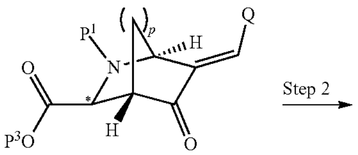

(h3)

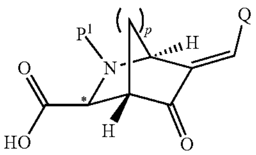

(I1)

wherein p and Q are as defined in Item 1; $P^1$ is as defined in Preparation Process A; $P^3$ is as defined in Preparation Process H; and the stereochemistry of the carbon with * is not inverted during reactions.

Compound (i1) is commercially available.

(Step 1)

Compound (h3) can be prepared from compound (h1) and compound (i1) by a method described in Journal of the American Chemical Society, 126:14206-14216 (2004), Synthetic Communications, 20:839-847 (1990), Synthesis, 23: 3821-3826 (2011), Advanced Synthesis & Catalysis, 352: 153-162 (2010), etc. or a similar method thereto.

(Step 2)

Compound (I1) can be prepared by removing protecting group $P^3$ from compound (h3). The present step can be carried out according to a method described, for example, in Theodora. W. Greene, Peter. G. M. Wuts, "*Protective Groups in Organic Synthesis*", John Wiley & Sons, Inc., (1999), or a similar method.

Preparation Process J

In the compound of formula (d2), the compound of formula (J1) can be prepared, for example, by the following method:

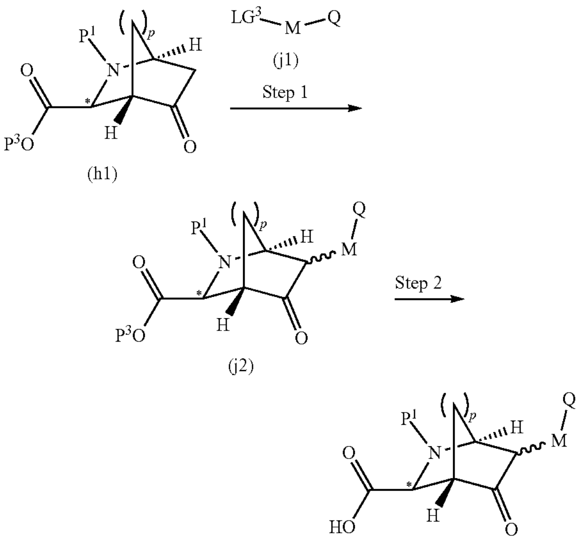

(h1) (j1) (j2) (J1)

wherein p, M, and Q are as defined in Item 1; $LG^3$ is the same definition as $LG^1$ in Preparation Process A; $P^1$ is as defined in Preparation Process A; $P^3$ is as defined in Preparation Process H; and the stereochemistry of the carbon with * is not inverted during reactions.

Compound (j1) is commercially available.

(Step 1)

Compound (j2) can be prepared from compound (h1) and compound (j1) by a method described in Journal of the American Chemical Society, 132:1236-1237 (2010), Journal of Medicinal Chemistry, 49:4409-4424 (2006), Advanced Synthesis & Catalysis, 357:2803-2808 (2015), Tetrahedron Letters, 47 (19): 3233-3237 (2006), Angewandte Chemie, International Edition, 44 (34): 5516-5519 (2005), etc. or a similar method thereto.

(Step 2)

Compound (J1) can be prepared by removing protecting group $P^3$ from compound (j2). The present step can be carried out according to a method described, for example, in Theodora. W. Greene, Peter. G. M. Wuts, "*Protective Groups in Organic Synthesis*", John Wiley & Sons, Inc., (1999), or a similar method.

Preparation Process K

The compound of formula (A1) can be prepared, for example, by the following process:

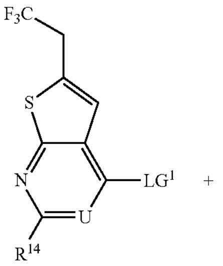

(a1)

-continued

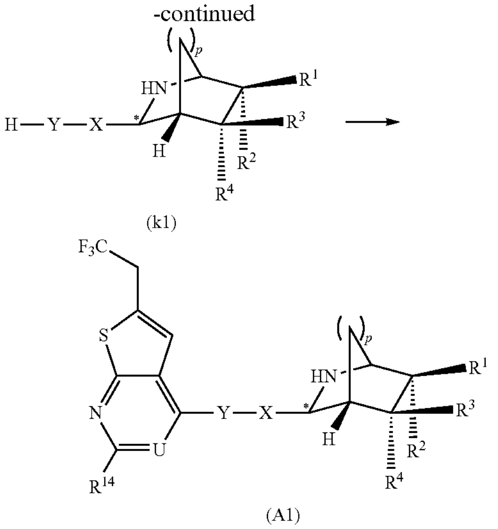

(k1) (A1)

wherein p, $R^1$, $R^2$, $R^3$, $R^4$, $R^{14}$, U, X, and Y are as defined in Item 1; $LG^1$ is as defined in Preparation Process A; and the stereochemistry of the carbon with * is not inverted during reactions.

Compound (A1) can be prepared from Compound (a1) and Compound (k1) prepared by the following preparation process, by the method described in step 1 of Preparation Process A or a similar method.

As compound (k1), compound (L1) prepared in the following Preparation Process L or Compound (M1) prepared in the following Preparation Process M may be used.

Preparation Process L

In the compound of formula (k1), the compound of formula (L1) can be prepared, for example, by the following method:

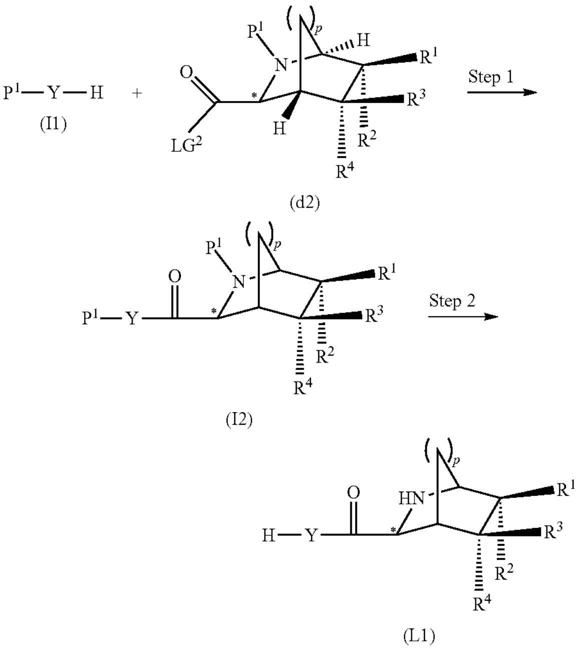

(I1) (d2) (I2) (L1)

wherein p, $R^1$, $R^2$, $R^3$, $R^4$, and Y are as defined in Item 1; $P^1$ is as defined in Preparation Process A; $LG^2$ is as defined in Preparation Process D; and the stereochemistry of the carbon with * is not inverted during reactions.

Compound (11) is commercially available.

(Step 1)

Compound (12) can be prepared from compound (11) and compound (d2) by the method described in step 1 of preparation Process D or a similar method.

(Step 2)

Compound (L1) can be prepared by removing protecting group $P^1$ from compound (12). The present step can be carried out according to a method described, for example, in Theodora. W. Greene, Peter. G. M. Wuts, "*Protective Groups in Organic Synthesis*", John Wiley & Sons, Inc., (1999), or a similar method.

Preparation Process M

In the compound of formula (k1), the compound of formula (M1) can be prepared, for example, by the following method:

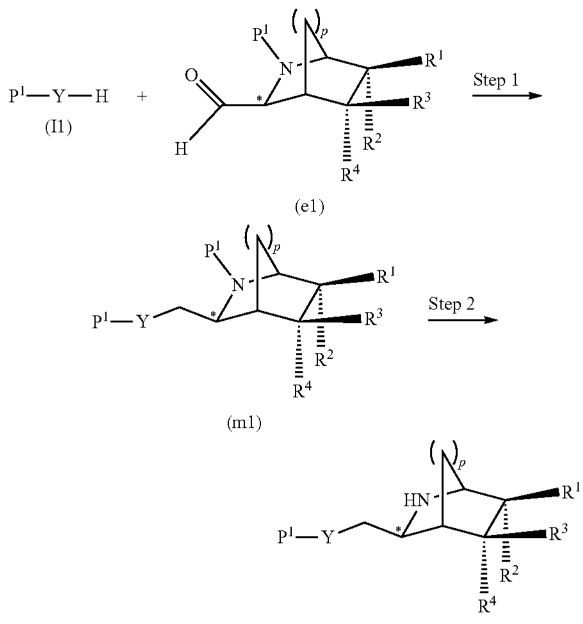

(I1) (e1) (m1) (M1)

wherein p, $R^1$, $R^2$, $R^3$, $R^4$, and Y are as defined in Item 1; $P^1$ is as defined in Preparation Process A; and the stereochemistry of the carbon with * is not inverted during reactions.

(Step 1)

Compound (m1) can be prepared from compound (I1) and compound (e1) by the method described in step 1 of Preparation Process E or a similar method.

(Step 2)

Compound (M1) can be prepared by removing protecting group $P^1$ from compound (m1). The present step can be carried out according to a method described, for example, in Theodora. W. Greene, Peter. G. M. Wuts, "*Protective Groups in Organic Synthesis*", John Wiley & Sons, Inc., (1999), or a similar method.

In the above preparation processes, starting materials or intermediates which are not described for preparation processes can be obtained as marketed products, or can be prepared from marketed products by a method well-known to those skilled in the art.

In each reaction described above, protecting groups can be used as necessary, even if the use of protecting groups is not explicitly stated. For example, when any one or more functional groups other than reaction sites are converted to undesired forms under the reaction condition, or the process described above cannot be carried out properly without protecting groups, protecting groups can be used to protect groups other than reaction sites as necessary, and can be deprotected after the reaction is completed or a series of reactions have been carried out to obtain the desired compound.

As such protecting groups, for example, the groups described in Theodora W. Greene, Peter G. M. Wuts, "*Protective Groups in Organic Synthesis*", John Wiley & Sons, Inc., (1999), and the like may be used. Examples of amino-protecting groups include, for example, benzyloxycarbonyl, tert-butoxycarbonyl, acetyl, benzyl, and the like. Examples of hydroxy-protecting groups include, for example, trialkylsilyl such as trimethylsilyl and tert-butyldimethylsilyl, acetyl, benzyl, and the like.

The introduction and elimination of protecting groups can be carried out by a method commonly-used in synthetic organic chemistry (for example, see "*Protective Groups in Organic Synthesis*" described above), or a similar method.

In the present specification, protecting groups, condensing agents and the like may be described in an abbreviated form according to IUPAC-IUB (Biochemical nomenclature committee) commonly-used in this technical field. It should be understood that the names of compounds used in the present specification do not necessarily follow the IUPAC nomenclature.

The intermediates or the desired compounds which are described in the above preparation processes can be transformed to other compounds which fall within the present invention by optionally converting their functional groups to other groups (for example, the conversion from amino, hydroxy, carbonyl, halogen atom, and the like, while protecting or deprotecting other functional groups as necessary). The conversion of functional groups can be carried out by a general method which are commonly used (see, for example, R. C. Larock, "*Comprehensive Organic Transformations*", John Wiley & Sons Inc. (1999)).

The intermediates and the desired compounds described above can be isolated and purified by a purification method commonly-used in organic synthetic chemistry (for example, neutralization, filtration, extraction, washing, drying, enrichment, recrystallization, various chromatography, and the like). In addition, intermediates may be used in next reaction without further purification.

The "pharmaceutically acceptable salt" includes acid addition salts and base addition salts. For example, the acid addition salt includes inorganic acid salts such as hydrochloride, hydrobromide, sulfate, hydroiodide, nitrate, and phosphate; and organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate, and camphorsulfonate. The base addition salt includes inorganic base salts such as sodium salts, potassium salts, calcium salts, magnesium salts, barium salts, and aluminum salts; and organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine, and N, N-dibenzylethylamine. The "pharmaceutically acceptable salt" also includes amino acid salts of basic or acidic amino acids such as arginine, lysine, ornithine, aspartate, and glutamate.

The suitable salts of starting materials and intermediates and the acceptable salts of drug substances are conventional non-toxic salts. The suitable salt includes, for example, acid addition salts such as organic acid salts (including acetate, trifluoroacetate, maleate, fumarate, citrate, tartrate, methanesulfonate, benzenesulfonate, formate, and toluenesulfonate) and inorganic acid salts (including hydrochloride, hydrobromide, hydroiodide, sulfate, nitrate, and phosphate); salts with amino acids (including arginine, aspartate, and glutamate); alkali metal salts (including sodium salts, and potassium salts); alkaline earth metal salts (including calcium salts, and magnesium salts); ammonium salts; organic base salts (including trimethylamine salts, triethylamine salts, pyridine salts, picolinate, dicyclohexylamine salts, and N,N'-dibenzylethylenediamine salts); and other salts which a person skilled in the art can optionally select.

In the present invention, the "hydrogen atom" includes $^{1}H$ and $^{2}H$ (D), and the compound of formula (1) encompasses deuterated compounds in which any one or more $^{1}H$ in the compound of formula (1) are replaced with $^{2}H$ (D).

The present invention encompasses compounds of formula (1) or pharmaceutically acceptable salts thereof. The compound of the present invention may exist in a form of hydrate and/or solvate of various solvents, including ethanolate, and these hydrate and/or solvate are included in the compound of the present invention.

The compound of the present invention encompasses optical isomers based on an optically active center, atropisomers based on axial or planar chirality caused by restriction of intramolecular rotation, and all other isomers which can exist as stereoisomers, tautomers, and geometric isomers, and crystalline forms in various states, and mixtures thereof.

Especially, each optical isomer and atropisomer can be obtained as a racemate, or as an optically active substance when an optically active starting material or intermediate is used. Racemates of corresponding starting materials, intermediates, or final products can also be physically or chemically resolved into optical enantiomers by a known isolating method such as a method with an optically active column and a fractional crystallization method, at an appropriate step in the above preparation processes, if necessary. These methods for resolving enantiomers include a diastereomer method in which, for example, a racemate is reacted with an optically active resolving agent to synthesize two kinds of diastereomers, which are resolved by fractional crystallization or a similar method through different physical characters.

If the compound of the present invention should be obtained as a pharmaceutically acceptable salt thereof, when the compound of formula (1) is obtained as a pharmaceutically acceptable salt, it may be purified without further reaction, and when it is obtained in a free form, it may be solved or suspended in an appropriate organic solvent and an acid or base may be added therein to form a salt by a common method.

The antitumor agent which can be used in combination with the compound of the present invention or can be combined with the compound of the present invention includes, for example, at least one antitumor agent selected from the group consisting of an anticancer alkylating agent, an anticancer antimetabolite, an anticancer antibiotic, a plant-derived anticancer medicament, an anticancer platinum complex compound, an anticancer camptothecin derivative, an anticancer tyrosine kinase inhibitor, an anticancer serine/threonine kinase inhibitor, an anticancer phospholipid kinase inhibitor, an anticancer monoclonal antibody, interferon, an biological response modifier, a hormone preparation, an immune checkpoint inhibitor, an epigenetics-associated molecular inhibitor, a protein post-translational modification inhibitor, and other antitumor medicaments, or a pharmaceutically acceptable salt thereof. Examples of the "antitumor agent which can be used in combination with the compound of the present invention or can be combined with the compound of the present invention" include, for example, azacytidine, vorinostat, decitabine, romidepsin, idarubicin, daunorubicin, doxorubicin, enocitabine, cytarabine, mitoxantrone, thioguanine, etoposide, ifosfamide, cyclophosphamide, dacarbazine, temozolomide, nimustine, busulfan, procarbazine, melphalan, ranimustine, all-trans-retinoic acid, tamibarotene, cisplatin, carboplatin, oxaliplatin, irinotecan, bleomycin, mitomycin c, methotrexate, paclitaxel, docetaxel, gemcitabine, tamoxifen, thiotepa, tegafur, fluorouracil, everolimus, temsirolimus, gefitinib, erlotinib, imatinib, crizotinib, osimertinib, afatinib, dasatinib, bosutinib, vandetanib, sunitinib, axitinib, pazopanib, lenvatinib, lapatinib, nilotinib, ibrutinib, ceritinib, alectinib, tofacitinib, baricitinib, ruxolitinib, olaparib, sorafenib, vemurafenib, dabrafenib, trametinib, palbociclib, bortezomib, carfilzomib, rituximab, cetuximab, trastuzumab, bevacizumab, panitumumab, nivolumab, atezolizumab, mogamulizumab, alemtuzumab, ofatumumab, ipilimumab, ramucirumab, brentuximab vedotin, gemtuzumab ozogamicin, inotuzumab ozogamicin, and the like.

The administration route of the compound of the present invention may oral, be parenteral, intrarectal, or ophthalmic administration, and the daily dose depends on the type of compounds, administration methods, the condition or age of patients, and the like. For example, in the case of oral administration, about 0.01 to 1000 mg, more preferably about 0.1 to 500 mg per kg body weight of a human or mammal can be usually administrated in one to several portions. In the case of parenteral administration such as intravenous injection, for example, about 0.01 mg to 300 mg, more preferably about 1 mg to 100 mg per kg body weight of a human or mammal can be usually administrated.

The compound of the present invention can be orally or parenterally administrated directly or as a suitable drug formulation. The dosage form includes, for example, a tablet, a capsule, a powder, a granule, a liquid, a suspension, an injection, a patch, a poultice, and the like, but it is not limited to them. The drug formulation is prepared by a common method using pharmaceutically acceptable additives.

As the additive, an excipient, a disintegrant, a binder, a fluidizer, a lubricant, a coating agent, a solubilizer, a solubilizing adjuvant, a thickener, a dispersant, a stabilizing agent, a sweetening agent, a flavor, and the like may be used, depending on purpose. The additive used herein includes, for example, lactose, mannitol, crystalline cellulose, low-substituted hydroxypropylcellulose, corn starch, partially-pregelatinized starch, carmellose calcium, croscarmellose sodium, hydroxypropylcellulose, hydroxypropylmethylcellulose, polyvinyl alcohol, magnesium stearate, sodium stearyl fumarate, polyethylene glycol, propylene glycol, titanium oxide, talc, and the like.

EXAMPLES

The present invention is explained in more detail in the following by referring to Reference examples, Examples, and Tests; however, the technical scope of the present invention should not be limited thereto.

In the present specification, the abbreviations shown below may be used.

THF: tetrahydrofuran
TFA: trifluoroacetic acid
DMF: N, N-dimethylformamide
DMSO: dimethylsulfoxide
MeCN: acetonitrile
Me: methyl
Et: ethyl
Ph: phenyl
Bn: benzyl
Boc: tert-butoxycarbonyl
n-: normal-
tert-: tertiary-
p-: para-
BINAP: 2,2'-bis(diphenylphosphino)-1,1'-binaphthyl
$Pd_2(dba)_3$: tris(dibenzylideneacetone)dipalladium(0)
Ac: acetyl
dppf: 1,1'-bis(diphenylphosphino) ferrocene
Xantphos: 4,5-bis(diphenylphosphino)-9,9-dimethylxanthene
Dess-Martin reagent: Dess-Martin periodinane (1,1,1-triacetoxy-1,1-dihydro-1,2-benziodoxol-3-(1H)-one)
Petasis reagent: bis(cyclopentadienyl)dimethyltitanium
Bredereck reagent: tert-butoxy-bis(dimethylamino) methane
HATU: 1-[bis(dimethylamino)methylene]-1H-1,2,3-triazolo[4,5-b]pyridinium 3-oxide hexafluorophosphate
WSCI·HCl: 1-(3-dimethylaminopropyl)-3-ethylcarbodiimide hydrochloride
HOBt: 1-hydroxybenzotriazole NMR (Nuclear Magnetic Resonance) data used for identification of compounds were obtained with a JNM-ECS400 type nuclear magnetic resonance instrument (400 MHz) from JEOL Ltd.

The symbols used in NMR are defined as follows, s: singlet, d: doublet, dd: doublet of doublet, t: triplet, td: triplet of doublet, q: quartet, m: multiplet, br: broad, brs: broad singlet, brm: broad multiplet, and J: coupling constant.

Analytical conditions of LC/MS (Liquid Chromatography-Mass Spectrometry) used for identification of compounds are shown below. In observed mass spectrometry values [MS (m/z)], monoisotopic mass (exact mass consisting of only main isotope) is shown in $[M+H]^+$, $[M-H]^-$, or $[M+2H]^{2+}$, etc., and retention time is shown as Rt (minutes).

The analytical conditions of LC/MS:

Analytical Condition A

Detection apparatus: detector (Waters ACQUITY™ SQ Corporation)
HPLC: ACQUITY™ UPLC system
Column: Waters ACQUITY™ UPLC BEH C18 (1.7 μm, 2.1 mm×30 mm)
Solvent: A: 0.06% formic acid/$H_2O$, B: 0.06% formic acid/MeCN
Gradient condition: 0.0 to 1.3 minutes Linear gradient of B 2% to B 96%
Flow rate: 0.8 mL/min
UV: 220 nm and 254 nm
Column temperature: 40° C.

Analytical Condition B

Detection apparatus: LCMS-2020 (Shimadzu Corporation)
HPLC: Nexera X2
Column: Phenomenex Kinetex™ 1.7 μm C18 (50 mm×2.1 mm)
Solvent: A: 0.05% TFA/$H_2O$, B: MeCN
Gradient condition: 0.0 to 1.7 minutes Linear gradient of B 10% to B 99%
Flow rate: 0.5 mL/min
UV: 220 nm and 254 nm
Column temperature: 40° C.

Reference Example 1

4-Chloro-2-(2,2,2-trifluoroethyl)-5-(trifluoromethyl)thieno[2,3-b]pyridine

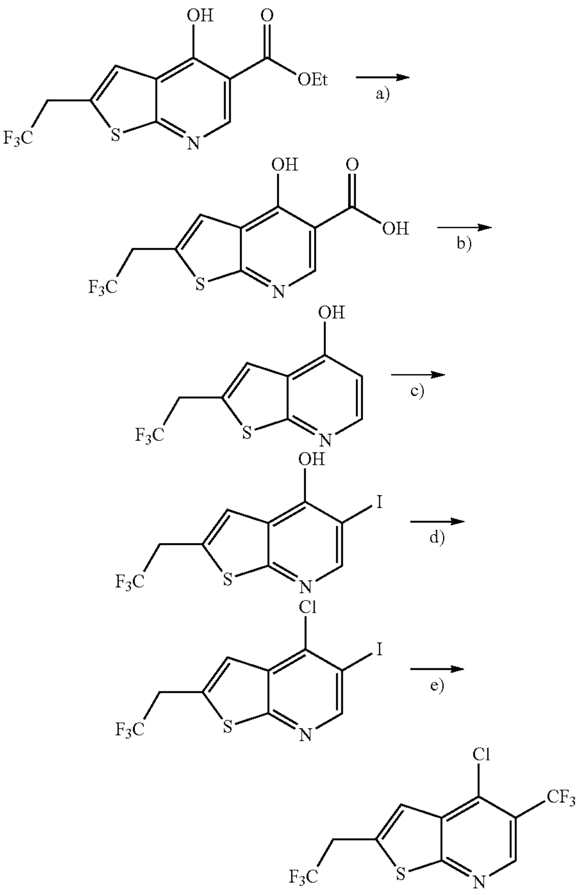

Reference example 1 a) Preparation of 4-hydroxy-2-(2,2,2-trifluoroethyl)thieno[2,3-b]pyridine-5-carboxylic acid Ethyl 4-hydroxy-2-(2,2,2-trifluoroethyl)thieno[2,3-b]pyridine-5-carboxylate (40 g) was suspended in a mixture of THF (200 mL), methanol (100 mL), and water (200 mL), and then 4 mol/L aqueous sodium hydroxide (90 mL) was added thereto at room temperature. The mixture was stirred at room temperature to 40° C. for 5 days. The reaction solution was weakly-acidified with 5 mol/L aqueous hydrochloric acid. The precipitated solid was collected on a filter, and dried at 70° C. in vacuo to give the titled compound (36.9 g) as a crude product.

LC-MS; $[M+H]^+$ 278.1/Rt (min) 0.64 (Analytical condition A)

b) Preparation of 2-(2,2,2-trifluoroethyl)thieno[2,3-b]pyridin-4-ol

To a solution of 4-hydroxy-2-(2,2,2-trifluoroethyl)thieno [2,3-b]pyridine-5-carboxylic acid (18 g) in quinoline (100 mL) was added copper (0.83 g), and the mixture was stirred at 190° C. for 3 hours. The reaction solution was cooled, and then purified by silica gel column chromatography (eluting with hexane/ethyl acetate, then chloroform/methanol) to give the titled compound (15.0 g).

LC-MS; $[M+H]^+$ 234.1/Rt (min) 0.54 (Analytical condition A)

c) Preparation of 5-iodo-2-(2,2,2-trifluoroethyl) thieno[2,3-b]pyridin-4-ol

To a suspension of 2-(2,2,2-trifluoroethyl)thieno[2,3-b] pyridin-4-ol (30 g) in acetonitrile (322 mL) was added N-iodosuccinimide (32 g) at at room temperature, and the mixture was stirred under reflux for 2 hours. The reaction mixture was cooled to 0° C. The precipitated solid was collected on a filter, and washed with acetonitrile and then hexane to give the titled compound (46.2 g).

LC-MS; $[M+H]^+$ 360.0/Rt (min) 0.65 (Analytical condition A)

d) Preparation of 4-chloro-5-iodo-2-(2,2,2-trifluoroethyl)thieno[2,3-b]pyridine

5-Iodo-2-(2,2,2-trifluoroethyl)thieno[2,3-b]pyridin-4-ol (46 g) was added to phosphoryl chloride (179 mL) at room temperature, then DMF (0.5 mL) was added thereto, and the mixture was stirred at 70° C. for 2 hours. After cooling, the reaction mixture was concentrated under reduced pressure, and the residue was quenched by addition of saturated aqueous sodium bicarbonate. The resulting aqueous solution was extracted twice with ethyl acetate. The resulting organic layer was washed with brine, dried over anhydrous sodium sulfate, and filtrated, and the solvent was removed under reduced pressure. The residue was washed with methanol to obtain the title compound (33.2 g).

LC-MS; $[M+H]^+$ 378.0/Rt (min) 1.19 (Analytical condition A)

e) Preparation of 4-chloro-2-(2,2,2-trifluoroethyl)-5-(trifluoromethyl)thieno[2,3-b]pyridine (Reference example 1)

To a solution of 4-chloro-5-iodo-2-(2,2,2-trifluoroethyl) thieno[2,3-b]pyridine (37 g) in DMF (420 mL) was added (1,10-phenanthroline) (trifluoromethyl) copper (I) (77 g), and the mixture was stirred at 80° C. for 3 hours. After cooling, the insoluble matter was removed by Celite filtration. The Celite was washed with ethyl acetate. To the filtrate were added toluene and ethyl acetate, and the mixture was washed with water (×2) anf brine (×1). The resulting organic layer was dried over anhydrous sodium sulfate, and filtrated, and the solvent was removed under reduced pressure. The residue was purified by silica gel column chromatography (hexane/ethyl acetate) to yield the titled compound (16.9 g).

$^1$H-NMR (DMSO-$D_6$) δ: 8.95 (1H, s), 7.72 (1H, s), 4.30 (2H, q, J=11.2 Hz).

LC-MS; $[M+H]^+$ 320.0/Rt (min) 1.19 (Analytical condition A)

Reference Example 2

4-(2,6-Diazaspiro[3.3]heptan-2-yl)-2-(2,2,2-trifluoroethyl)-5-(trifluoromethyl)thieno[2,3-b]pyridine

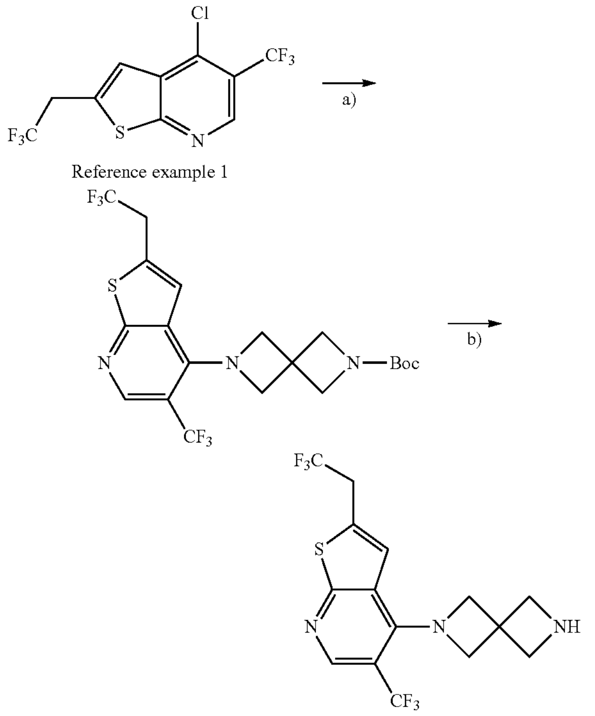

Reference example 1

Reference example 2 a) Preparation of tert-butyl 6-{2-(2,2,2-trifluoroethyl)-5-(trifluoromethyl)thieno[2,3-b]pyridin-4-yl}-2,6-diazaspiro [3.3]heptane-2-carboxylate To a solution of 4-chloro-2-(2,2,2-trifluoroethyl)-5-(trifluoromethyl)thieno[2,3-b]pyridine (16 g) in acetonitrile (100 mL) were added N, N-diisopropylethylamine (52 mL) and tert-butyl 2,6-diazaspiro[3.3]heptane-2-carboxylate ½ oxalate (24 g), and the mixture was stirred under reflux for 4 hours. After cooling, a half volume of the solvent was removed under reduced pressure from the reaction solution. Ethyl acetate was added to the concentrated solution, and the mixture was washed with water (×1) and brine (×1). The resulting organic layer was dried over anhydrous sodium sulfate, and filtrated, and the solvent was removed under reduced pressure. The residue was purified by silica gel column chromatography (hexane/ethyl acetate) to yield the titled compound (21.2 g).

LC-MS; $[M+H]^+$ 482.3/Rt (min) 1.16 (Analytical condition A)

b) Preparation of 4-(2,6-diazaspiro[3.3]heptan-2-yl)-2-(2,2,2-trifluoroethyl)-5-(trifluoromethyl)thieno[2,3-b]pyridine (Reference example 2)

tert-Butyl 6-{2-(2,2,2-trifluoroethyl)-5-(trifluoromethyl) thieno[2,3-b]pyridin-4-yl}-2,6-diazaspiro[3.3]heptane-2-carboxylate (20 g) was added to TFA (50 mL), and the mixture was stirred at 0° C. for one hour. To the reaction solution was added water, and the mixture was basified with 4 mol/L aqueous sodium hydroxide and extracted with chloroform twice. The obtained organic layer was dried over anhydrous sodium sulfate, and filtrated, and the solvent was removed under reduced pressure. The residue was washed with hexane/ethyl acetate to give Reference example 1 (9.1 g) as a crude product. Further, the filtrate was concentrated under reduced pressure, and the residue was purified by silica gel column chromatography (eluted with chloroform/ethyl acetate, and then with chloroform/methanol) to yield the title compound (5.3 g).

$^1$H-NMR (DMSO-$D_6$) δ: 8.33 (1H, s), 7.72 (1H, s), 4.64 (4H, br s), 4.04 (2H, d, J=23.6, 9.0 Hz), 3.68 (4H, br s).

LC-MS; $[M+H]^+$ 382.2/Rt (min) 0.63 (Analytical condition A)

Reference Examples 3-5

The following Reference examples 3 to 5 were prepared according to a similar method to Reference example 2 by using each corresponding starting compound.

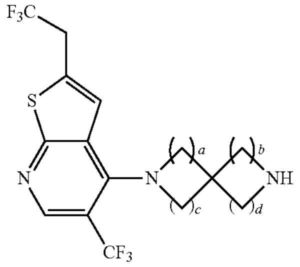

| Reference example | a | b | c | d | LC-MS; [M + H]$^+$/Rt (min) (Analytical condition) |
|---|---|---|---|---|---|
| 3 | 7 | 2 | 1 | 2 | 410.2/0.81 (Analytical condition A) |
| 4 | 1 | 2 | 2 | 1 | 410.2/0.80 (Analytical condition A) |
| 5 | 2 | 1 | 2 | 7 | 410.2/0.91 (Analytical condition A) |

Reference Example 6

4-Chloro-2-(2,2,2-trifluoroethyl)thieno[2,3-b]pyridine-5-carbonitrile

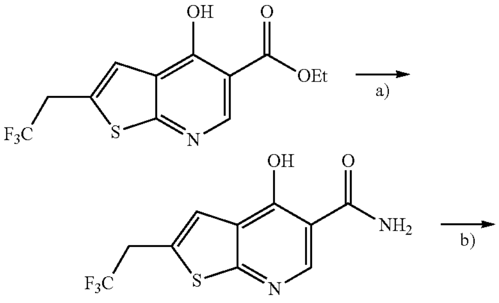

-continued

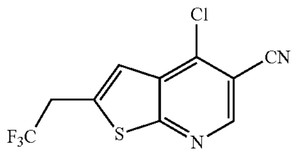

Reference example 6 a) Preparation of 4-hydroxy-2-(2,2,2-trifluoroethyl)thieno[2,3-b]pyridine-5-carboxamide Ethyl 4-hydroxy-2-(2,2,2-trifluoroethyl)thieno[2,3-b]pyridine-5-carboxylate (1.0 g) was added to 8 mol/L ammonia in methanol (10 mL), and the mixture was stirred for 5 hours heating at 100° C. with a microwave device. The obtained reaction solution was concentrated under reduced pressure to give the titled compound (915 mg) as a crude product. The obtained compound was used in the next reaction without purification.

LC-MS; $[M+H]^+$ 277.1/Rt (min) 0.60 (Analytical condition A)

b) Preparation of 4-chloro-2-(2,2,2-trifluoroethyl)thieno[2,3-b]pyridine-5-carbonitrile

Reference Example 6

To a solution of 4-hydroxy-2-(2,2,2-trifluoroethyl)thieno[2,3-b]pyridine-5-carboxamide (915 mg) obtained as a crude product in Step a) in chloroform (10 mL) was added phosphoryl chloride (15.4 mL) at 0° C., and the mixture was stirred at 100° C. for 2 hours. The reaction solution was concentrated under reduced pressure, and the residue was purified by silica gel column chromatography (hexane/ethyl acetate) to yield the titled compound (1.02 g) as a crude product.

LC-MS; $[M+H]^+$ 277.0/Rt (min) 0.97 (Analytical condition A)

Reference Example 7

4-(2,6-Diazaspiro[3.3]heptan-2-yl)-2-(2,2,2-trifluoroethyl)thieno[2,3-b]pyridine-5-carbonitrile

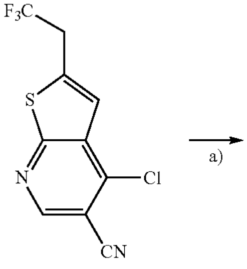

Reference example 6

-continued

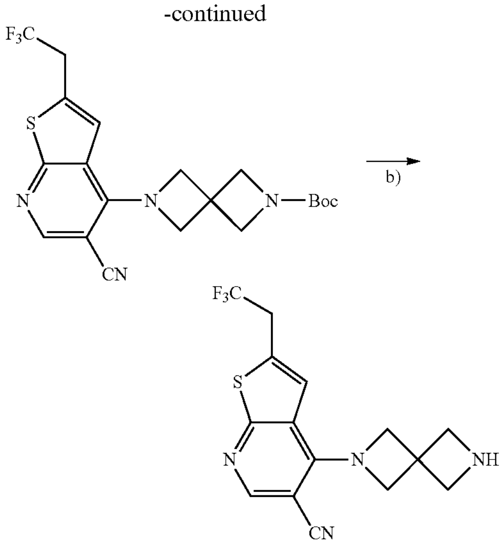

Reference example 7 a) Preparation of tert-butyl 6-[5-cyano-2-(2,2,2-trifluoroethyl)thieno[2,3-b]pyridin-4-yl]-2,6-diazaspiro[3.3]heptane-2-carboxylate To a solution of 4-chloro-2-(2,2,2-trifluoroethyl)thieno[2,3-b]pyridine-5-carbonitrile (1.02 g) in acetonitrile (20 mL) were added tert-butyl 2,6-diazaspiro[3,3] heptane-2-carboxylate 1/2 oxalate (1.79 g) and N, N-diisopropylethylamine (3.22 mL), and the mixture was stirred under reflux for 3 hours. To the reaction solution was added saturated aqueous ammonium chloride, and the mixture was extracted with ethyl acetate. The organic layer was dried over sodium sulfate, and filtrated. The solvent was removed from the filtrate under reduced pressure. The residue was purified by silica gel column chromatography (hexane/ethyl acetate) to yield the title compound (1.18 g).

LC-MS; $[M+H]^+$ 439.3/Rt (min) 1.03 (Analytical condition A)

b) Preparation of 4-(2,6-diazaspiro[3.3]heptan-2-yl)-2-(2,2,2-trifluoroethyl)thieno[2,3-b]pyridine-5-carbonitrile Reference Example 7

To a solution of tert-butyl 6-[5-cyano-2-(2,2,2-trifluoroethyl)thieno[2,3-b]pyridin-4-yl]-2,6-diazaspiro[3.3]heptane-2-carboxylate (1.18 g) in chloroform (18 mL) was added trifluoroacetic acid (3.11 mL) at 0° C., and the mixture was stirred at room temperature for 3 hours. The reaction solution was concentrated under reduced pressure, and the residue was purified by amino silica gel column chromatography (chloroform/methanol) to yield the title compound (866 mg).

$^1$H-NMR (DMSO-$D_6$) δ: 8.27 (1H, s), 7.59 (1H, s), 4.71 (4H, br s), 4.05 (2H, d, J=22.8, 11.6 Hz), 3.63 (4H, br s).

LC-MS; $[M+H]^+$ 339.2/Rt (min) 0.65 (Analytical condition A)

Reference Example 8

4-(2,7-Diazaspiro[3.5]nonan-2-yl)-2-(2,2,2-trifluoroethyl)thieno[2,3-b]pyridine-5-carbonitrile

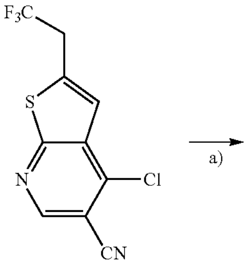

Reference example 6

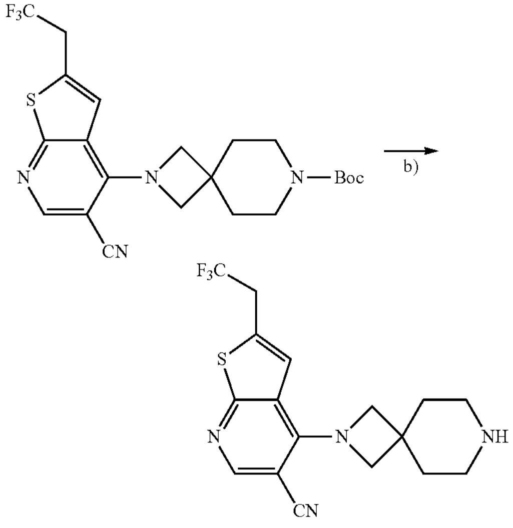

Reference example 8 a) Preparation of tert-butyl 2-[5-cyano-2-(2,2,2-trifluoroethyl)thieno[2,3-b]pyridin-4-yl]-2,7-diazaspiro[3.5]nonane-7-carboxylate To a solution of 4-chloro-2-(2,2,2-trifluoroethyl)thieno[2,3-b]pyridine-5-carbonitrile (0.32 g) in 2-propanol (8 mL) were added tert-butyl 2,7-diazaspiro[3.5]nonane-7-carboxylate (0.31 g) and N, N-diisopropylethylamine (1.20 mL), and the mixture was stirred under reflux for 3 hours. After cooling, the solvent was removed under reduced pressure, and the residue was purified by silica gel column chromatography (hexane/ethyl acetate) to yield the title compound (0.55 g).

LC-MS; $[M+H]^+$ 467.3/Rt (min) 1.12 (Analytical condition A)

b) Preparation of 4-(2,7-diazaspiro[3.5]nonan-2-yl)-2-(2,2,2-trifluoroethyl)thieno[2,3-b]pyridine-5-carbonitrile Reference Example 8

To a solution of tert-butyl 2-[5-cyano-2-(2,2,2-trifluoroethyl)thieno[2,3-b]pyridin-4-yl]-2,7-diazaspiro[3.5]nonane-7-carboxylate (0.55 g) in chloroform (1.5 mL) was added trifluoroacetic acid (1.5 mL), and the mixture was stirred at room temperature for one hour. The reaction solution was concentrated under reduced pressure, diluted with water, basified with 5 mol/L aqueous sodium hydroxide, and extracted with chloroform. The organic layer was washed with brine, dried over anhydrous sodium sulfate, and filtrated. The solvent was removed under reduced pressure to obtain the title compound (0.48 g). The obtained compound was used in the next reaction without purification.

$^1$H-NMR (DMSO-$D_6$) δ: 8.27 (1H, s), 7.65 (1H, s), 4.33 (4H, br s), 4.05 (2H, q, J=11.1 Hz), 2.63 (4H, br m).

LC-MS; $[M+H]^+$ 367.1/Rt (min) 0.67 (Analytical condition A)

Reference Example 9

(1S,3S,4S,5R)-2-(tert-Butoxycarbonyl)-5-hydroxy-2-azabicyclo[2.2.2]octane-3-carboxylic acid

Reference Example 10

(1S,3S,4R,6S)-2-(tert-Butoxycarbonyl)-6-hydroxy-2-azabicyclo[2.2.2]octane-3-carboxylic acid b) Preparation of ethyl (1S,3S,4R)-2-[(1R)-1-phenylethyl]-2-azabicyclo[2.2.2]oct-5-ene-3-carboxylate To a solution of ethyl (2E)-{[(1R)-1-phenylethyl]imino}acetate obtained as a crude product in the above Step a) in dichloromethane (475 mL) were added molecular sieves 4A (powder, 10 g), and the reaction mixture was cooled to −70° C. Trifluoroacetic acid (32 mL) and boron trifluoride-diethyl ether complex (53 mL) were added dropwise to the reaction mixture, and the mixture was stirred for 15 minutes, and 1,3-cyclohexadiene (42 mL) was added dropwise thereto. The reaction mixture was warmed to room temperature, and stirred overnight. To the reaction mixture was added saturated aqueous sodium bicarbonate, and the mixture was extracted with ethyl acetate. The organic layer was washed with saturated aqueous sodium bicarbonate. The organic layer was dried over sodium sulfate and filtered. The solvent was removed under reduced pressure. The residue was purified by silica gel column chromatography (hexane/ethyl acetate) to yield the titled compound (59.4 g).

LC-MS; $[M+H]^+$ 286.2/Rt (min) 0.53 (Analytical condition A)

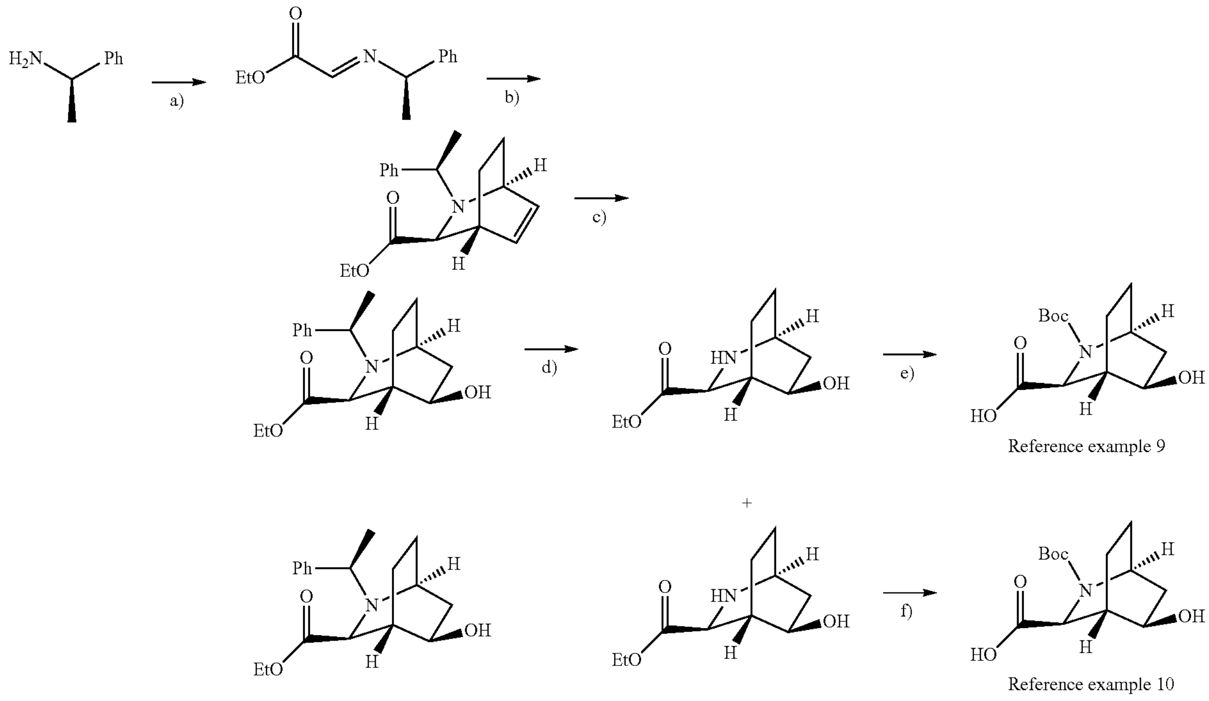

a) Preparation of ethyl (2E)-{[(1R)-1-phenylethyl]imino}acetate

To (R)-1-phenylethylamine (63 mL) was added ethyl oxoacetate (100 mL), and the mixture was stirred at room temperature for one hour, and concentrated under reduced pressure to yield the titled compound as a crude product. The obtained product was used in the next reaction without purification.

c) Preparation of a mixture of ethyl (1S,3S,4S,5R)-5-hydroxy-2-[(1R)-1-phenylethyl]-2-azabicyclo[2.2.2]octane-3-carboxylate and ethyl (1S,3S,4R,6S)-6-hydroxy-2-[(1R)-1-phenylethyl]-2-azabicyclo[2.2.2]octane-3-carboxylate To a solution of ethyl (1S,3S,4R)-2-[(1R)-1-phenylethyl]-2-azabicyclo[2.2.2]oct-5-ene-3-carboxylate (85.5 g) in THF (500 mL) was added dropwise 1.0 mol/L borane-THF complex (300 mL) at 0 to 5° C., and the mixture was stirred at room temperature overnight. To the reaction mixture were added 3 mol/L aqueous sodium hydroxide (62 mL) and 30% aqueous hydrogen peroxide (62 mL) under ice-cooling, and the mixture was stirred for 30 minutes. Aqueous sodium thiosulfate was added thereto, and the mixture was stirred for one hour. To the reaction mixture was added ethyl acetate/chloroform, and the mixture was separated with a separating funnel. The organic layer was washed with brine.

The organic layer was dried over sodium sulfate and filtered, and the solvent was removed under reduced pressure. The residue was purified by silica gel column chromatography (hexane/ethyl acetate) to yield a crude product of the titled compound (51.7 g) as a mixture of regioisomers.

LC-MS; $[M+H]^+$ 304.2/Rt (min) 0.53 (Analytical condition A)

d) Preparation of ethyl (1S,3S,4S,5R)-5-hydroxy-2-azabicyclo[2.2.2]octane-3-carboxylate and ethyl (1S,3S,4R,6S)-6-hydroxy-2-azabicyclo[2.2.2]octane-3-carboxylate To a solution of the mixed product (51.7 g) obtained in the above Step c) in ethanol (500 mL) was added 10% palladium hydroxide (10.2 g), and the mixture was stirred at room temperature under a pressurized hydrogen gas atmosphere (0.3 to 0.4 MPa) for 6 hours. The reaction mixture was filtered, and the filtrate was concentrated under reduced pressure. The residue was purified by silica gel column chromatography (chloroform/methanol) to yield the titled compounds, ethyl (1S,3S,4S,5R)-5-hydroxy-2-azabicyclo[2.2.2]octane-3-carboxylate (19.0 g) and ethyl (1S,3S,4R,6S)-6-hydroxy-2-azabicyclo[2.2.2]octane-3-carboxylate (5.05 g).

Ethyl (1S,3S,4S,5R)-5-hydroxy-2-azabicyclo[2.2.2]octane-3-carboxylate

LC-MS; $[M+H]^+$ 200.2/Rt (min) 0.27 (Analytical condition A)

Ethyl (1S,3S,4R,6S)-6-hydroxy-2-azabicyclo[2.2.2]octane-3-carboxylate

LC-MS; $[M+H]^+$ 200.1/Rt (min) 0.36 (Analytical condition A)

e) Preparation of (1S,3S,4S,5R)-2-(tert-butoxycarbonyl)-5-hydroxy-2-azabicyclo[2.2.2]octane-3-carboxylic acid Reference Example 9

To a solution of ethyl (1S,3S,4S,5R)-5-hydroxy-2-azabicyclo[2.2.2]octane-3-carboxylate (10.48 g) in 1,4-dioxane (153 mL) was added 1 mol/L aqueous sodium hydroxide (238 mL), and the mixture was stirred at room temperature for one hour, and cooled to 0° C. Di-tert-butyl dicarbonate (11.48 g) was added thereto. After stirring for one hour, 1 mol/L hydrochloric acid was added thereto to acidify the reaction mixture. Brine was added thereto, and the mixture was extracted with a mixed solvent of 10% ethanol/chloroform. The organic layer was dried over sodium sulfate. After filtration, the solvent was removed under reduced pressure. The residue was washed with diisopropyl ether, and the mixture was filtered out and dried to yield the titled compound (8.40 g).

$^1$H-NMR (DMSO-$D_6$) δ: 12.55 (1H, br s), 4.86 (1H, br s), 3.96-3.81 (3H, m), 2.09-1.69 (4H, m), 1.59-1.49 (1H, m), 1.36 (3H, s), 1.31 (6H, s), 1.29-1.17 (2H, m).

f) Preparation of (1S,3S,4R,6S)-2-(tert-butoxycarbonyl)-6-hydroxy-2-azabicyclo[2.2.2]octane-3-carboxylic acid Reference Example 10

The titled compound (1.60 g) was prepared according to a similar method to Step e) by using ethyl (1S,3S,4R,6S)-6-hydroxy-2-azabicyclo[2.2.2]octane-3-carboxylate (5.05 g).

$^1$H-NMR (DMSO-$D_6$) δ: 4.09-4.05 (3H, m), 2.28-2.20 (1H, m), 2.18-2.05 (2H, m), 1.91-1.80 (1H, m), 1.63-1.50 (3H, m), 1.45 (3H, s), 1.40 (6H, s).

Reference Example 11

(1S,3S,4S,5R)-2-(tert-Butoxycarbonyl)-5-hydroxy-2-azabicyclo[2.2.1]heptane-3-carboxylic acid

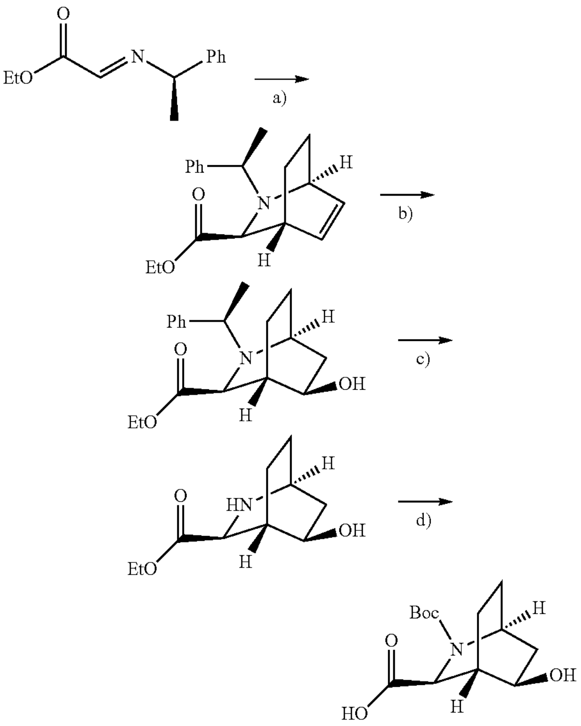

Reference example 11 a) Preparation of ethyl (1S,3S,4R)-2-[(1R)-1-phenylethyl]-2-azabicyclo[2.2.1]hept-5-ene-3-carboxylate The title compound (10.8 g) was prepared according to a similar method to Step b) in Reference example 9 and Reference example 10 by using ethyl (2E)-{[(1R)-1-phenylethyl]imino}acetate (12.0 g) and cyclopentadiene (4.92 mL).

LC-MS; $[M+H]^+$ 272.2/Rt (min) 0.54 (Analytical condition A)

b) Preparation of ethyl (1S,3S,4S,5R)-5-hydroxy-2-[(1R)-1-phenylethyl]-2-azabicyclo[2.2.1]heptane-3-carboxylate The title compound (7.49 g) was prepared according to a similar method to Step c) in Reference example 9 and Reference example 10 by using ethyl (1S,3S,4R)-2-[(1R)-1-phenylethyl]-2-azabicyclo[2.2.1]hept-5-ene-3-carboxylate (10.8 g).

LC-MS; $[M+H]^+$ 290.2/Rt (min) 0.46 (Analytical condition A)

c) Preparation of ethyl (1S,3S,4S,5R)-5-hydroxy-2-azabicyclo[2.2.1]heptane-3-carboxylate The title compound (2.89 g) was prepared according to a similar method to Step d) in Reference example 9 and Reference example 10 by using ethyl (1S,3S,4S,5R)-5-hydroxy-2-[(1R)-1-phenylethyl]-2-azabicyclo[2.2.1]heptane-3-carboxylate (7.49 g).

LC-MS; $[M+H]^+$ 186.1/Rt (min) 0.27 (Analytical condition A)

d) Preparation of (1S,3S,4S,5R)-2-(tert-butoxycarbonyl)-5-hydroxy-2-azabicyclo[2.2.1]heptane-3-carboxylic acid Reference Example 11

The title compound (980 mg) was prepared according to a similar method to Step e) in Reference example 9 by using ethyl (1S,3S,4S,5R)-5-hydroxy-2-azabicyclo[2.2.1]heptane-3-carboxylate (2.88 g).

$^1$H-NMR (DMSO-$D_6$) δ: 4.99 (1H, br s), 4.11-3.95 (1H, m), 3.95-3.82 (1H, m), 3.48-3.40 (1H, m), 2.41-2.31 (1H, m), 1.90-1.75 (1H, m), 1.69-1.49 (2H, m), 1.45-1.19 (10H, m).

Reference Example 12

3-Benzyl 2-tert-butyl (1S,3S,4S)-5-oxo-2-azabicyclo[2.2.2]octane-2,3-dicarboxylate

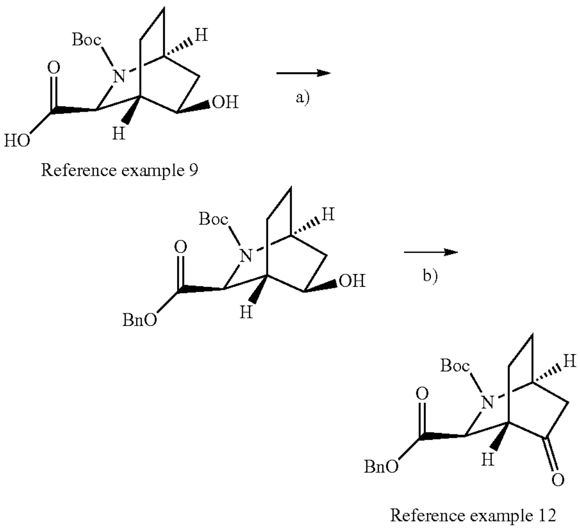

a) Preparation of 3-benzyl 2-tert-butyl (1S,3S,4S,5R)-5-hydroxy-2-azabicyclo[2.2.2]octane-2,3-dicarboxylate To a solution of (1S,3S,4S,5R)-2-(tert-butoxycarbonyl)-5-hydroxy-2-azabicyclo[2.2.2]octane-3-carboxylic acid (28.0 g) and potassium carbonate (28.5 g) in acetonitrile (300 mL) was added benzyl bromide (12.3 mL) at room temperature, and the mixture was stirred overnight. The reaction mixture was concentrated under reduced pressure, and water was added to the residue. The mixture was extracted with ethyl acetate. The organic layer was dried over sodium sulfate and filtered, and the solvent was removed under reduced pressure. The residue was purified by silica gel column chromatography (hexane/ethyl acetate) to yield the title compound (33.1 g).

LC-MS; $[M+H]^+$ 362.3/Rt (min) 0.95 (Analytical condition A)

b) Preparation of 3-benzyl 2-tert-butyl (1S,3S,4S)-5-oxo-2-azabicyclo[2.2.2]octane-2,3-dicarboxylate (Reference example 12)

To a solution of 3-benzyl 2-tert-butyl (1S,3S,4S,5R)-5-hydroxy-2-azabicyclo[2.2.2]octane-2,3-dicarboxylate (33.0 g) in dichloromethane (400 mL) was added Dess-Martin reagent (46.5 g) at room temperature, and the mixture was stirred at room temperature overnight. To the reaction mixture was added aqueous sodium thiosulfate and aqueous sodium bicarbonate, and the mixture was extracted with chloroform. The organic layer was dried over sodium sulfate and filtered, and the solvent was removed under reduced pressure. The residue was purified by silica gel column chromatography (hexane/ethyl acetate) to yield the titled compound (33.8 g) as a crude product.

LC-MS; $[M+H]^+$ 360.2/Rt (min) 1.02 (Analytical condition A)

$^1$H-NMR ($CDCl_3$) δ: 7.38-7.28 (5H, m), 5.33-5.05 (2H, m), 4.66-4.42 (2H, m), 2.80-2.69 (1H, m), 2.59-2.45 (1H, m), 2.36-2.16 (2H, m), 1.82-1.62 (3H, m), 1.45 (2.5H, s), 1.31 (6.5H, s).

Reference Example 13

(1S,3S,4R)-2-(tert-Butoxycarbonyl)-5-methylidene-2-azabicyclo[2.2.2]octane-3-carboxylic acid

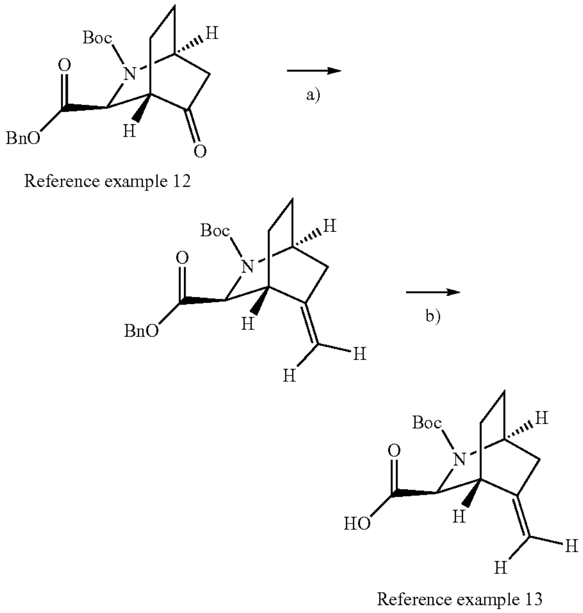

a) Preparation of 3-benzyl 2-tert-butyl (1S,3S,4R)-5-methylidene-2-azabicyclo[2.2.2]octane-2,3-dicarboxylate To a solution of 3-benzyl 2-tert-butyl (1S,3S,4S)-5-oxo-2-azabicyclo[2.2.2]octane-2,3-dicarboxylate (3.0 g) in THF (30 mL) was added Petasis reagent (5% solution of THF/toluene, 35 g) at room temperature, and the mixture was stirred at 95° C. for 5 hours. The temperature was backed to room temperature, and Petasis reagent (5% solution of THF/toluene, 10 g) was added. The mixture was heated under After cooling, diethyl ether was added reflux at 130° C. thereto, a precipitated orange solid was filtered off, and the filtrate was concentrated. The residue was purified by silica gel column chromatography (hexane/ethyl acetate) to yield the title compound (1.9 g).

LC-MS; $[M+H]^+$ 358.0/Rt (min) 1.21 (Analytical condition A)

b) Preparation of (1S,3S,4R)-2-(tert-butoxycarbonyl)-5-methylidene-2-azabicyclo[2.2.2]octane-3-carboxylic acid

Reference Example 13

To a solution of 3-benzyl 2-tert-butyl (1S,3S,4R)-5-methylidene-2-azabicyclo[2.2.2]octane-2,3-dicarboxylate (1.9 g) in methanol (30 mL) was added aqueous sodium hydroxide (5 mol/L, 5.3 mL), and the mixture was stirred under heat at 50° C. for 5 hours. After the reaction mixture was cooled to room temperature, it was neutralized with 1 mol/L aqueous hydrochloric acid and extracted with chloroform. The organic layer was dried over sodium sulfate and filtered, and the solvent was removed under reduced pressure. The residue was purified by silica gel column chromatography (chloroform/methanol) to yield the title compound (0.99 g).

LC-MS; $[M+H]^+$ 268.0/Rt (min) 0.83 (Analytical condition A)

Reference Example 14

(1S,3S,4R)-2-(tert-Butoxycarbonyl)-5-($^2H_2$)methylidene-2-azabicyclo[2.2.2]octane-3-carboxylic acid

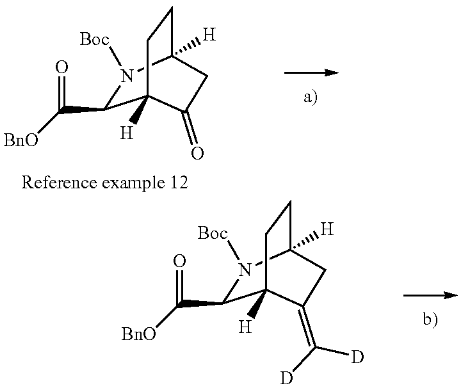

-continued

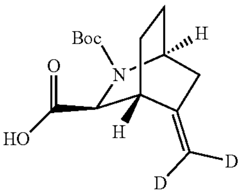

Reference example 14 a) Preparation of 3-benzyl 2-tert-butyl (1S,3S,4R)-5-($^2H_2$)methylidene-2-azabicyclo[2.2.2]octane-2,3-dicarboxylate To a suspension of ($^2H_3$)methyl(triphenyl)phosphanium iodide (2.83 g) in THF (14 mL) was added dropwise n-butyl lithium (1.57 mol/L hexane solution, 3.54 mL) at −78° C., and the mixture was stirred at 0° C. for 1.5 hours. The reaction was cooled again to −78° C., and 3-benzyl 2-tert-butyl (1S,3S,4S)-5-oxo-2-azabicyclo[2.2.2]octane-2,3-dicarboxylate (1.0 g) was added portionwise. The mixture was stirred for 5 hours. The reaction was backed to room temperature, quenched by addition of saturated aqueous ammonium chloride, and the mixture was extracted with ethyl acetate. The obtained organic layer was washed with water and brine, dried over anhydrous sodium sulfate, and filtered. The solvent was removed under reduced pressure. The residue was purified by silica gel column chromatography (hexane/ethyl acetate) to yield the title compound (0.46 g).

LC-MS; $[M+H]^+$ 360.4/Rt (min) 1.22 (Analytical condition A)

b) Preparation of (1S,3S,4R)-2-(tert-butoxycarbonyl)-5-($^2H_2$)methylidene-2-azabicyclo[2.2.2]octane-3-carboxylic acid (Reference example 14)

To a solution of 3-benzyl 2-tert-butyl (1S,3S,4R)-5-($^2H_2$)methylidene-2-azabicyclo[2.2.2]octane-2,3-dicarboxylate in methanol (10 mL) were added aqueous sodium hydroxide (5 mol/L, 1.8 mL) and water (2 mL), and the mixture was stirred at 50° C. for 4 hours. The reaction mixture was cooled to room temperature, and the methanol was removed under reduced pressure. The resulting solution was extracted with chloroform. The aqueous layer was acidified with 1 mol/L hydrochloric acid, and extracted with chloroform. The organic layer was washed with brine, dried over anhydrous sodium sulfate, and filtered. The solvent was removed under reduced pressure to yield the titled compound (0.31 g). The obtained compound was used without purification in the next reaction.

LC-MS; $[M+H]^+$ 270.2/Rt (min) 0.89 (Analytical condition A) $^1$H-NMR (DMSO-$D_6$) δ: 12.60 (1H, br s), 4.17-3.95. (total 2H, m), 2.74-2.60 (total 1H, m), 2.60-2.43 (total 1H, m), 2.34-2.23 (total 1H, m), 1.94-1.54 (total 3H, m), 1.54-1.41 (total 1H, m), 1.41-1.19 (total 9H, m).

Reference Example 15

(1S,3S,4R)-2-(tert-butoxycarbonyl)-6-methylidene-2-azabicyclo[2.2.2]octane-3-carboxylic acid

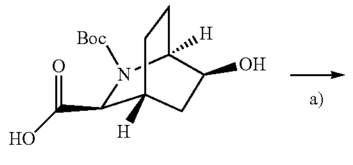

Reference example 10

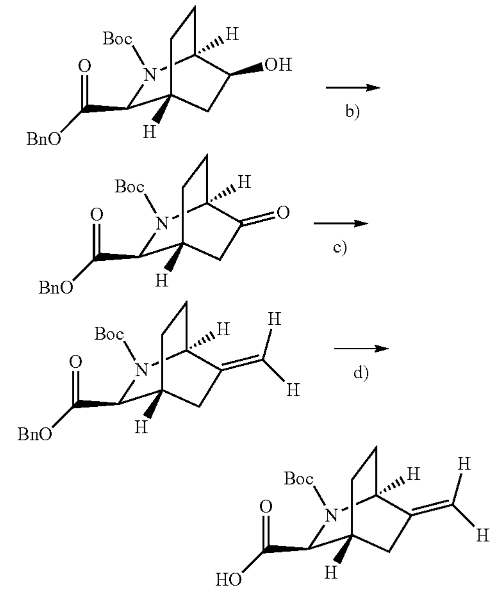

Reference example 15 a) Preparation of 3-benzyl 2-tert-butyl (1S,3S,4R,6S)-6-hydroxy-2-azabicyclo[2.2.2]octane-2,3-dicarboxylate To a solution of (1S,3S,4R,6S)-2-(tert-butoxycarbonyl)-6-hydroxy-2-azabicyclo[2.2.2]octane-3-carboxylic acid (80.0 g) and potassium carbonate (122 g) in DMF (550 mL) was added benzyl bromide (101 g), and the mixture was stirred at room temperature overnight. The reaction solution was diluted with ethyl acetate, was washed with water (×3) and brine (×1), dried over anhydrous sodium sulfate, and concentrated. The residue was purified by silica gel column chromatography (hexane/ethyl acetate) to yield the title compound (65.5 g).

LC-MS; $[M+H]^+$ 362.1/Rt (min) 0.95 (Analytical condition A)

b) Preparation of 3-benzyl 2-tert-butyl (1S,3S,4R)-6-oxo-2-azabicyclo[2.2.2]octane-2,3-dicarboxylate To a solution of 3-benzyl 2-tert-butyl (1S,3S,4R,6S)-6-hydroxy-2-azabicyclo[2.2.2]octane-2,3-dicarboxylate (10.0 g) in dichloromethane (100 mL) was added Dess-Martin reagent (15.3 g) at ice temperature, and the mixture was stirred at room temperature overnight. To the reaction mixture was added aqueous sodium thiosulfate and aqueous sodium bicarbonate, and the mixture was extracted with chloroform. The organic layer was dried over sodium sulfate and filtered, and the solvent was removed under reduced pressure. The residue was purified by silica gel column chromatography (hexane/ethyl acetate) to yield the title compound (6.0 g).

LC-MS; $[M+H]^+$ 360.1/Rt (min) 1.02 (Analytical condition A)

c) Preparation of 3-benzyl 2-tert-butyl (1S,3S,4R)-6-methylidene-2-azabicyclo[2.2.2]octane-2,3-dicarboxylate To a solution of 3-benzyl 2-tert-butyl (1S,3S,4R)-6-oxo-2-azabicyclo[2.2.2]octane-2,3-dicarboxylate (4.0 g) in THE (40 mL) was added Petasis reagent (5% solution of THF/toluene, 60 g) at room temperature, and the mixture was stirred at 95° C. for 5 hours. The temperature was backed to room temperature, and Petasis reagent (5% solution of THF/toluene, 70 g) was added. The mixture was heated under reflux at 130° C. After cooling, diethyl ether was added thereto, a precipitated orange solid was filtered off, and the filtrate was concentrated. The residue was purified by silica gel column chromatography (hexane/ethyl acetate) to yield the title compound (2.12 g).

LC-MS; $[M+H]^+$ 358.0/Rt (min) 1.29 (Analytical condition A)

d) Preparation of (1S,3S,4R)-2-(tert-butoxycarbonyl)-6-methylidene-2-azabicyclo[2.2.2]octane-3-carboxylic acid Reference Example 15

To a solution of 3-benzyl 2-tert-butyl (1S,3S,4R)-6-methylidene-2-azabicyclo[2.2.2]octane-2,3-dicarboxylate (2.1 g) in methanol (15 mL) was added 2.5 mol/L aqueous sodium hydroxide (6.7 mL), and the mixture was stirred at 50° C. for 5 hours. After cooling, the reaction solution was diluted with water, and extracted with diethyl ether 3 times. The aqueous layer was acidified with 1 mol/L aqueous hydrochloric acid, and extracted with extracted with chloroform. The organic layer was dried over anhydrous sodium sulfate and filtered, and the solvent was removed under reduced pressure to yield the title compound (1.4 g).

LC-MS; $[M+H]^+$ 268.0/Rt (min) 0.82 (Analytical condition A)

Reference Example 16

(1S,3S,4R)-2-(tert-Butoxycarbonyl)-5-methylidene-2-azabicyclo[2.2.1]heptane-3-carboxylic acid

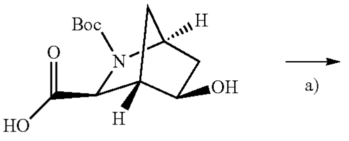

Reference example 11

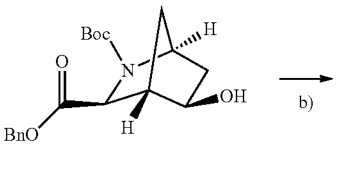

-continued

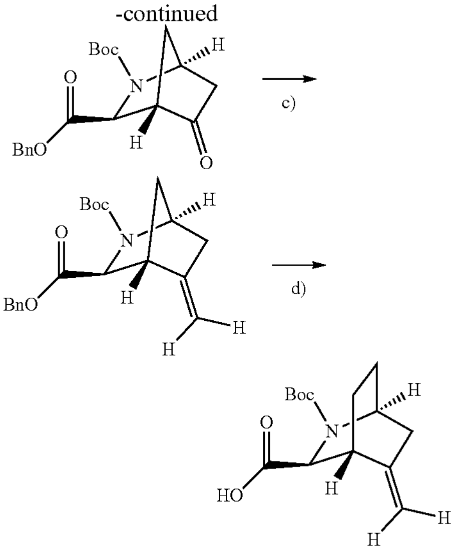

Reference example 16 a) Preparation of 3-benzyl 2-tert-butyl (1S,3S,4S,5R)-5-hydroxy-2-azabicyclo[2.2.1]heptane-2,3-dicarboxylate The title compound (1.73 g) was prepared according to a similar method to Step a) in Reference example 12 by using (1S,3S,4S,5R)-2-(tert-butoxycarbonyl)-5-hydroxy-2-azabicyclo[2.2.1]heptane-3-carboxylic acid (1.5 g).

LC-MS; $[M+H]^+$ 348.2/Rt (min) 0.92 (Analytical condition A)

b) Preparation of 3-benzyl 2-tert-butyl (1S,3S,4S)-5-oxo-2-azabicyclo[2.2.1]heptane-2,3-dicarboxylate The title compound (1.40 g) was prepared according to a similar method to Step b) in Reference example 12 by using 3-benzyl 2-tert-butyl (1S,3S,4S,5R)-5-hydroxy-2-azabicyclo[2.2.1]heptane-2,3-dicarboxylate (1.73 g).

LC-MS; $[M+H]^+$ 346.2/Rt (min) 1.01 (Analytical condition A)

c) Preparation of 3-benzyl 2-tert-butyl (1S,3S,4R)-5-methylidene-2-azabicyclo[2.2.1]heptane-2,3-dicarboxylate The title compound (1.10 g) was prepared according to a similar method to Step a) in Reference example 13 by using 3-benzyl 2-tert-butyl (1S,3S,4S)-5-oxo-2-azabicyclo[2.2.1]heptane-2,3-dicarboxylate (1.40 g).

LC-MS; $[M+H]^+$ 344.2/Rt (min) 1.18 (Analytical condition A)

d) Preparation of (1S,3S,4R)-2-(tert-butoxycarbonyl)-5-methylidene-2-azabicyclo[2.2.1]heptane-3-carboxylic acid

Reference Example 16

The title compound (0.69 g) was prepared according to a similar method to Step b) in Reference example 13 by using 3-benzyl 2-tert-butyl (1S,3S,4R)-5-methylidene-2-azabicyclo[2.2.1]heptane-2,3-dicarboxylate (1.10 g).

LC-MS; $[M+H]^+$ 254.3/Rt (min) 0.82 (Analytical condition A)

Reference Example 17

3-Benzyl 2-tert-butyl (1S,3S,4S,6E)-6-(cyclopropylmethylidene)-5-oxo-2-azabicyclo[2.2.2]octane-2,3-dicarboxylate

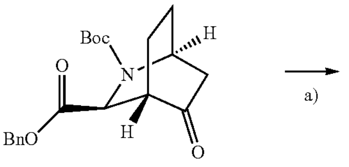

Reference example 12

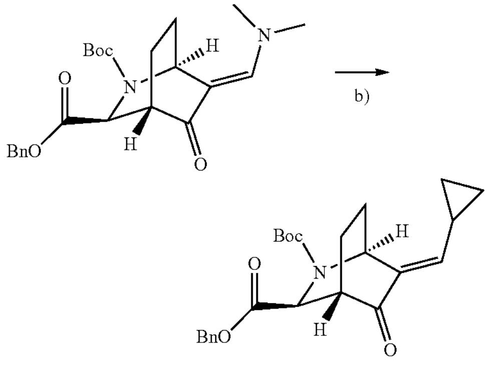

Reference example 17 a) Preparation of 3-benzyl 2-tert-butyl (1S,3S,4S,6E)-6-[(dimethylamino)methylidene]-5-oxo-2-azabicyclo[2.2.2]octane-2,3-dicarboxylate To a solution of 3-benzyl 2-tert-butyl (1S,3S,4S)-5-oxo-2-azabicyclo[2.2.2]octane-2,3-dicarboxylate (33.8 g) in N,N-dimethylformamide (180 mL) was added Bredereck reagent (32.8 g), and the mixture was stirred with heating at 100° C. for 2 hours. The reaction solution was concentrated under reduced pressure, and the residue was purified by silica gel column chromatography (hexane/ethyl acetate) to yield the titled compound (39.0 g) as a crude product.

LC-MS; $[M+H]^+$ 415.4/Rt (min) 0.95 (Analytical condition A)

b) Preparation of 3-benzyl 2-tert-butyl (1S,3S,4S,6E)-6-(cyclopropylmethylidene)-5-oxo-2-azabicyclo[2.2.2]octane-2,3-dicarboxylate (Reference example 17)

A solution of 3-benzyl 2-tert-butyl (1S,3S,4S,6E)-6-[(dimethylamino)methylidene]-5-oxo-2-azabicyclo[2.2.2]octane-2,3-dicarboxylate (39.0 g) in tetrahydrofuran (300 mL) was cooled to 0° C., and cyclopropylmagnesium bromide (0.5 mol/L tetrahydrofuran solution, 245 mL) was added dropwise thereto. The mixture was stirred at room temperature for 6 hours. To the reaction mixture was added saturated aqueous ammonium chloride, and the mixture was extracted with ethyl acetate. The organic layer was dried over sodium sulfate and filtered, and the solvent was removed under reduced pressure. The residue was purified by silica gel column chromatography (hexane/ethyl acetate) to yield the title compound (32.3 g).

LC-MS; $[M+H]^+$ 412.4/Rt (min) 1.16 (Analytical condition A)

$^1$H-NMR ($CDCl_3$) δ: 7.39-7.27 (5H, m), 5.91 (1H, t, J=11.0 Hz), 5.38-5.04 (3H, m), 4.50-4.36 (1H, m), 2.90-2.76 (1H, m), 2.37-2.22 (1H, m), 1.82-1.59 (4H, m), 1.44 (3H, s), 1.31 (6H, s), 1.09-0.95 (2H, m), 0.73-0.58 (2H, m).

Reference Example 18

3-Benzyl 2-tert-butyl (1S,3S,4S)-6-(cyclopropylmethyl)-5-hydroxy-2-azabicyclo[2.2.2]octane-2,3-dicarboxylate

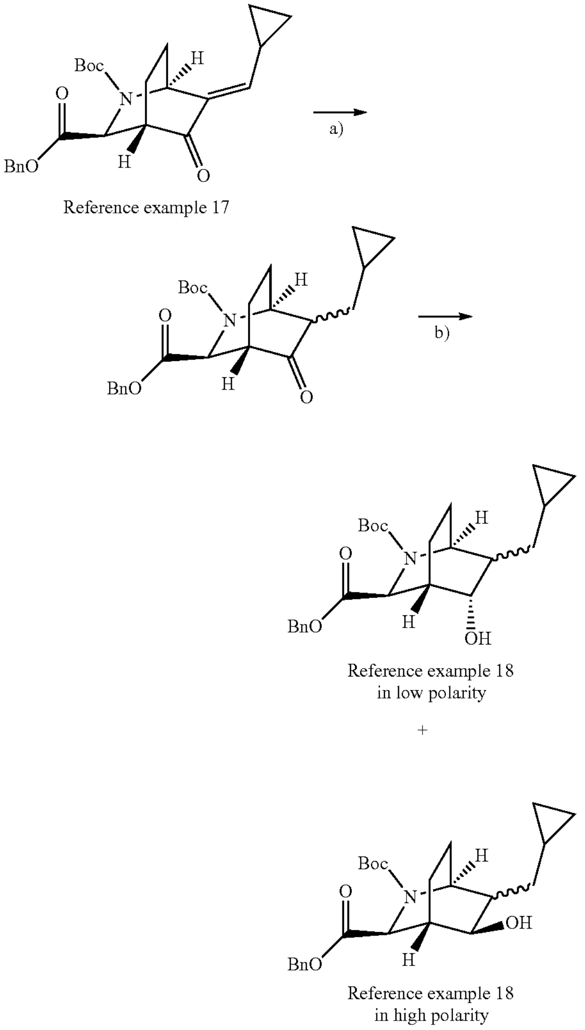

Reference example 17
Reference example 18 in low polarity
+
Reference example 18 in high polarity a) Preparation of 3-benzyl 2-tert-butyl (1S,3S,4S)-6-(cyclopropylmethyl)-5-oxo-2-azabicyclo[2.2.2]octane-2,3-dicarboxylate To a solution of 3-benzyl 2-tert-butyl (1S,3S,4S,6E)-6-(cyclopropylmethylidene)-5-oxo-2-azabicyclo[2.2.2]octane-2,3-dicarboxylate (32.3 g) in tetrahydrofuran (300 mL) was added copper (I) hydride triphenylphosphine hexamer (38.5 g), and the mixture was stirred at room temperature for 12 hours. The reaction mixture was filtered through Celite, and the filtrate was concentrated under reduced pressure. The residue was purified by silica gel column chromatography (hexane/ethyl acetate) to yield the title compound (23.2 g) as a mixture of stereoisomers.

LC-MS; $[M+H]^+$ 414.1/Rt (min) 1.22 (Analytical condition A)

b) Preparation of 3-benzyl 2-tert-butyl (1S,3S,4S)-6-(cyclopropylmethyl)-5-hydroxy-2-azabicyclo[2.2.2]octane-2,3-dicarboxylate (Reference example 18)

A solution of 3-benzyl 2-tert-butyl (1S,3S,4S)-6-(cyclopropylmethyl)-5-oxo-2-azabicyclo[2.2.2]octane-2,3-dicarboxylate (23.2 g) in methanol (200 mL) was cooled to 0° C., sodium borohydride (2.12 g) was added thereto, and the mixture was stirred for one hour. The reaction solution was concentrated under reduced pressure, and the residue was purified by silica gel column chromatography (hexane/ethyl acetate) to yield the titled compound as a stereoisomer mixture in low polarity (9.3 g) and a stereoisomer mixture in high polarity (10.2 g).

The stereoisomer mixture in low polarity: 3-benzyl 2-tert-butyl (1S,3S,4S,5S)-6-(cyclopropylmethyl)-5-hydroxy-2-azabicyclo[2.2.2]octane-2,3-dicarboxylate LC-MS; $[M+H]^+$ 416.1/Rt (min) 1.13 (Analytical condition A) The stereoisomer mixture in high polarity: 3-benzyl 2-tert-butyl (1S,3S,4S,5R)-6-(cyclopropylmethyl)-5-hydroxy-2-azabicyclo[2.2.2]octane-2,3-dicarboxylate LC-MS; $[M+H]^+$ 416.1/Rt (min) 1.01 (Analytical condition A)

Reference Example 19

(1S,3S,4S,5R,6R)-2-(tert-Butoxycarbonyl)-6-(cyclopropylmethyl)-5-fluoro-2-azabicyclo[2.2.2]octane-3-carboxylic acid

Reference Example 20

(1S,3S,4S,5R,6S)-2-(tert-butoxycarbonyl)-6-(cyclopropylmethyl)-5-fluoro-2-azabicyclo[2.2.2]octane-3-carboxylic acid

Reference Example 21

(1S,3S,4S,5S,6R)-2-(tert-Butoxycarbonyl)-6-(cyclopropylmethyl)-5-fluoro-2-azabicyclo[2.2.2]octane-3-carboxylic acid

Reference Example 22

(1S,3S,4S,5S,6S)-2-(tert-Butoxycarbonyl)-6-(cyclopropylmethyl)-5-fluoro-2-azabicyclo[2.2.2]octane-3-carboxylic acid

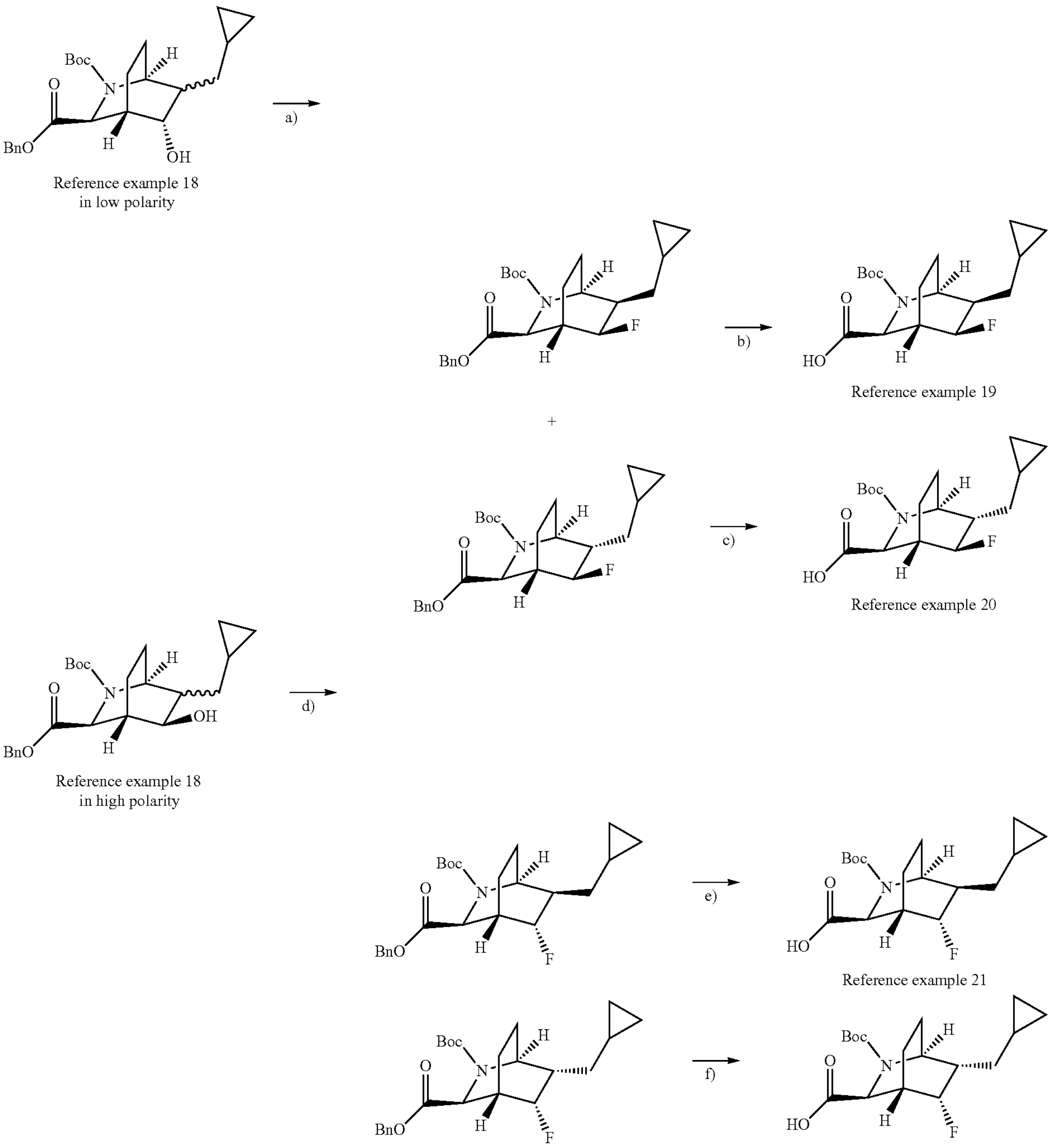

Reference example 18 in low polarity

Reference example 19

Reference example 20

Reference example 18 in high polarity

Reference example 21

Reference example 22 a) Preparation of 3-benzyl 2-tert-butyl (1S,3S,4S,5R,6R)-6-(cyclopropylmethyl)-5-fluoro-2-azabicyclo[2.2.2]octane-2,3-dicarboxylate and 3-benzyl 2-tert-butyl (1S,3S,4S,5R,6S)-6-(cyclopropylmethyl)-5-fluoro-2-azabicyclo[2.2.2]octane-2,3-dicarboxylate A solution of 3-benzyl 2-tert-butyl (1S,3S,4S,5S)-6-(cyclopropylmethyl)-5-hydroxy-2-azabicyclo[2.2.2]octane-2,3-dicarboxylate (9.3 g) which is the stereoisomer mixture in low polarity in Reference example 18, in dichloromethane (80 mL) was cooled to 0° C., and (diethylamino) sulfur trifluoride (5.91 mL) was added thereto. The mixture was stirred at room temperature overnight. To the reaction mixture was added saturated aqueous sodium bicarbonate, and the mixture was extracted with chloroform. The organic layer was dried over sodium sulfate and filtered, and the solvent was removed under reduced pressure. The residue was purified by silica gel column chromatography (hexane/ethyl acetate) to yield 3-benzyl 2-tert-butyl (1S,3S,4S,5R,6R)-6-(cyclopropylmethyl)-5-fluoro-2-azabicyclo[2.2.2]octane-2,3-dicarboxylate (3.6 g) and 3-benzyl 2-tert-butyl (1S,3S,4S,5R,6S)-6-(cyclopropylmethyl)-5-fluoro-2-azabicyclo[2.2.2]octane-2,3-dicarboxylate (3.7 g). 3-Benzyl 2-tert-butyl (1S,3S,4S,5R,6R)-6-(cyclopropylmethyl)-5-fluoro-2-azabicyclo[2.2.2]octane-2,3-dicarboxylate LC-MS; $[M+H]^+$ 418.4/Rt (min) 1.29 (Analytical condition A) 3-Benzyl 2-tert-butyl (1S,3S,4S,5R,6S)-6-(cyclopropylmethyl)-5-fluoro-2-azabicyclo[2.2.2]octane-2,3-dicarboxylate LC-MS; $[M+H]^+$ 418.4/Rt (min) 1.35 (Analytical condition A) b) Preparation of (1S,3S,4S,5R,6R)-2-(tert-butoxycarbonyl)-6-(cyclopropylmethyl)-5-fluoro-2-azabicyclo[2.2.2]octane-3-carboxylic acid (Reference example 19)

To a solution of 3-benzyl 2-tert-butyl (1S,3S,4S,5R,6R)-6-(cyclopropylmethyl)-5-fluoro-2-azabicyclo[2.2.2]octane-2,3-dicarboxylate (3.6 g) and ammonium formate (5.4 g) in tetrahydrofuran (50 mL) was added palladium hydroxide/carbon (1.2 g), and the mixture was heated under reflux for 3 hours. The reaction mixture was cooled to room temperature, filtered through Celite, and the filtrate was concentrated under reduced pressure to yield the titled compound (2.8 g).

LC-MS; $[M-H]^-$ 326.4/Rt (min) 0.95 (Analytical condition A)

c) Preparation of (1S,3S,4S,5R,6S)-2-(tert-butoxycarbonyl)-6-(cyclopropylmethyl)-5-fluoro-2-azabicyclo[2.2.2]octane-3-carboxylic acid (Reference example 20)

The titled compound (108 mg) was prepared as a crude product according to a similar method to Step b) in Reference example 19 by using 3-benzyl 2-tert-butyl (1S,3S,4S,5R,6S)-6-(cyclopropylmethyl)-5-fluoro-2-azabicyclo[2.2.2]octane-2,3-dicarboxylate (108 mg).

LC-MS; $[M-H]^-$ 326.4/Rt (min) 0.95 (Analytical condition A)

d) Preparation of 3-benzyl 2-tert-butyl (1S,3S,4S,5S,6R)-6-(cyclopropylmethyl)-5-fluoro-2-azabicyclo[2.2.2]octane-2,3-dicarboxylate and 3-benzyl 2-tert-butyl (1S,3S,4S,5S,6S)-6-(cyclopropylmethyl)-5-fluoro-2-azabicyclo[2.2.2]octane-2,3-dicarboxylate 3-Benzyl 2-tert-butyl (1S,3S,4S,5S,6R)-6-(cyclopropylmethyl)-5-fluoro-2-azabicyclo[2.2.2]octane-2,3-dicarboxylate (86 mg) and 3-benzyl 2-tert-butyl (1S,3S,4S,5S,6S)-6-(cyclopropylmethyl)-5-fluoro-2-azabicyclo[2.2.2]octane-2,3-dicarboxylate (152 mg) were prepared according to a similar method to Step a) of Reference example 19 by using 3-benzyl 2-tert-butyl (1S,3S,4S,5R)-6-(cyclopropylmethyl)-5-hydroxy-2-azabicyclo[2.2.2]octane-2,3-dicarboxylate (363 mg), which is the stereoisomer mixture in high polarity in Reference example 18.

3-Benzyl 2-tert-butyl (1S,3S,4S,5S,6R)-6-(cyclopropylmethyl)-5-fluoro-2-azabicyclo[2.2.2]octane-2,3-dicarboxylate LC-MS; $[M+H]^+$ 418.4/Rt (min) 1.27 (Analytical condition A) 3-Benzyl 2-tert-butyl (1S,3S,4S,5S,6S)-6-(cyclopropylmethyl)-5-fluoro-2-azabicyclo[2.2.2]octane-2,3-dicarboxylate LC-MS; $[M+H]^+$ 418.4/Rt (min) 1.29 (Analytical condition A)

e) Preparation of (1S,3S,4S,5S,6R)-2-(tert-butoxycarbonyl)-6-(cyclopropylmethyl)-5-fluoro-2-azabicyclo[2.2.2]octane-3-carboxylic acid (Reference example 21)

The titled compound (73 mg) was prepared as a crude product according to a similar method to Step b) in Reference example 19 by using 3-benzyl 2-tert-butyl (1S,3S,4S,5S,6R)-6-(cyclopropylmethyl)-5-fluoro-2-azabicyclo[2.2.2]octane-2,3-dicarboxylate (82 mg).

LC-MS; $[M-H]^-$ 326.4/Rt (min) 0.94 (Analytical condition A)

f) Preparation of (1S,3S,4S,5S,6S)-2-(tert-butoxycarbonyl)-6-(cyclopropylmethyl)-5-fluoro-2-azabicyclo[2.2.2]octane-3-carboxylic acid (Reference example 22)

The titled compound (140 mg) was prepared as a crude product according to a similar method to Step b) in Reference example 19 by using 3-benzyl 2-tert-butyl (1S,3S,4S,5S,6S)-6-(cyclopropylmethyl)-5-fluoro-2-azabicyclo[2.2.2]octane-2,3-dicarboxylate (147 mg).

LC-MS; $[M-H]^-$ 326.3/Rt (min) 0.95 (Analytical condition A)

Reference Example 23

(1S,3S,4R,6S)-2-(tert-Butoxycarbonyl)-6-(cyclopropylmethyl)-2-azabicyclo[2.2.2]octane-3-carboxylic acid Reference Example 24

(1S,3S,4R,6R)-2-(tert-Butoxycarbonyl)-6-(cyclopropylmethyl)-2-azabicyclo[2.2.2]octane-3-carboxylic acid

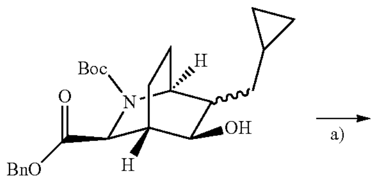

Reference example 18
in high polarity

-continued

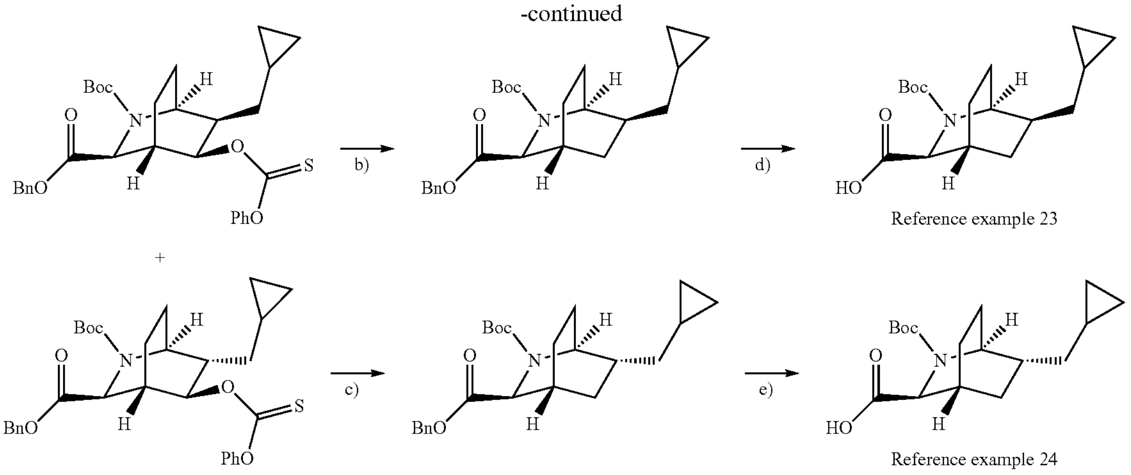

a) Preparation of 3-benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate and 3-benzyl 2-tert-butyl (1S,3S,4S,5R,6S)-6-(cyclopropylmethyl)-5-[(phenoxycarbonothioyl)oxy]-2-azabicyclo[2.2.2]octane-2,3-dicarboxylate A solution of 3-benzyl 2-tert-butyl (1S,3S,4S,5R)-6-(cyclopropylmethyl)-5-hydroxy-2-azabicyclo[2.2.2]octane-2,3-dicarboxylate (7.3 g) which is the stereoisomer mixture in high polarity in Reference example 18, in acetonitrile (50 mL) was cooled to 0° C., and 4-(dimethylamino)pyridine (8.6 g) and phenyl chlorothionoformate (4.74 mL) were added thereto. The mixture was stirred at 50° C. for 12 hours. The reaction mixture was cooled to room temperature, brine was added thereto, and the mixture was extracted with ethyl acetate. The organic layer was dried over magnesium sulfate and filtered, and the solvent was removed unde reduced pressure. The residue was purified by silica gel column chromatography (hexane/ethyl acetate) to yield a crude product (1.80 g) of 3-benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate and a crude product (7.90 g) of 3-benzyl 2-tert-butyl (1S,3S,4S,5R,6S)-6-(cyclopropylmethyl)-5-[(phenoxycarbonothioyl)oxy]-2-azabicyclo[2.2.2]octane-2,3-dicarboxylate.

3-Benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate LC-MS; $[M+H]^+$ 552.2/Rt (min) 1.42 (Analytical condition A)

3-Benzyl 2-tert-butyl (1S,3S,4S,5R,6S)-6-(cyclopropylmethyl)-5-[(phenoxycarbonothioyl)oxy]-2-azabicyclo[2.2.2]octane-2,3-dicarboxylate LC-MS; $[M+H]^+$ 552.2/Rt (min) 1.45 (Analytical condition A)

b) Preparation of 3-benzyl 2-tert-butyl (1S,3S,4R,6S)-6-(cyclopropylmethyl)-2-azabicyclo[2.2.2]octane-2,3-dicarboxylate A solution of 3-benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate (1.80 g) in toluene (50 mL) was cooled to 0° C., and tris(trimethylsilyl)silane (5.03 mL) and 2,2'-azobis(2-methylpropionitrile) (0.11 g) were added thereto. The mixture was stirred with heating at 50° C. for 5 hours. The reaction mixture was cooled to room temperature, brine was added thereto, and the mixture was extracted with ethyl acetate. The organic layer was dried over magnesium sulfate and filtered, and the solvent was removed under reduced pressure. The residue was purified by silica gel column chromatography (hexane/ethyl acetate) to yield the title compound (0.80 g).

LC-MS; $[M+H]^+$ 400.2/Rt (min) 1.38 (Analytical condition A)

c) Preparation of 3-benzyl 2-tert-butyl (1S,3S,4R,6R)-6-(cyclopropylmethyl)-2-azabicyclo[2.2.2]octane-2,3-dicarboxylate The title compound (5.50 g) was prepared according to a similar method to Step b) in Reference example 23 by using 3-benzyl 2-tert-butyl (1S,3S,4S,5R,6S)-6-(cyclopropylmethyl)-5-[(phenoxycarbonothioyl)oxy]-2-azabicyclo[2.2.2]octane-2,3-dicarboxylate (7.90 g).

LC-MS; $[M+H]^+$ 400.2/Rt (min) 1.40 (Analytical condition A)

d) Preparation of (1S,3S,4R,6S)-2-(tert-butoxycarbonyl)-6-(cyclopropylmethyl)-2-azabicyclo[2.2.2]octane-3-carboxylic acid (Reference example 23)

The title compound (3.90 g) was prepared according to a similar method to Step b) in Reference example 13 by using 3-benzyl 2-tert-butyl (1S,3S,4R,6S)-6-(cyclopropylmethyl)-2-azabicyclo[2.2.2]octane-2,3-dicarboxylate (5.50 g).

LC-MS; $[M+H]^+$ 310.2/Rt (min) 1.02 (Analytical condition A)

e) Preparation of (1S,3S,4R,6R)-2-(tert-butoxycarbonyl)-6-(cyclopropylmethyl)-2-azabicyclo[2.2.2]octane-3-carboxylic acid (Reference example 24)

The titled compound (980 mg) was prepared as a crude product according to a similar method to Step b) in Reference example 13 by using 3-benzyl 2-tert-butyl (1S,3S,4R, 6R)-6-(cyclopropylmethyl)-2-azabicyclo[2.2.2]octane-2,3-dicarboxylate (1.20 g).

LC-MS; $[M+H]^+$ 310.2/Rt (min) 1.04 (Analytical condition A)

Reference Example 25

(1S,3S,4S,5S,6E)-2-(tert-Butoxycarbonyl)-6-(cyclopropylmethylidene)-5-hydroxy-2-azabicyclo[2.2.2]octane-3-carboxylic acid

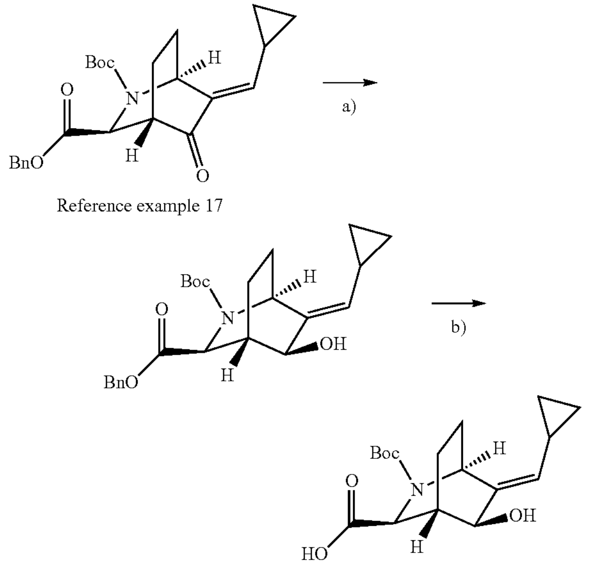

Reference example 17

Reference example 25 a) Preparation of 3-benzyl 2-tert-butyl (1S,3S,4S,5S,6E)-6-(cyclopropylmethylidene)-5-hydroxy-2-azabicyclo[2.2.2]octane-2,3-dicarboxylate A solution of 3-benzyl 2-tert-butyl (1S,3S,4S,6E)-6-(cyclopropylmethylidene)-5-oxo-2-azabicyclo[2.2.2]octane-2,3-dicarboxylate (750 mg) in methanol (10 mL) was cooled to 0° C., and cerium (III) chloride heptahydrate (883 mg) and sodium borohydride (90 mg) were added thereto. The mixture was stirred for one hour. To the reaction mixture was added brine, and the mixture was extracted with ethyl acetate. The organic layer was dried over magnesium sulfate, and filtrated. The solvent was removed under reduced pressure. The residue was purified by silica gel column chromatography (hexane/ethyl acetate) to yield the title compound (630 mg).

LC-MS; $[M+H]^+$ 414.4/Rt (min) 1.11 (Analytical condition A)

b) Preparation of (1S,3S,4S,5S,6E)-2-(tert-butoxycarbonyl)-6-(cyclopropylmethylidene)-5-hydroxy-2-azabicyclo[2.2.2]octane-3-carboxylic acid (Reference example 25)

A solution of 3-benzyl 2-tert-butyl (1S,3S,4S,5S,6E)-6-(cyclopropylmethylidene)-5-hydroxy-2-azabicyclo[2.2.2]octane-2,3-dicarboxylate (630 mg) in methanol (10 mL) was cooled to 0° C., and aqueous sodium hydroxide (2 mol/L, 3.8 mL) was added thereto. The mixture was stirred at 50° C. for 5 hours. The reaction solution was cooled to room temperature, it was neutralized with 1 mol/L aqueous hydrochloric acid and extracted with chloroform. The organic layer was dried over sodium sulfate and filtered, and the solvent was removed under reduced pressure. The residue was purified by silica gel column chromatography (chloroform/methanol) to yield the title compound (400 mg).

LC-MS; $[M+H]^+$ 324.3/Rt (min) 0.77 (Analytical condition A)

Reference Example 26 tert-Butyl (1S,3S,4S,5R,6E)-6-(cyclopropylmethylidene)-5-fluoro-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate

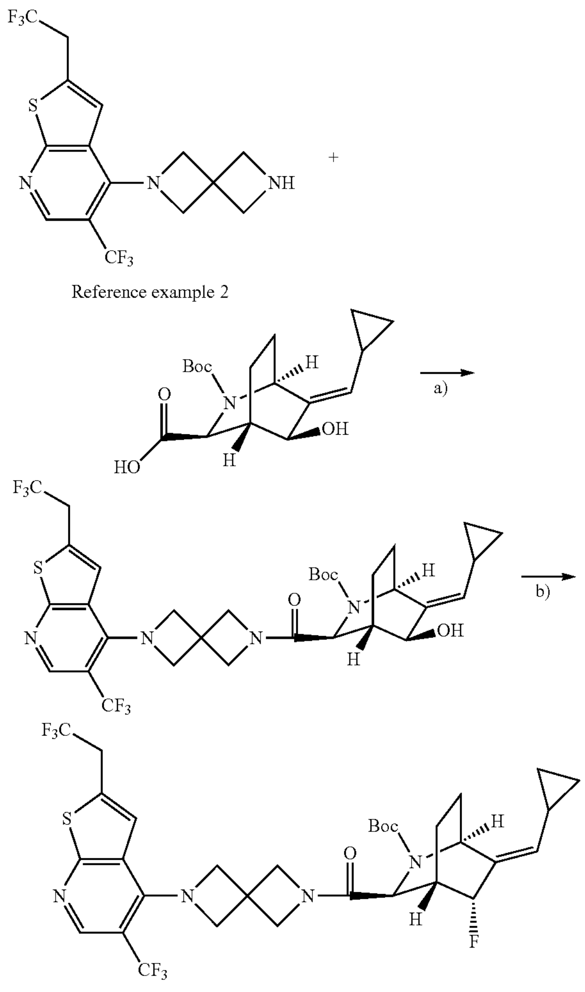

Reference example 2

Reference example 26 a) Preparation of tert-butyl (1S,3S,4S,5S,6E)-6-(cyclopropylmethylidene)-5-hydroxy-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate To a solution of 4-(2,6-diazaspiro[3.3]heptan-2-yl)-2-(2,2,2-trifluoroethyl)-5-(trifluoromethyl)thieno[2,3-b]pyridine (293 mg) prepared in Reference example 2 in methylene chloride (20 mL) were added (1S,3S,4S,5S,6E)-2-(tert-butoxycarbonyl)-6-(cyclopropylmethylidene)-5-hydroxy-2-azabicyclo[2.2.2]octane-3-carboxylic acid (250 mg) prepared in Reference example 25, HATU (584 mg), and triethylamine (0.54 mL), and the mixture was stirred at room temperature for 2 hours. To the reaction solution was added ethyl acetate, and the mixture was washed with water (×2), and brine (×1). The obtained organic layer was dried over magnesium sulfate, and filtrated. The solvent was removed from the filtrate under reduced pressure. The residue was purified by silica gel column chromatography (hexane/ethyl acetate) to yield the title compound (190 mg).

LC-MS; $[M+H]^+$ 687.5/Rt (min) 1.10 (Analytical condition A)

b) Preparation of tert-butyl (1S,3S,4S,5R,6E)-6-(cyclopropylmethylidene)-5-fluoro-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (Reference example 26)

The title compound (60.0 mg) was prepared according to a similar method to Step d) in Reference example 21 or 22 by using tert-butyl (1S,3S,4S,5S,6E)-6-(cyclopropylmethylidene)-5-hydroxy-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (190 mg).

LC-MS; $[M+H]^+$ 689.5/Rt (min) 1.07 (Analytical condition A)

Reference Examples 27-51

The following Reference examples 27 to 51 were prepared according to similar methods to Reference example 26 by using each corresponding starting compound.

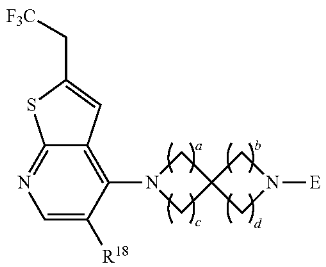

| Reference example | $R^{18}$ | a | b | c | d | E | LC-MS: $[M+H]^+$ Rt (min) (Analytical condition) |
|---|---|---|---|---|---|---|---|
| 27 | $CF_3$ | 1 | 1 | 1 | 1 | 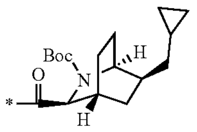 | 673.1/1.32 (Analytical condition A) |
| 28 | CN | 1 | 1 | 1 | 1 | 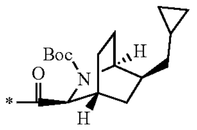 | 630.1/1.23 (Analytical condition A) |
| 29 | $CF_3$ | 1 | 1 | 1 | 1 | 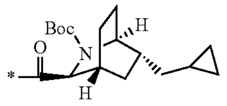 | 673.1/1.32 (Analytical condition A) |
| 30 | CN | 1 | 1 | 1 | 1 | 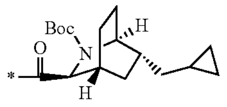 | 630.0/1.11 (Analytical condition A) |
| 31 | $CF_3$ | 1 | 1 | 1 | 1 | 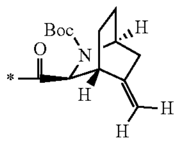 | 631.1/1.18 (Analytical condition A) |
| 32 | CN | 1 | 1 | 1 | 1 | 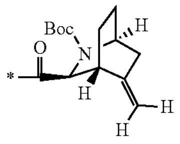 | 588.1/1.10 (Analytical condition A) |

-continued

| Reference example | $R^{18}$ | a | b | c | d | E | LC-MS: $[M + H]^+$ Rt (min) (Analytical condition) |
|---|---|---|---|---|---|---|---|
| 33 | $CF_3$ | 1 | 1 | 1 | 1 | 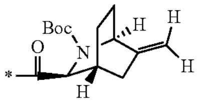 | 631.1/1.16 (Analytical condition A) |
| 34 | CN | 1 | 1 | 1 | 1 | 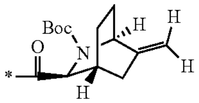 | 588.1/1.13 (Analytical condition A) |
| 35 | CN | 1 | 1 | 1 | 1 | 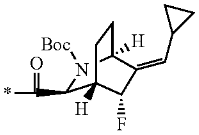 | 646.5/1.02 (Analytical condition A) |
| 36 | $CF_3$ | 1 | 1 | 1 | 1 | 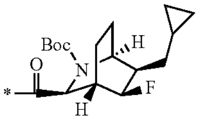 | 691.2/1.23 (Analytical condition A) |
| 37 | CN | 1 | 1 | 1 | 1 | 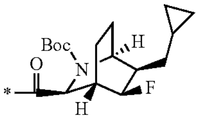 | 648.4/1.16 (Analytical condition A) |
| 38 | $CF_3$ | 1 | 1 | 1 | 1 | 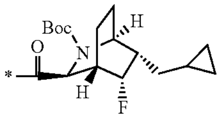 | 691.2/1.22 (Analytical condition A) |
| 39 | CN | 1 | 1 | 1 | 1 | 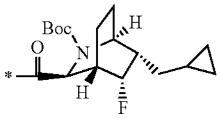 | 648.5/1.15 (Analytical condition A) |
| 40 | $CF_3$ | 1 | 1 | 1 | 1 | 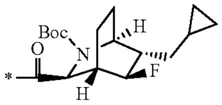 | 691.1/1.24 (Analytical condition A) |
| 41 | $CF_3$ | 1 | 1 | 1 | 1 | 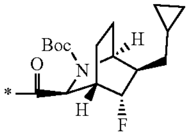 | 691.2/1.23 (Analytical condition A) |
| 42 | $CF_3$ | 1 | 1 | 1 | 1 | 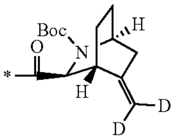 | 633.3/1.19 (Analytical condition A) |
| 43 | $CF_3$ | 1 | 1 | 1 | 1 | 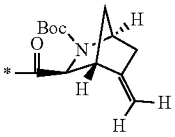 | 617.4/1.15 (Analytical condition A) |

-continued
| Reference example | $R^{18}$ | a | b | c | d | E | LC-MS: $[M + H]^+$ Rt (min) (Analytical condition) |
|---|---|---|---|---|---|---|---|
| 44 | $CF_3$ | 1 | 2 | 2 | 1 | 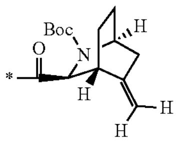 | 659.4/1.25 (Analytical condition A) |
| 45 | $CF_3$ | 2 | 1 | 2 | 1 | 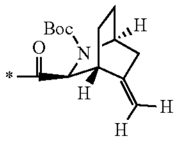 | 659.4/1.34 (Analytical condition A) |
| 46 | $CF_3$ | 1 | 2 | 1 | 2 | 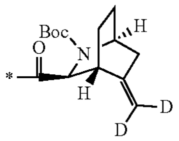 | 661.4/1.24 (Analytical condition A) |
| 47 | $CF_3$ | 1 | 2 | 1 | 2 | 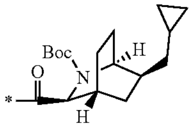 | 701.5/1.13 (Analytical condition A) |
| 48 | $CF_3$ | 1 | 2 | 1 | 2 | 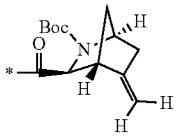 | 645.4/1.20 (Analytical condition A) |
| 49 | CN | 1 | 2 | 1 | 2 | 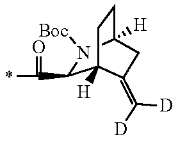 | 618.4/1.13 (Analytical condition A) |
| 50 | CN | 1 | 2 | 1 | 2 | 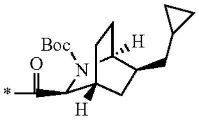 | 658.5/1.24 (Analytical condition A) |
| 51 | CN | 1 | 2 | 1 | 2 | 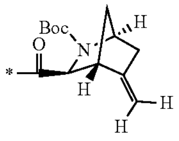 | 602.4/1.10 (Analytical condition A) |

Reference Example 52

(2,7-Diazaspiro[3.5]nonan-7-yl)[(1S,3S,4R)-5-methylidene-2-azabicyclo[2.2.2]octan-3-yl]methanone

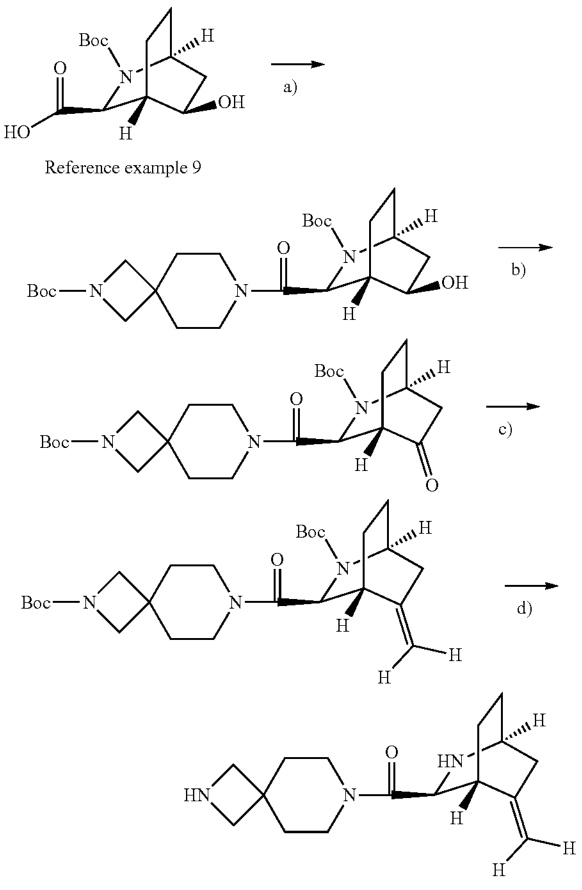

Reference example 52 a) Preparation of tert-butyl 7-[(1S,3S,4S,5R)-2-(tert-butoxycarbonyl)-5-hydroxy-2-azabicyclo[2.2.2]octane-3-carbonyl]-2,7-diazaspiro[3.5]nonane-2-carboxylate To a solution of the compound prepared in Reference example 9 (20.0 g) in dichloromethane (200 mL) were added tert-butyl 2,7-diazaspiro[3.5]nonane-2-carboxylate (18.4 g), WSCI·HCl (18.4 g), HOBt (13.0 g), and N, N-diisopropylethylamine (16.7 mL) at room temperature, and the mixture was stirred at room temperature overnight. To the reaction solution was added chloroform, and the mixture was washed sequentially with saturated aqueous ammonium chloride, water, and then brine. The organic layer was dried over anhydrous sodium sulfate, and filtrated. The solvent was removed under reduced pressure, and the residue was crystallized with diisopropyl ether/hexane (1/1) to yield the title compound (33.9 g).

LC-MS; $[M+H]^+$ 480.1/Rt (min) 0.83 (Analytical condition A)

b) Preparation of tert-butyl 7-[(1S,3S,4S)-2-(tert-butoxycarbonyl)-5-oxo-2-azabicyclo[2.2.2]octane-3-carbonyl]-2,7-diazaspiro[3.5]nonane-2-carboxylate To a solution of oxalyl chloride (8.94 mL) in dichloromethane (300 mL) was added dropwise dimethyl sulfoxide (11.1 mL) under a nitrogen atmosphere at −78° C., and the mixture was stirred at −78° C. for 30 minutes. A solution of tert-butyl 7-[(1S,3S,4S,5R)-2-(tert-butoxycarbonyl)-5-hydroxy-2-azabicyclo[2.2.2]octane-3-carbonyl]-2,7-diazaspiro[3.5]nonane-2-carboxylate (25.0 g) in dichloromethane (100 mL) was added dropwise thereto at −65° C. or below, and the mixture was stirred at −78° C. for another hour. Triethylamine (36.3 mL) was added dropwise thereto at −78° C., and the mixture was backed to room temperature and stirred for additional 30 minutes. The reaction mixture was diluted with chloroform, and washed sequentially with saturated aqueous ammonium chloride, water, and then brine. The resulting organic layer was dried over anhydrous sodium, and filtrated. The solvent was removed from the filtrate under reduced pressure, and the residue was crystallized with hexane to yield the titled compound (22.5 g).

LC-MS; $[M+H]^+$ 478.1/Rt (min) 0.90 (Analytical condition A)

c) Preparation of tert-butyl 7-[(1S,3S,4R)-2-(tert-butoxycarbonyl)-5-methylidene-2-azabicyclo[2.2.2]octane-3-carbonyl]-2,7-diazaspiro[3.5]nonane-2-carboxylate To a suspension of methyl(triphenyl)phosphonium bromide (25.2 g) in THF (300 mL) was added potassium tert-butoxide (7.9 g) with ice-cooling, and the mixture was stirred for one hour. To the reaction mixture was added tert-butyl 7-[(1S,3S,4S)-2-(tert-butoxycarbonyl)-5-oxo-2-azabicyclo[2.2.2]octane-3-carbonyl]-2,7-diazaspiro[3.5]nonane-2-carboxylate (22.5 g), and the mixture was stirred at room temperature for 2 hours. Methyl(triphenyl)phosphonium bromide (8.4 g) and potassium tert-butoxide (2.6 g) were further added thereto, and the mixture was stirred at room temperature for another hour. The reaction mixture was diluted with ethyl acetate, and washed with water and brine. The resulting organic layer was dried over anhydrous sodium sulfate, and filtrated. The solvent was removed under reduced pressure, and the residue was purified by silica gel column chromatography (hexane/ethyl acetate) to yield the title compound (24.2 g).

LC-MS; $[M+H]^+$ 476.1/Rt (min) 1.09 (Analytical condition A)

d) Preparation of (2,7-diazaspiro[3.5]nonan-7-yl)[(1S,3S,4R)-5-methylidene-2-azabicyclo[2.2.2]octan-3-yl]methanone (Reference example 52)

To a solution of tert-butyl 7-[(1S,3S,4R)-2-(tert-butoxycarbonyl)-5-methylidene-2-azabicyclo[2.2.2]octane-3-carbonyl]-2,7-diazaspiro[3.5]nonane-2-carboxylate (1.4 g) in chloroform (5 mL) was added TFA (5 mL), and the mixture was stirred at 40° C. for 4 hours. The reaction solution was concentrated under reduced pressure, diluted with water, and extracted with chloroform. The aqueous layer was basified with 5 mol/L aqueous sodium hydroxide, and extracted with chloroform. The organic layer was washed with brine, dried over anhydrous sodium sulfate, and filtrated. The solvent was removed from the filtrate under reduced pressure to obtain the title compound (0.8 g). The obtained compound was used in the next reaction without purification.

LC-MS; $[M+H]^+$ 276.2/Rt (min) 0.31 (Analytical condition A) 1H-NMR (DMSO-$D_6$) δ: 4.90 (1H, m), 4.71 (1H, m), 3.83 (1H, s), 3.51 (1H, m), 3.34 (1H, m), 3.31-3.12 (total 6H, m), 2.99 (1H, m), 2.45 (1H, m), 2.31-2.20 (total 2H, m), 1.71-1.48 (total 6H, br m), 1.46-1.34 (2H, br m).

Example 1

[(1S,3S,4R,6S)-6-(Cyclopropylmethyl)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone Exmaple 1

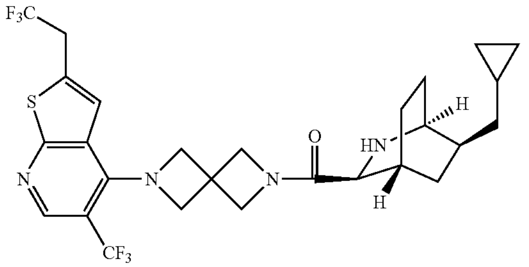

To a solution of the compound prepared in Reference example 27 (80 mg) in dichloromethane (9.0 mL) was added TFA (1.0 mL) at room temperature, and the mixture was stirred at room temperature for 3 hours. The solvent was removed under reduced pressure, and the residue was purified by amine silica gel chromatography (ethyl acetate/methanol) to yield Example 1 (47.0 mg).

LC-MS; $[M+H]^+$ 573.6/Rt (min) 1.77 (Analytical condition B)

$^1$H-NMR ($CDCl_3$) δ: 8.47 (1H, s), 7.38 (1H, s), 4.77 (4H, brs), 4.47-4.23 (4H, m), 3.75 (1H, s), 3.67 (2H, dd, J=10.4, 20.1 Hz), 2.91 (1H, s), 2.20-2.18 (1H, m), 2.08-2.02 (1H, m), 1.75-1.59 (4H, m), 1.38-1.31 (2H, m), 1.24-1.12 (2H, m), 0.73-0.67 (1H, m), 0.47-0.44 (2H, m), 0.09-0.03 (2H, m).

Examples 2-26

The following Examples 2 to 26 were prepared according to similar methods to Example 1 by using each corresponding starting compound.

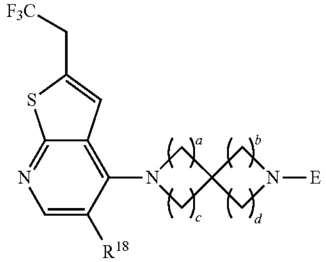

| Example | $R^{18}$ | a | b | c | d | E | LC-MS: $[M + H]^+$ or $[M + 2H]^{2+}$/Rt (min) (Analytical condition) 1H-NMR: Chemical Shift |
|---|---|---|---|---|---|---|---|
| 2 | CN | 1 | 1 | 1 | 1 | 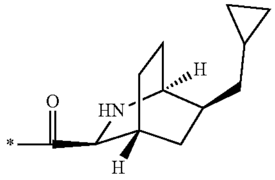 | 530.0/1.75 (Analytical condition B) |
| 3 | $CF_3$ | 1 | 1 | 1 | 1 | 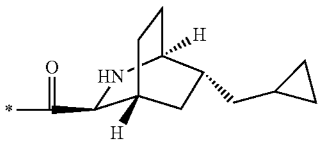 | 287.6/0.95 (Analytical condition B) $^1$H-NMR ($CDCl_3$) δ: 8.46 (1H, s), 7.38 (1H, s), 4.75 (4H, brs), 4.44-4.22 ( 4H, m), 3.69-3.61 (3H, m), 2.91 (1H, s), 2.03-1.87 (2H, m), 1.80-1.76 (2H, m), 1.65-1.29 (5H, m), 0.92-0.89 (1H, m), 0.74-0.70 (1H, m), 0.45-0.43 (2H, m), 0.10-0.07 (2H, m). |
| 4 | CN | 1 | 1 | 1 | 1 | 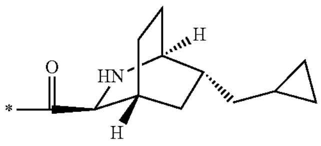 | 265.6/1.11 (Analytical condition A) $^1$H-NMR ($CDCl_3$) δ: 8.32 (1H, s), 7.29 (1H, s), 4.91-4.85 (4H, m), 4.51-4.24 (4H, m), 3.69-3.61 (3H, m), 2.94 (1H, s), 2.04-1.88 (2H, m), 1.84-1.76 (2H, m), 1.65-1.31 (6H, m), 0.74- |

-continued

| Example | $R^{18}$ | a | b | c | d | E | LC-MS: $[M + H]^+$ or $[M + 2H]^{2+}$/Rt (min) (Analytical condition) 1H-NMR: Chemical Shift |
|---|---|---|---|---|---|---|---|
| | | | | | | | 0.71 (1H, m), 0.45-0.43 (2H, m), 0.11-0.08 (2H, m). |
| 5 | $CF_3$ | 1 | 1 | 1 | 1 | 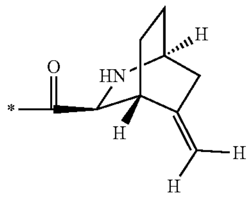 | 531.2/1.67 (Analytical condition B) $^1$H-NMR (DMSO-$D_6$) δ: 8.34 (1H, s), 7.67 (1H, s), 4.92 (1H, br s), 4.76-4.69 (5H, m), 4.43 (2H, dd, J = 15, 9 Hz), 4.15 (2H, q, J = 11 Hz), 4.05 (2H, q, J = 11 Hz), 3.59 (1H, br s), 3.02 (1H, br s), 2.60-2.42 (2H, m), 2.32-2.25 (1H, m), 1.72-1.56 (2H, m), 1.48-1.35 (2H, m). |
| 6 | CN | 1 | 1 | 1 | 1 | 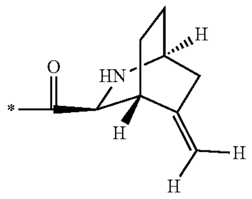 | 245.1/0.94 (Analytical condition A) $^1$H-NMR (DMSO-$D_6$) δ: 8.31 (1H, s), 7.54 (1H, s), 4.91-4.80 (5H, m), 4.71 (1H, s), 4.49-4.42 (2H, m), 4.21-4.03 (4H, m), 3.56 (1H, s), 2.98 (1H, s), 2.49-2.36 (1H, m), 2.34 (2H, dd, J = 13.4, 16.5 Hz), 1.68-1.63 (2H, m), 1.46-1.40 (2H, m). |
| 7 | $CF_3$ | 1 | 1 | 1 | 1 | 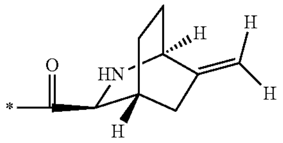 | 531.2/1.67 (Analytical condition B) $^1$H-NMR (DMSO-$D_6$) δ: 8.34 (1H, s), 7.68 (1H, s), 4.77 (1H, br d), 4.71 (4H, br d), 4.62 (1H, br d), 4.45 (2H, dd, J = 38, 10 Hz), 4.15-4.00 (4H, m), 3.49 (1H, br m), 3.14 (1H, br m), 2.36 (1H, m), 1.98 (1H, m), 1.78 (1H, m), 1.58-1.42 (2H, m), 1.38-1.22 (2H, m). |
| 8 | CN | 1 | 1 | 1 | 1 | 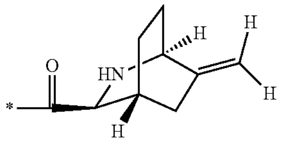 | 488.0/1.67 (Analytical condition B) $^1$H-NMR (DMSO-$D_6$) δ: 8.31 (1H, s), 7.55 (1H, s), 4.82-4.78 (5H, m), 4.64 (1H, d, J = 2.0 Hz), 4.47 (2H, dd, J = 9.8, 28.0 Hz), 4.18-4.02 (4H, m), 3.51 (1H, s), 3.15 (1H, s), 2.43-2.32 (2H, m), 1.99 (1H, s), 1.82-1.77 (1H, m) 1.56-1.44 (2H, m), 1.38-1.32 (1H, m). |

-continued

| Example | $R^{18}$ | a | b | c | d | E | LC-MS: $[M + H]^+$ or $[M + 2H]^{2+}$/Rt (min) (Analytical condition) 1H-NMR: Chemical Shift |
|---|---|---|---|---|---|---|---|
| 9 | $CF_3$ | 1 | 1 | 1 | 1 | 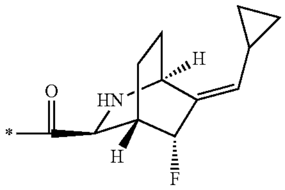 | 295.8/0.76 (Analytical condition A) |
| 10 | CN | 1 | 1 | 1 | 1 | 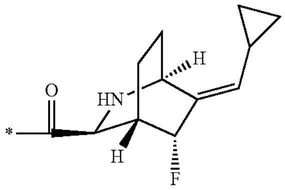 | 273.7/0.81 (Analytical condition A) |
| 11 | $CF_3$ | 1 | 1 | 1 | 1 | 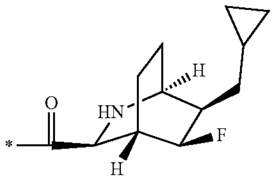 | 296.2/0.82 (Analytical condition A) $^1$H-NMR ($CDCl_3$) δ: 8.47 (1H, s), 7.37 (1H, s), 4.77 (4H, brs), 4.51-4.46 (1.5H, m), 4.39-4.35 (2.5H, m), 4.27-4.24 (1H, m), 4.00 (1H, s), 3.64 (2H, dd, J = 10.4, 20.1 Hz), 3.00 (1H, s), 2.28-2.01 (4H, m), 1.76-1.65 (2H, m), 1.50-1.35 (2H, m), 0.80-0.76 (1H, m), 0.52-0.50 (2H, m), 0.12-0.07 (2H, m). |
| 12 | CN | 1 | 1 | 1 | 1 | 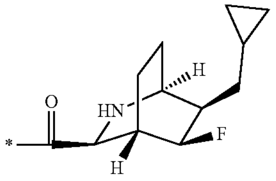 | 548.4/1.027 (Analytical condition A) $^1$H-NMR ($CDCl_3$) δ: 8.28 (1H, s), 7.19 (1H, s), 4.94-4.78 (4H, m), 4.52-4.19 (5H, m), 3.99 (1H, s), 3.60 (2H, q, J = 10.0 Hz), 3.02 (1H, s), 2.34-1.84 (3H, m), 1.79-1.55 (2H, m), 1.53-1.28 (3H, m), 1.21-1.08 (1H, m), 0.82-0.69 (1H, m), 0.56-0.40 (2H, m), 0.13-0.02 (2H, m). |
| 13 | $CF_3$ | 1 | 1 | 1 | 1 | 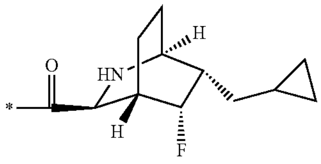 | 296.2/0.83 (Analytical condition A) $^1$H-NMR ($CDCl_3$) δ: 8.47 (1H, s), 7.37 (1H, s), 5.02-5.00 (0.5H, m), 4.89-4.87 (0.5H, m), 4.78-4.75 (4H, m), 4.50-4.23 (4H, m), 3.95 (1H, m), 3.64 (2H, dd, J = 10.4, 20.1 Hz), 2.99 (1H, s), 2.09-1.74 (5H, m), 1.43-1.23 (3H, m), 0.80-0.76 (1H, m), 0.50-0.45 (2H, m) 0.15-0.09 (2H, m). |

-continued

| Example | $R^{18}$ | a | b | c | d | E | LC-MS: $[M + H]^+$ or $[M + 2H]^{2+}$/Rt (min) (Analytical condition) 1H-NMR: Chemical Shift |
|---|---|---|---|---|---|---|---|
| 14 | CN | 1 | 1 | 1 | 1 | 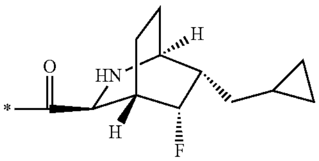 | 548.4/0.814 (Analytical condition A) $^1$H-NMR ($CDCl_3$) δ: 8.28 (1H, s), 7.21 (1H, s), 5.04-4.78 (5H, m), 4.61-4.19 (4H, m), 4.09 (1H, s), 3.67-3.55 (2H, m), 3.22 (1H, s), 2.36-1.67 (7H, m), 1.50-1.36 (2H, m), 0.81-0.70 (1H, m), 0.54-0.37 (2H, m), 0.21-0.02 (2H, m). |
| 15 | $CF_3$ | 1 | 1 | 1 | 1 | 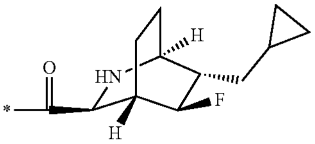 | 296.2/0.81 (Analytical condition A) $^1$H-NMR ($CDCl_3$) δ: 8.48 (1H, s), 7.38 (1H, s), 4.79-4.77 (4H, m) 4.51-4.26 (5H, m), 3.67 (2H, dd, J = 10.4, 20.1 Hz), 3.51 (1H, s), 2.97 (1H, s), 1.88-1.81 (3H, m), 1.55-1.28 (3H, m), 0.92-0.80 (3H, m), 0.54-0.46 (2H, m), 0.14-0.10 (2H, m). |
| 16 | $CF_3$ | 1 | 1 | 1 | 1 | 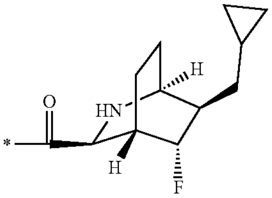 | 296.2/0.82 (Analytical condition A) |
| 17 | $CF_3$ | 1 | 1 | 1 | 1 | 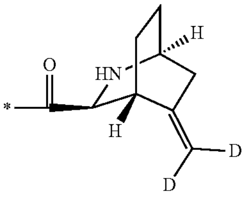 | 267.1/0.78 (Analytical condition A) 1H-NMR (CDCl3) δ: 8.45 (1H, s), 7.35 (1H, s), 4.83-4.69 (4H, br m), 4.50-4.30 (3H, m) 4.24 (1H, m), 3.78 (1H, s), 3.62 (2H, q, J = 10.1 Hz), 3.15 (1H, m), 2.67 (1H, m), 2.36 (1H, dd, J = 17.4 2.7 Hz), 2.31 (1H, m), 1.95-1.70 (2H, m), 1.62-1. 48 (2H, m). |
| 18 | $CF_3$ | 1 | 1 | 1 | 1 | 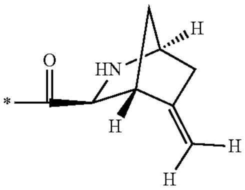 | 259.8/0.77 (Analytical condition A) 1H-NMR (DMSO-D6) δ: 8.35 (1H, s), 7.67 (1H, s), 5.01 (1H, s), 4.82-4.69 (total 4H, m), 4.67 (1H, s), 4.46 (2H, m), 4.14-3.99 (total 4H, m), 3.53 (1H, s), 3.16 (1H, s), 2.97 (1H, s), 2.14-1.99 (2H, m), 1.40-1.26 (2H, m). |

-continued

| Example | $R^{18}$ | a | b | c | d | E | LC-MS: $[M + H]^+$ or $[M + 2H]^{2+}$/Rt (min) (Analytical condition) 1H-NMR: Chemical Shift |
|---|---|---|---|---|---|---|---|
| 19 | $CF_3$ | 1 | 2 | 2 | 1 | 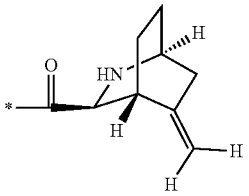 | 559.2/1.72 (Analytical condition B) |
| 20 | $CF_3$ | 2 | 1 | 2 | 1 | 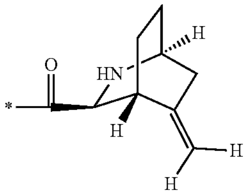 | 559.2/1.82 (Analytical condition B) |
| 21 | $CF_3$ | 1 | 2 | 1 | 2 | 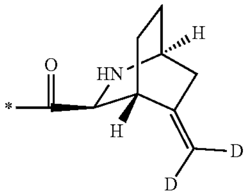 | 561.2/1.69 (Analytical condition B) $^1$H-NMR (DMSO-$D_6$) δ: 8.34 (1H, s), 7.77 (1H, s), 4.32 (4H, d, J = 5.5 Hz), 4.03 (2H, q, J = 10.8 Hz), 3.92 (1H, s), 3.68 (1H, br s), 3.37 (3H, br s), 3.04 (1H, s), 2.51 (1H, m), 2.40-2.20 (2H, m), 1.97-1.63 (5H, m), (1H, m), 1.57 (1H, m), 1.42 (2H, m). |
| 22 | $CF_3$ | 1 | 2 | 1 | 2 | 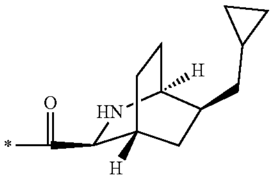 | 601.3/1.81 (Analytical condition B) $^1$H-NMR (DMSO-$D_6$) δ: 8.34 (1H, s), 7.76 (1H, s), 4.31 (4H, br s), 4.03 (2H, q, J = 11.1 Hz), 3.86 (1H, s), 3.68-3.53 (1H, m), 3.49-3.36 (total 4H, m), 2.67 (1H, br s), 2.12-0.98 (total 14H, m), 0.65 (1H, m), 0.38 (2H, m), 0.00 (2H, m). |
| 23 | $CF_3$ | 1 | 2 | 1 | 2 | 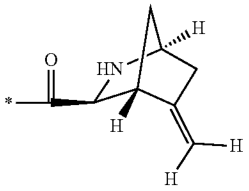 | 274.1/0.80 (Analytical condition A) $^1$H-NMR (DMSO-$D_6$) 8.36 (1H, s), 7.75 (1H, s), 5.27 (1H, s), 4.93 (1H, s), 4.35 (4H, br s), 4.26 (2H, d, J = 18.9 Hz), 4.04 (2H, q, J = 11.0 Hz) 3.75 (1H, m), 3.52-3.33 (total 3H, m), 3.20 (1H, s), 2.44 (2H, m), 1.98 (1H, m), 1.88 (2H, m), 1.76 (1H, m), 1.64 (2H, dd, J = 23.8, 11.0 Hz). |

-continued

| Example | $R^{18}$ | a | b | c | d | E | LC-MS: $[M + H]^+$ or $[M + 2H]^{2+}$/Rt (min) (Analytical condition) 1H-NMR: Chemical Shift |
|---|---|---|---|---|---|---|---|
| 24 | CN | 1 | 2 | 1 | 2 | 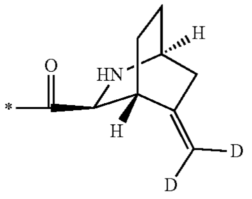 | 518.2/1.67 (Analytical condition B) $^1$H-NMR (DMSO-$D_6$) δ: 8.29 (1H, s), 7.62 (1H, s), 4.41 (4H, d, J = 13.4 Hz), 4.04 (2H, q, J = 11.0 Hz) 3.91 (1H, s), 3.67 (1H, br s), 3.37 (3H, br s), 3.03 (1H, s) 2.51 (1H, m), 2.38-2.19 (2H, m), 2.00-1.72 (4H, m), 1.68 (1H, m), 1.58 (1H, m), 1.42 (2H, m). |
| 25 | CN | 1 | 2 | 1 | 2 | 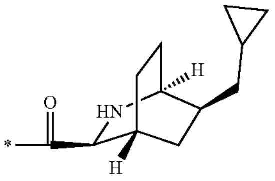 | 558.3/1.79 (Analytical condition B) $^1$H-NMR (DMSO-$D_6$) δ: 8.29 (1H, s), 7.61 (1H, s), 4.40 (4H, br s), 4.04 (2H, q, J = 11 Hz), 3.87 (1H, s), 3.67-3.51 (1H, m), 3.51-3.33 (total 4H, m), 2.68 (1H, br s), 2.10-0.95 (total 14H, m), 0.65 (1H, m), 0.38 (2H, m), 0.00 (2H, m). |
| 26 | CN | 1 | 2 | 1 | 2 | 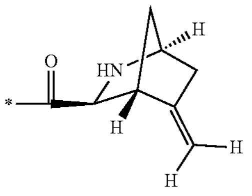 | 251.8./0.83 (Analytical condition B) $^1$H-NMR (DMSO-$D_6$) δ: 8.29 (1H, s), 7.62 (1H, s), 5.01 (1H, s), 4.68 (1H, S), 4.42 (4H, d, J = 16.4 Hz), 4.05 (2H, q, J = 10.4 Hz), 3.70-3.37 (total 6H, m), 2.87 (1H, s), 2.08 (2H, q, J = 15.1 Hz), 1.98-1.67 (total 4H, m), 1.34 (2H, m). |

Example 27

[(1S,3S,4R)-5-Methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone Example 27

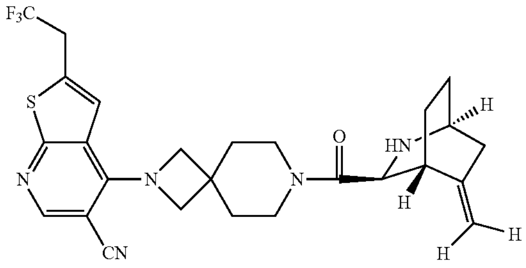

To a solution of the compound prepared in Reference example 1 (64 mg) in 2-propanol (2 mL) were added the compound prepared in Reference example 52 (61 mg) and N, N-diisopropylethylamine (0.21 mL) at room temperature, and the mixture was stirred at 80° C. for 4 hours. The solvent was removed under reduced pressure, and the residue was purified by silica gel column chromatography (chloroform/methanol) to yield Example 27 (107 mg).

LC-MS; $[M+H]^+$ 559.2/Rt (min) 1.67 (Analytical condition B)

$^1$H-NMR ($CDCl_3$) δ: 8.41 (1H, s), 7.37 (1H, s), 4.89 (1H, s), 4.80 (1H, s), 4.32 (4H, br s), 4.08 (1H, s), 3.87 (1H, m), 3.60 (2H, q, J=10.0 Hz), 3.46 (2H, m), 3.37 (1H, m), 3.22 (1H, m), 3.09 (1H, br s), 2.75 (1H, d, J=17.1 Hz), 2.35 (1H, d, J=17.1 Hz), 2.28 (1H, s), 1.86 (5H, br s), 1.76-1.61 (1H, m), 1.61-1.46 (2H, m).

Example 28

4-{7-[(1S,3S,4R)-5-Methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile Example 28

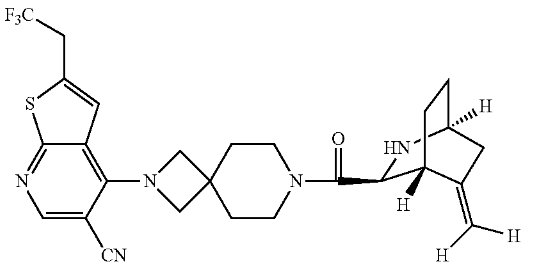

Example 28 (70 mg) was prepared according to a similar method to Example 27 by using the compound prepared in Reference example 6 and the compound prepared in Reference example 52.

LC-MS; $[M+H]^+$ 516.3/Rt (min) 0.85 (Analytical condition A)

$^1$H-NMR ($CDCl_3$) δ: 8.30 (1H, s), 7.24 (1H, s), 4.98 (1H, s), 4.89 (1H, s), 4.52 (2H, br s), 4.43 (2H, br s), 4.27 (1H, s), 4.01 (1H, m), 3.63 (2H, q, J=10.0 Hz), 3.57-3.30 (5H, m), 2.99 (1H, d, J=17.7 Hz), 2.41 (2H, m), 2.28 (1H, s), 1.94 (6H, br s), 1.76-1.54 (3H, m).

Tests

Test 1: Test for Evaluating the Inhibition of the Menin-MLL Binding $Menin_{1-615}$ wherein 6× His tag and HA tag are inserted in the N-terminus, and myc tag is inserted in the C-terminus (hereinafter, referred to as His-$Menin_{1-615}$), was diluted with an assay buffer (25 mmol/L HEPES, 150 mmol/L NaCl, 1 mmol/L dithiothreitol, 0.5% (w/v) Tween 80, 0.3% (w/v) BSA, 0.3% (w/v) skim milk) to adjust the final concentration to 30 nmol/L. The test compounds were also diluted with the assay buffer to adjust each concentration of the test compounds to 0.005 to 5 μmol/L. The prepared His-$Menin_{1-615}$ and test compounds were added to a light-shielding 384-well low-volume plate (Corning, #4514) in 2 μL/well and 6 ML/well, respectively, and the plate was covered with a lid for light-shielding (Corning, #3935), and incubated at room temperature for 3 hours. After the incubation, $MLL_{1-172}$ wherein FLAG tag is inserted in the C-terminus ($MLL_{1-172}$-FLAG), was separately diluted with the assay buffer to adjust the final concentration to 50 nmol/L. The prepared $MLL_{1-172}$-FLAG was added to the above plate in 2 μL/well, and the plate was covered with a lid for light-shielding and incubated at room temperature for an hour.

Then, anti-6HIS-d2 antibody (cisbio, 61HISDLA) and anti-FLAGM2-K antibody (cisbio, 61FG2KLA) were diluted with an antibody dilution buffer (50 mmol/L Tris, 150 mmol/L NaCl, 800 mmol/L KF, pH 7.4) to adjust the final concentration to 1.4 μg/mL to prepare an antibody mixture. The prepared antibody mixture was added to the above plate in 10 μL/well, and the plate was covered with a lid and incubated at 4° C. for 17 to 24 hours. After the incubation, the signal was detected with RUBYstar (BMG LABTECH). The binding inhibition rate (%) at each concentration of the test compounds was calculated from the following formula, and the $IC_{50}$ value was obtained, that corresponds to the concentration of the test compound at which the binding inhibition rate is 50%.

Binding inhibition rate (%)={1−(A−C)/(B−C)}×100

A: Signal in the presence of test compound

B: Signal of negative control (in the absence of test compound)

C: Signal of positive control (in the presence of known compound at the concentration which shows 100% inhibition ratio)

The results of the evaluation in Test 1 are shown in the following table.

| Example | HTRF $IC_{50}$ (nM) |
|---|---|
| 1 | 36.5 |
| 2 | 7.00 |
| 3 | 88.6 |
| 4 | 48.0 |
| 5 | 92.7 |
| 6 | 9.00 |
| 11 | 18.8 |
| 12 | 7.30 |
| 13 | 54.2 |
| 14 | 21.7 |

The compounds of Examples 1, 2, 4, 6, 11, 12, and 14 showed potent menin-MLL binding inhibition activity as shown in the above table.

Test 2: Test for Evaluating the Inhibition of Cell Proliferation

RS4; 11 cells were obtained from American Type Culture Collection (ATCC). The cells were cultured at 37° C. in the presence of 5% $CO_2$ in RPMI 1640 medium containing 10% fetal bovine serum and 1% penicillin/streptomycin. MOLM-13 cells were separately obtained from DSMZ (Deutsche Sammlung von Mikroorganismen und Zellkulturen GmbH). The cells were cultured at 37° C. in the presence of 5% $CO_2$ in RPMI 1640 medium containing 20 fetal bovine serum and 1% penicillin/streptomycin.

The cells were plated to a 96-well plate in 2000 cells/well, each test compound was added thereto to adjust the final concentration of DMSO to 0.1% of DMSO, and the cells were cultured for 7 days. After the cultivation, the cell viability was calculated with PrestoBlue™ Cell Viability Reagent (Invitrogen, A13261). The $IC_{50}$ value was calculated from a survival curve, that corresponds to the concentration of the test compound at which the cell proliferation inhibition rate is 50%.

The results of the evaluation in Test 2 are shown in the following table.

| | $IC_{50}$ (μM) | |
|---|---|---|
| Example | RS4; 11 | MOLM-13 |
| 1 | 0.09 | 0.28 |
| 2 | 0.19 | 0.26 |
| 3 | 0.59 | 0.80 |
| 4 | 0.29 | 0.71 |
| 5 | 0.20 | 0.28 |
| 6 | 0.09 | 0.20 |
| 7 | 0.74 | 0.73 |
| 8 | 0.88 | 0.74 |
| 9 | 0.71 | 0.72 |
| 10 | 2.70 | 2.00 |
| 11 | 0.08 | 0.15 |
| 12 | 0.06 | 0.09 |
| 13 | 0.44 | 0.69 |

-continued

| | $IC_{50}$ (μM) | |
|---|---|---|
| Example | RS4; 11 | MOLM-13 |
| 14 | 0.26 | 0.55 |
| 15 | 2.40 | — |
| 16 | 2.80 | — |
| 17 | <0.03 | <0.03 |
| 18 | 0.56 | 0.40 |
| 19 | 4.60 | 6.30 |
| 20 | 2.70 | 6.40 |
| 21 | <0.03 | <0.03 |
| 22 | <0.03 | 0.03 |
| 23 | 0.10 | 0.11 |
| 24 | <0.03 | <0.03 |
| 25 | <0.03 | 0.04 |
| 26 | 0.30 | 0.30 |
| 27 | 0.05 | 0.07 |
| 28 | 0.07 | 0.06 |

The compounds of Examples 1, 2, 3, 4, 5, 6, 7, 9, 11, 12, 13, 14, 17, 18, 21, 22, 23, 24, 25, 26, 27, and 28 showed good cell proliferation inhibition activity as shown in the above table. Especially, the compounds of Examples 1, 2, 5, 6, 11, 12, 17, 21, 22, 23, 24, 25, 26, 27, and 28 showed potent cell proliferation inhibitory activity.

Test 3: Test for the Inhibition of mRNA Transcription with Test Compounds

MV4; 11 cells were obtained from American Type Culture Collection (ATCC). The cells were cultured at 37° C. in the presence of 5% $CO_2$ in RPMI 1640 medium containing 10% fetal bovine serum and 1% penicillin/streptomycin. To the MV4; 11 cells was added each test compound to adjust the final concentration to 1 μmol/L, and the cells were cultured at 37° C. in the presence of 5% $CO_2$ for 20 to 24 hours. After the incubation, the total RNA was extracted from the cells with RNeasy™ Mini Kit (QIAGEN, 74106), and CDNA was synthesized with Superscript™ VILO™ CDNA Synthesis Kit (Invitrogen, #11754250). By using TaqMan™ Gene Expression Master Mix (Applied Biosystems, 4369016) and TaqMan™ probe (Applied Biosystems), the expression level of mRNA was quantified from the obtained cDNA with 7900HT (Applied Biosystems). The mRNA expression level of each obtained gene was fitted with the expression level of mRNA of GAPDH.

The results of the evaluation in Test 3 are shown in the following table.

| | mRNA at 1 μM (% control) | |
|---|---|---|
| Example | MEIS1 | HOXA9 |
| 1 | 31.8 | 55.0 |
| 2 | 26.6 | 48.2 |
| 3 | 52.6 | 54.0 |
| 4 | 47.1 | 52.5 |
| 5 | 32.3 | 44.3 |
| 6 | 27.4 | 45.9 |
| 11 | 20.6 | 45.0 |
| 12 | 18.4 | 42.6 |
| 13 | 39.6 | 45.4 |
| 14 | 38.5 | 51.4 |

The compounds of Examples 1, 2, 3, 4, 5, 6, 11, 12, 13, and 14 showed the mRNA transcription inhibition activity which is caused by the binding inhibition of menin and MLL.

Test 4: Pharmacokinetic Study

The test compound suspended in 0.5% methylcellulose was orally administered to 7-week-old male NOD. CB17-Prkdcscid/J mouse in a dose of 100 mg/kg. The blood sample was taken from jugular vein without anesthesia over time for 24 hours. The blood sample was centrifuged to obtain plasma. The plasma was pre-treated by methanol extraction method, and then analyzed with an LC-MS/MS to determine the concentration of the test compound. Based on the data from 0 hour after the administration until the time (t) when there was the final detection in the plasma, AUC was calculated by trapezoidal method. The evaluation result of Test 4 is shown in the following table.

| Example | $AUC_{0-t}$ (ng · hr/mL) |
|---|---|
| 1 | 10300 |
| 9 | 13400 |
| 11 | 6740 |
| 12 | 8970 |
| 21 | 24300 |
| 24 | 6970 |
| 27 | 17300 |
| 28 | 11600 |

As shown in the above table, particularly Examples 1, 9, 11, 12, 21, 24, 27, and 28 showed good compound-exposure in plasma.

INDUSTRIAL APPLICABILITY

The compounds of the present invention can inhibit the binding of a MLL fusion protein and menin to provide the antitumor effect.

The invention claimed is:

1. A compound selected from the group consisting of

[(1S,3S,4R)-5-($^2H_2$)methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone, 4-{7-[(1S,3S,4R)-5-($^2H_2$)methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile, 4-{7-[(1S,3S,4R)-5-methylidene-2-azabicyclo[2.2.1]heptane-3-carbonyl]-2,7-diazaspiro[3.5]nonan-2-yl}-2-(2,2,2-trifluoroethyl)thieno[2,3-b]pyridine-5-carbonitrile,

[(1S,3S,4R)-5-methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone, and 4-{7-[(1S,3S,4R)-5-methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile or pharmaceutically acceptable salt thereof.

2. The compound of claim 1 where the compound is [(1S,3S,4R)-5-($^2H_2$)methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone, or a pharmaceutically acceptable salt thereof.

3. The compound of claim 1 where the compound is 4-{7-[(1S,3S,4R)-5-($^2H_2$)methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile, or a pharmaceutically acceptable salt thereof.

4. The compound of claim 1 where the compound is [(1S,3S,4R)-5-methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone, or a pharmaceutically acceptable salt thereof.

5. The compound of claim 1 where the compound is 4-{7-[(1S,3S,4R)-5-methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile, or a pharmaceutically acceptable salt thereof.

6. A compound selected from the group consisting of [(1S,3S,4R)-5-($^2H_2$)methylidene-2-azabicyclo[2.2.2]octan-3-yl]{2-[2-(2,2,2-trifluoroethyl)-5-(trifluoromethyl)thieno[2,3-b]pyridin-4-yl]-2,7-diazaspiro[3.5]nonan-7-yl}methanone, or a pharmaceutically acceptable salt thereof and 4-{7-[(1S,3S,4R)-5-($^2H_2$)methylidene-2-azabicyclo[2.2.2]octane-3-carbonyl]-2,7-diazaspiro[3.5]nonan-2-yl}-2-(2,2,2-trifluoroethyl)thieno[2,3-b]pyridine-5-carbonitrile, or a pharmaceutically acceptable salt thereof.

7. A method for treating a tumor selected from MLL acute leukemia, MLL partial tandem duplicate acute leukemia, NPM mutated acute leukemia, MOZ acute leukemia, NUP98 acute leukemia, CALM acute leukemia, chronic myeloid leukemia, B-cell lymphoma, or multiple myeloma, comprising administering a compound of claim 6 or a pharmaceutically acceptable salt thereof to a patient in need thereof.

8. The method of claim 7, wherein the tumor is MLL acute leukemia, or NPM mutated acute leukemia.

9. A pharmaceutical composition comprising the compound of claim 1 or a pharmaceutically acceptable salt thereof in combination with at least one different agent or a pharmaceutically acceptable salt thereof, wherein the different agent is at least one agent selected from the group consisting of an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, an biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

10. A method of treating a subject with a tumor comprising administering to a subject with a tumor the compound of claim 1, and at least one different agent or a pharmaceutically acceptable salt thereof, wherein the different agent is at least one agent selected from an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic lymphocytic leukemia, chronic myeloid leukemia, myelodysplastic syndrome, polycythemia vera, malignant lymphoma (including B-cell lymphoma), myeloma (including multiple myeloma), brain tumor, thyroid cancer, small cell lung cancer, non-small cell lung cancer, breast cancer, liver cancer, hepatocellular cancer, colon cancer, rectal cancer, ovarian cancer, bladder cancer, renal cancer, renal cell cancer, prostate cancer, malignant melanoma, Ewing's sarcoma.

* * * * *